US007541517B2

(12) United States Patent
Flannagan et al.

(10) Patent No.: US 7,541,517 B2
(45) Date of Patent: Jun. 2, 2009

(54) *BACILLUS THURINGIENSIS CRY9* NUCLEIC ACIDS

(75) Inventors: Ronald D. Flannagan, Grimes, IA (US); André Abad, W. Des Moines, IA (US)

(73) Assignees: Pioneer Hi-Bred International, Inc., Johnston, IA (US); E.I. du Pont de Nemours and Company, Wilmington, DE (US)

(*) Notice: Subject to any disclaimer, the term of this patent is extended or adjusted under 35 U.S.C. 154(b) by 75 days.

(21) Appl. No.: 11/471,879

(22) Filed: Jun. 21, 2006

(65) Prior Publication Data

US 2006/0242733 A1 Oct. 26, 2006

Related U.S. Application Data

(62) Division of application No. 11/018,615, filed on Dec. 21, 2004.

(60) Provisional application No. 60/531,807, filed on Dec. 22, 2003.

(51) Int. Cl.

*A01H 5/00* (2006.01)
*A01H 5/10* (2006.01)
*C12N 15/82* (2006.01)
*C12N 15/32* (2006.01)

(52) U.S. Cl. .................. 800/302; 536/23.71; 435/320.1

(58) Field of Classification Search ....................... None
See application file for complete search history.

(56) References Cited

U.S. PATENT DOCUMENTS

| | | | | |
|---|---|---|---|---|
| 5,372,933 | A | 12/1994 | Zamarron et al. | |
| 6,489,542 | B1 | 12/2002 | Corbin et al. | |
| 7,169,971 | B2 * | 1/2007 | Arnaut et al. | 800/302 |
| 2003/0229919 | A1 | 12/2003 | Isaac et al. | |
| 2005/0138685 | A1 | 6/2005 | Flannagan et al. | |

FOREIGN PATENT DOCUMENTS

| | | |
|---|---|---|
| WO | WO 99/00407 | 1/1999 |
| WO | WO 00/11025 | 3/2000 |
| WO | WO 01/21821 | 3/2001 |

OTHER PUBLICATIONS de Maagd et al, 1999, Appl. Environ. Microbiol. 65:4369-4374.*
Tounsi et al, 2003, J. Appl. Microbiol. 95:23-28.*
Aaronson et al, 2001, FEMS Microbiol. Lett. 195:1-8.*
De Maagd et al, 2001, Trends Genet. 17:193-199.*
Guo et al, 2004, Proc. Natl. Acad. Sci. USA 101: 9205-9210.*
Walters et al, 1993, Biochem. Biophys. Res. Comm. 196:921-926.*
Schnepf et al, 1998, Microbiol. Molec. Biol. Rev. 62:775-806.*
Wasano et al (2001, Current Microbiol. 42:129-133).*
Wasano et al, 2003, GenBank Accession Nos. AY550111.*
Wasano et al, 2003, GenBank Accession Nos. AAC63366.*
De Maagd, R.A., et al., "How *Bacillus thuringiensis* has Evolved Specific Toxins to Colonize the Insect World," *Trends in Genetics*, Apr. 2001, pp. 193-199, vol. 17(4).
Lambert, B., et al., "A *Bacillus thuringiensis* Insecticidal Crystal Protein with a High Activity Against Members of the Family Noctuidae," *App. Env. Microbiol.*, 1996, pp. 80-86, vol. 62.
Rajamohan, F. and D.H. Dean, "*Bacillus thuringiensis* Insecticidal Proteins: Molecular Mode of Action," *Prog. Nucl. Acid Res. and Mol. Biol.*, 1998, pp. 1-27, vol. 60.
Wasano, N., et al., "Two δ-Endotoxin Genes, cry9Da and a Novel Related Gene, Commonly Occurring in Lepidoptera-Specific *Bacillus thuringiensis* Japanese Isolates that Produce Spherical Parasporal Inclusions," *Curr. Microbiol.*, 2001, pp. 129-133, vol. 42.
Aronson, A.I., and Y. Shai, "Why *Bacillus thuringiensis* Insecticidal Toxins are so Effective: Unique Features of Their Mode of Action," *FEMS Microbiology Letters*, 2001, pp. 1-8, vol. 195.
De Maagd, R.A., "Identification of *Bacillus thuringiensis* Delta-Endotoxin CryIC Domain III Amino Acid Residues Involved in Insect Specificity," *Applied and Environmental Microbiology*, 1999, pp. 4369-4374, vol. 65(10).
Guo, H.H., "Protein Tolerance to Random Amino Acid Change," *PNAS*, 2004, pp. 9205-9210, vol. 101.
Schnepf, E., et al., "*Bacillus thuringiensis* and Its Pesticidal Crystal Proteins," *Microbiology and Molecular Biology Reviews*, 1998, pp. 775-806, vol. 62(3).
Tounsi, S., et al., "Cloning and Study of the Expression of a Novel *cry1Ia*-type Gene from *Bacillus thuringiensis* Subsp. *Kurstaki,*" *Journal of Applied Microbiology*, 2003, pp. 23-28, vol. 95.
Walters, F.S., et al., Ion Channel Activity of N-Terminal Fragments From CRYIA(c) Delta-Endotoxin, *Biochemical and Biophysical Research Communications*, 1993, pp. 921-926, vol. 196(2).
Bravo, A., et al., "*Bacillus thuringiensis*: Mechanisms and Use," *Comprehensive Molecular Insect Science*, 2005, pp. 175-205, vol. 6.

* cited by examiner

*Primary Examiner*—Anne R Kubelik
(74) *Attorney, Agent, or Firm*—Alston & Bird LLP

(57) ABSTRACT

The invention provides nucleic acids, and variants and fragments thereof, obtained from strains of *Bacillus thuringiensis* encoding Cry9 δ-endotoxins having pesticidal activity against insect pests, including *Lepidoptera*. Particular embodiments of the invention provide isolated nucleic acids encoding pesticidal proteins, expression cassettes, and transformed plants comprising a nucleic acid of the invention.

7 Claims, 11 Drawing Sheets

| | 1 | | | | 50 |
|---|---|---|---|---|---|
| cry9aa1 | ---MNQNKHG | IIGASNCGCA | SDDVAKYPLA | NNPYSSALNL | NSCQNSSILN |
| cry9aa2 | ---mnqnkhg | iigasncgca | sddvakypla | nnpyssalnl | nscqnssiln |
| cry9da1 | MNRNNQNEYE | VIDAPHCGCP | ADDVVKYPLT | DDPNAGL..Q | NMNYKEYLQT |
| cry9da2 | ---------- | -----hcgcp | addvvkyplt | ddpnagl..q | nmnykeylqt |
| cry9d_rv1 | mnrnnqneye | iidaphcgcp | sddvvkyplt | ddpnagl..q | nmnykeylqm |
| cry9_like | ---------e | iidgtncgcs | sdevvkyplt | ddpnagl..q | nmnykeylqt |
| cry9_rv1 | ---------- | ---------- | ---------- | ---------- | ---------- |
| cry9eb1 | MNRNNQNDYE | VIDASNCGCA | SDDVVQYPLA | RDPNAVF..Q | NMHYKDYLQT |
| cry9fa | ---------- | ---------- | ---------- | ---------- | ---------- |
| cry9ea1 | MNRNNPNEYE | IIDAPYCGCP | SDDDVRYPLA | SDPNAAF..Q | NMNYKEYLQT |
| cry9ea2 | mnrnnpneye | iidapycgcp | sdddvrypla | sdpnaaf..q | nmnykeylqt |
| cry9ca1 | MNRNNQNEYE | IIDAPHCGCP | SDDDVRYPLA | SDPNAAL..Q | NMNYKDYLQM |
| cry9ba1 | ---------- | ---------- | ----VFELKT | CIWHAFFLTK | LSSYKDYLKM |
| Consensus | MNRNNQNEYE | IIDAP-CGCP | SDDVVKYPLA | DDPNAGLLNQ | NMNYKEYLQT |

| | 51 | | | | 100 |
|---|---|---|---|---|---|
| cry9aa1 | W........I | N.IIGDAAKE | AVSIGTTIVS | LITA...PSL | TGLISIVYDL |
| cry9aa2 | w........i | n.iigdaake | avsigttivs | lita...psl | tglisivydl |
| cry9da1 | YGGDYTDPLI | NPNLSVSGKD | VIQVGINIVG | RLLSFFGFPF | SSQWVTVYTY |
| cry9da2 | yggdytdpli | npnlsvsgkd | viqvginivg | rllsffgfpf | ssqwvtvyty |
| cry9d_rv1 | yggdytdpli | npnlsvsgkd | viqvginivg | rllsffgfpf | ssqwvtvyty |
| cry9_like | ydgdytgsli | npnlsintrd | vlqtginivg | rvlgflgvpf | agqlvtfytf |
| cry9_rv1 | ---------- | ---------d | vlqtgitivg | rvlgflgvpf | agqlvtfytf |
| cry9eb1 | YDGDYTGSFI | NPNLSINPRD | VLQTGINIVG | RLLGFLGVPF | AGQLVTFYTF |
| cry9fa | ---------- | ---------d | vlqtginivg | rllgflgvpf | agqlvtfytf |
| cry9ea1 | YDGDYTGSLI | NPNLSINPRD | VLQTGINIVG | RILGFLGVPF | AGQLVTFYTF |
| cry9ea2 | ydgdytgsli | npnlsinprd | vlqtginivg | rilgflgvpf | agqlvtfytf |
| cry9ca1 | TDEDYTDSYI | NPSLSISGRD | AVQTALTVVG | RILGALGVPF | SGQIVSFYQF |
| cry9ba1 | SEGDYIDSYI | NPG....NVRT | GLQTGIDIVA | VVVGALGGPV | GGILTGFLST |
| Consensus | YDGDYTDSLI | NPNLSINGRD | VLQTGINIVG | R-LGFLGVPF | AGQLVTFYTF |

| | 101 | | | | 150 |
|---|---|---|---|---|---|
| cry9aa1 | IGKVLGGSSG | QSISDLSICD | LLSIIDLRVS | QSVLNDGIAD | FNGSVLLYRN |
| cry9aa2 | igkvlggssg | qsisdlsicd | llsiidlrvs | qsvlndgiad | fngsvllyrn |
| cry9da1 | LLNSLWPDDE | NSVWDAFMER | VEELIDQKIS | EAVKGRALDD | LTGLQYNYNL |
| cry9da2 | llnslwpdde | nsvwdafmer | veelidqkis | eavkgraldd | ltglqynynl |
| cry9d_rv1 | llnslwpdde | nsvwdafmkr | ieelidqkis | eavkgralde | ltglqdnynl |
| cry9_like | llnqlwptnn | navweafmaq | ieelidqris | eqvvrnalda | ltgihdyyne |
| cry9_rv1 | llnqlwptnn | navweafmaq | veelidqris | dqvvrnaldd | ltglhdyyne |
| cry9eb1 | LLNQLWPTND | NAVWEAFMAQ | IEELINQRIS | EAVVGTAADH | LTGLHDNYEL |
| cry9fa | llnqlwptnd | navweafmaq | ieelinqris | eavvgtaadh | ltglhdnyel |
| cry9ea1 | LLNQLWPTND | NAVWEAFMAQ | IEELIDQKIS | AQVVRNALDD | LTGLHDYYEE |
| cry9ea2 | llnqlwptnd | navweafmaq | ieelidqkis | aqvvrnaldd | ltglhdyyee |
| cry9ca1 | LLNTLWPVND | TAIWEAFMRQ | VEELVNQQIT | EFARNQALAR | LQGLGDSFNV |
| cry9ba1 | LFGFLWPSND | QAVWEAFIEQ | MEELIEQRIS | DQVVRTALDD | LTGIQNYYNQ |
| Consensus | LLNQLWPTND | NAVWEAFMAQ | IEELIDQRIS | E-VV-NALDD | LTGLHD-YNL |

FIGURE 1A

```
           151                                                200
  cry9aa1  YLEALDSWNK NPNSASAEEL .RTRFRIADS EFDRILTRGS LTNGGSLARQ
  cry9aa2  ylealdswnk npnsasaeel .rtrfriads efdriltrgs ltnggslarq
  cry9da1  YVEALDEWLN RPNGAR.ASL VSQRFNILDS LFTQFMPSFG .SGPGS...Q
  cry9da2  yvealdewln rpngar.asl vsqrfnilds lftqfmpsfg .sgpgs...q
 cry9d_rv1 yvealdewln rpngar.asl vsqrfnilds lftqfmpsfg .sgpgs...q
 cry9_like ylaaleewle rpngar.anl afqrfenlhq lfvsqmpsfg .sgpgs...e
  cry9_rv1 ylaaleewld rpngar.anl afqrfenlht afvtrmpsfg .tgpgs...q
  cry9eb1  YVEALEEWLE RPNAAR.TNL LFNRFTTLDS LFTQFMPSFG .TGPGS...Q
   cry9fa  yvealeewle rpnaar.tnl lfnrfttlds lftqfmpsfg .tgpgs...q
  cry9ea1  YLAALEEWLE RPNGAR.ANL VTQRFENLHT AFVTRMPSFG .TGPGS...Q
  cry9ea2  ylaaleewle rpngar.anl vtqrfenlht afvtrmpsfg .tgpgs...q
  cry9ca1  YQRSLQNWLA DRNDTRNLSV VRAQFIALDL DFVNAIPLFA .VN.GQ...Q
  cry9ba1  YLIALKEWEE RPNGVR.ANL VLQRFEILHA LFVSSMPSFG .SGPGS...Q
 Consensus YLEALEEWLE RPNGARAANL VFQRFEILDS LFVQFMPSFG LTGPGSLARQ

           201                                                250
  cry9aa1  NAQILLLPSF ASAAFFHLLL LRDATRYGTN WGLYNATPFI NYQSKLVELI
  cry9aa2  naqilllpsf asaaffhlll lrdatrygtn wglynatpfi nyqsklveli
  cry9da1  NYATILLPVY AQAANLHLLL LKDADIYGAR WGLNQTQI.D QFHSRQQSLT
  cry9da2  nyatillpvy aqaanlhlll lkdadiygar wglnqtqi.d qfhsrqqslt
 cry9d_rv1 nystillpvy aqaanlhlll lkdadiygar wglnqtqi.d qfhsrqqslt
 cry9_like rdavalltvy aqaanlhlll lkdaeiygar wglnqgqi.n lyfnaqqdrt
  cry9_rv1 rdavalltvy aqaanlhlll lkdaeiygar wglqqsqi.n lyfnaqqdrt
  cry9eb1  NYAVPLLTVY AQAANLHLLL LKDAEIYGAR WGLNQNQI.N SFHTRQQERT
   cry9fa  nyavplltvy aqaanlhlll lkdaeiygar wglnqnqi.n sfhtrqqert
  cry9ea1  RDAVALLTVY AQAANLHLLL LKDAEIYGAR WGLQQGQI.N LYFNAQQERT
  cry9ea2  rdavalltvy aqaanlhlll lkdaeiygar wglqqgqi.n lyfnaqqert
  cry9ca1  ...VPLLSVY AQAVNLHLLL LKDASLFGEG WGFTQGEI.S TYYDRQLELT
  cry9ba1  RFQAQLLVVY AQAANLHLLL LADAEKYGAR WGLRESQIGN LYFNELQTRT
 Consensus NYAVALLTVY AQAANLHLLL LKDAEIYGAR WGLNQGQIFN LY--RQQERT

           251                                                300
  cry9aa1  ELYTDYCVHW YNRGFNELRQ RGTSATAWLE FHRYRREMTL MVLDIVASFS
  cry9aa2  elytdycvhw ynrgfnelrq rgtsatawle fhryrremtl mvldivasfs
  cry9da1  QTYTNHCVTA YNDGLAEL.. RGTTAESWFK YNQYRREMTL TAMDLVALFP
  cry9da2  qtytnhcvta yndglael.. rgttaeswfk ynqyrremtl tamdlvalfp
 cry9d_rv1 rtytnhcvtt yndglael.. rgtsveswlk yhqyrremtv tamdlvalfp
 cry9_like qiytnhcvat ynrglenl.. rgtnteswyn yhqfrremtl mamdlvalfp
  cry9_rv1 riytnhcvat ynrgledl.. kgtnteswyn yhqfrremtl mamdlvalfp
  cry9eb1  QYYTNHCVTT YNTGLDRL.. RGTNTESWLN YHRFRREMTL MAMDLVALFP
   cry9fa  qyytnhcvtt yntgldrl.. rgtnteswln yhrfrremtl mamdlvalfp
  cry9ea1  RIYTNHCVET YNRGLEDV.. RGTNTESWLN YHRFRREMTL MAMDLVALFP
  cry9ea2  riytnhcvet ynrgledv.. rgtnteswln yhrfrremtl mamdlvalfp
  cry9ca1  AKYTNYCETW YNTGLDRL.. RGTNTESWLR YHQFRREMTL VVLDVVALFP
  cry9ba1  RDYTNHCVNA YNNGLAGL.. RGTSAESWLK YHQFRREATL MAMDLIALFP
 Consensus -IYTNHCVTT YNRGL-ELRQ RGTNTESWLN YHQFRREMTL MAMDLVALFP
```

FIGURE 1B

```
           301                                                    350
  cry9aa1  SLDITNYPIE TDFQLSRVIY TDPIGF..VH RSSLRGE... .SWF...SFV
  cry9aa2  slditnypie tdfqlsrviy tdpigf..vh rsslrge... .swf...sfv
  cry9da1  YYNLRQYPDG TNPQLTREVY TDPIAFDPLE QPT...TQLC RSWYINPAFR
  cry9da2  yynlrqypdg tnpqltrevy tdpiafdple qpt...tqlc rswyinpafr
 cry9d_rv1 yynvrqypng anpqltrevy tdpivfnppe pps...gafc esfyniraar
 cry9_like yynlrqypng anpqltreiy tdpvvfnp.. pan...qglc rrwrnnp...
  cry9_rv1 yynvrqypng anpqltreiy tdpvvfnp.. pan...qglc rrwgnnp...
  cry9eb1  YYNVRQYPNG ANPQLTREIY TDPIVYNP.. PAN...QGIC RRWGNNP...
   cry9fa  yynvrqypng anpqltreiy tdpivynp.. pan...qgic rrwgnnp...
  cry9ea1  FYNVRQYPNG ANPQLTREIY TDPIVYNP.. PAN...QGIC RRWGNNP...
  cry9ea2  fynvrqypng anpqltreiy tdpivynp.. pan...qgic rrwgnnp...
  cry9ca1  YYDVRLYPTG SNPQLTREVY TDPIVFNP.. PAN...VGLC RRWGTNP...
  cry9ba1  YYNTRRYPIA VNPQLTREVY TDPLGV.PSE ESSLFPELRC LRWQETSA..
Consensus  YYNVRQYPNG ANPQLTREIY TDPIVFNP-E PANLRGQGLC RRWGNNPAFR

           351                                                    400
  cry9aa1  NRANFSDLEN AIPNPRPSWF ..LNNMIIST GSLTLPVSPS TDRARVWYGS
  cry9aa2  nranfsdlen aipnprpswf ..lnnmiist gsltlpvsps tdrarvwygs
  cry9da1  NHLNFSVLEN SLIRP.PHLF ERLSNLQILV NYQ..TNGSA ......WRGS
  cry9da2  nhlnfsvlen slirp.phlf erlsnlqilv nyq..tngsa ......wrgs
 cry9d_rv1 erltfsqlen aiirp.prlf erfqalgiyt gearlnqnsa p..tnywigh
 cry9_like .ymtfselen tfirp.phlf drlnsltins hrf..pissn f..mdywagh
  cry9_rv1 .ymtfsglen afirp.phlf drlnsltins hrf..pissn f..mdywagh
  cry9eb1  .YNTFSELEN AFIRP.PHLF DRLNRLTISR NRYTAPTTNS Y..LDYWSGH
   cry9fa  .yntfselen afirp.phlf drlnrltisr nrytapttns y..ldywsgh
  cry9ea1  .YNTFSELEN AFIRP.PHLF ERLNRLTISR NRYTAPTTNS F..LDYWSGH
  cry9ea2  .yntfselen afirp.phlf erlnrltisr nrytapttns f..ldywsgh
  cry9ca1  .YNTFSELEN AFIRP.PHLF DRLNSLTISS NRF..PVSSN F..MDYWSGH
  cry9ba1  ..MTFSNLEN AIISS.PHLF DTINNLMIYT GSFSVHLTNQ L..IEGWIGH
Consensus  NYNTFSELEN AFIRPRPHLF DRLNNLTIS- NR-TAPT-SS FDRLDYWSGH

           401                                                    450
  cry9aa1  RDRISPANSQ FIT..ELISG QHTTATQTIL G...RNIFRV DSQAC....N
  cry9aa2  rdrispansq fit..elisg qhttatqtil g...rnifrv dsqac....n
  cry9da1  RVRYHYLHS. .SIIQEKSYG LLSDPVGANI NVQNNDIYQI ISQV.SNFAS
  cry9da2  rvryhylhs. .siiqeksyg llsdpvgani nvqnndiyqi isqv.snfas
 cry9d_rv1 firntrlgd. .sttittnyg ttnnrltnfi ppttsdvyqi nsis.snlas
 cry9_like tlrrsymnn. .savqedsyg attst.rvti ntgvngtnri esta.vdfrs
  cry9_rv1 tlrrsymnn. .savqedsyg aitpt.rvti npgvngtnhi esta.vdfrs
  cry9eb1  TLQSQYANN. .PTTYETSYG QITSN.TRLF NT.TNGANAI DSRA.RNFGN
   cry9fa  tlqsqyann. .pttyetsyg qitsn.trlf nt.tnganai dsra.rnfgn
  cry9ea1  TLQSQHANN. .PTTYETSYG QITSN.TRLF NT.TNGARAI DSRA.RNFGN
  cry9ea2  tlqsqhann. .pttyetsyg qitsn.trlf nt.tngarai dsra.rnfgn
  cry9ca1  TLRRSYLND. .SAVQEDSYG LITTT.RATI NPGVDGTNRI ESTA.VDFRS
  cry9ba1  SVTSSLLASG PTTVLRRNYG STTS.IVNYF SFNDRDVYQI NTRSHTGLGF
Consensus  TLRSSYANNQ FSTTQETSYG QITSN-TRLI NTGTNG-N-I DSRACRNFG-
```

FIGURE 1C

```
          451                                                 500
  cry9aa1 LNDTTYGVNR AVFYHDASEG SQRSVYEGYI RTTGIDNPRV QNINTYLPGE
  cry9aa2 lndttygvnr avfyhdaseg sqrsvyegyi rttgidnprv qnintylpge
  cry9da1 PVGSSYSVWD TNFYLSS..G QVSGISGYTQ QGIPAVCLQQ RNSTDELPSL
  cry9da2 pvgssysvwd tnfylss..g qvsgisgytq qgipavclqq rnstdelpsl
 cry9d_rv1 alstlfgvtr aqfhygs..g iiwsyvg..q nnvlpqchqn ynsieelpnq
cry9_like gllgvygvhr asf.vpg..g lfngtispan ag....crnl hdtrdelple
  cry9_rv1 glvgiygvhr asf.vpg..g lfngtispan ag....crnl hdtrdvlple
  cry9eb1 LYANLYGVSY LNI.FPT..G VMSEITSAPN T.....CWQD LTTTEELPLV
   cry9fa lyanlygvsy lni.fpt..g vmseitsapn t.....cwqd lttteelplv
  cry9ea1 LYANLYGVSS LNI.FPT..G VMSEITNAAN T.....CRQD LTTTEELPLE
  cry9ea2 lyanlygvss lni.fpt..g vmseitnaan t.....crqd lttteelple
  cry9ca1 ALIGIYGVNR ASF.VPG..G LFNGTTSPAN GG....CRDL YDTNDELPPD
  cry9ba1 QNAPLFGITR AQFY.PG..G TYS.....VT QRNALTCEQN YNSIDELPSL
Consensus L-ANLYGVSR ANFYFP-SEG VMSGITSAAN TG----CRQD LNTTDELPLE

          501                                                 550
  cry9aa1 NSDIPTPEDY THILSTTINL TGGLRQVASN RRSS..LVMY GWTHKSLARN
  cry9aa2 nsdiptpedy thilsttinl tgglrqvasn rrss..lvmy gwthkslarn
  cry9da1 NPEGDIIRNY SHRLSHITQY RFQATQSGSP STVSANLPTC VWTHRDVDLD
  cry9da2 npegdiirny shrlshitqy rfqatqsgsp stvsanlptc vwthrdvdld
 cry9d_rv1 sde.ptvrsy shrlshitsf nf.svqlnnp vislgnmpvy vwthrsvdln
cry9_like enng....sp shrlshvtfl sfltdqag.s irnsgavply vwarqdidln
  cry9_rv1 enng....sp shrlshvtff kfstnqag.s langgsvply vwarqdidfn
  cry9eb1 NNN....... FNLLSHVTFL RFNTTQGG.P LATVGFVPTY VWTRQDVDFN
   cry9fa nnn....... fnllshvtfl rfnttqgg.p latvgfvpty vwtrqdvdfn
  cry9ea1 NNN....... FNLLSHVTFL RFNTTQGG.P LATLGFVPTY VWTREDVDFT
  cry9ea2 nnn....... fnllshvtfl rfnttqgg.p latlgfvpty vwtredvdft
  cry9ca1 ESTG....SS THRLSHVTFF SFQTNQAG.S IANAGSVPTY VWTRRDVDLN
  cry9ba1 DPNEPISRSY SHRLSHITSY LHRVLTIDGI NIYSGNLPTY VWTHRDVDLT
Consensus NNNGP--RSY SHRLSHVTFL RFNTTQGGSP LATSG-VPTY VWTRRDVDLN

          551                                                 600
  cry9aa1 NTINPDRITQ IPLTKVDTRG TGVSYVNDPG FIGGALLQRT DHGSLGVLRV
  cry9aa2 ntinpdritq ipltkvdtrg tgvsyvndpg figgallqrt dhgslgvlrv
  cry9da1 NTITANQITQ LPLVKAYELS SGATVVKGPG FTGGDVIRRT NTGGFGAIRV
  cry9da2 ntitanqitq lplvkayels sgatvvkgpg ftggdvirrt ntggfgairv
 cry9d_rv1 ntitsdritq lpavkastlg agaivvkgpg ftggdvirrt svgdfgtirv
cry9_like ntitanritq lplvkaseia agttvvrgpg ftggdilrrt sagtlgtirv
  cry9_rv1 ntitanritq lplvkafeia agttivkgpg ftggdilrrt stgtlgtirv
  cry9eb1 NIITPNRITQ IPVVKAYELS SGATVVKGPG FTGGDVIRRT NTGGFGAIRV
   cry9fa niitpnritq ipvvkayels sgatvvkgpg ftggdvirrt ntggfgairv
  cry9ea1 NTITADRITQ LPWVKASEIG GGTTVVKGPG FTGGDILRRT DGGAVGTIRA
  cry9ea2 ntitadritq lpwvkaseig ggttvvkgpg ftggdilrrt dggavgtira
  cry9ca1 NTITPNRITQ LPLVKASAPV SGTTVLKGPG FTGGGILRRT TNGTFGTLRV
  cry9ba1 NTITADRITQ LPLVKSFEIP AGTTVVRGPG FTGGDILRRT GVGTFGTIRV
Consensus NTITANRITQ LPLVKASE-G SGTTVVKGPG FTGGDILRRT -TG-FGTIRV
```

FIGURE 1D

```
              601                                                  650
cry9aa1       QFPLHLRQQY RIRVRYASTT NIRLSVNGSF GTISQN...L PSTMRLGEDL
cry9aa2       qfplhlrqqy rirvryastt nirlsvngsf gtisqn...l pstmrlgedl
cry9da1       SVTGPLTQRY RIRFRYASTI DF..DFFVTR GGTTINNFRF TRTMNRGQES
cry9da2       svtgpltqry rirfryasti df..dffvtr ggttinnfrf trtmnrgqes
cry9d_rv1     svtgsltqqy rirfryasti df..dffvir ggttinnfrf thtmssgees
cry9_like     nvnspltqry rvrfryastt df..nffvir ggttvnnftf prtmnsgqes
cry9_rv1      nvnspltqry rvrfryastv df..dffvsr ggttvnnfrf prtmsrgqes
cry9eb1       SVTGPLTQRY RIRFRYASTI DF..DFFVTR GGTTINNFRF TRTMNRGQES
cry9fa        svtgpltqry rirfryasti df..dffvtr ggttinnfrf trtmnrgqes
cry9ea1       NVNAPLTQQY RIRLRYASTT SFVVNLFVNN SAA...GFTL PSTMAQNGSL
cry9ea2       nvnapltqqy rirlryastt sfvvnlfvnn saa...gftl pstmaqngsl
cry9ca1       TVNSPLTQQY RLRVRFASTG NFSIR..VLR GGVSIGDVRL GSTMNRGQEL
cry9ba1       RTTAPLTQRY RIRFRFASTT NLFIGIRV.. GDRQVNYFDF GRTMNRGDEL
Consensus     SVTGPLTQRY RIRFRYASTT DF--DFFVTR GGTTINNFRF PRTMNRGQES

              651                                                  700
cry9aa1       RYGSFAIREF NTSIRP.... ..TASPDQIR LTIEPSFI.R QEVYVDRIEF
cry9aa2       rygsfairef ntsirp.... ..taspdqir ltiepsfi.r qevyvdrief
cry9da1       RYESYRTVEF TT......PF NFTQSQDIIR TSI.QGLSGN GEVYLDRIEI
cry9da2       ryesyrtvef tt......pf nftqsqdiir tsi.qglsgn gevyld~~~~
cry9d_rv1     ryesyrtvef st......pf nftqsqdiir tsi.qglsgn gevyldriei
cry9_like     ryesyvtref st......sf nflqiqdtlr ltv.qsfssg qqvyvd~~~~
cry9_rv1      ryesyvtsef tt......pf tftqsqdfir tsi.qglsgn gevyldriei
cry9eb1       RYESYRTVEF TT......PF NFTQSQDIIR TSI.QGLSGN GEVYLDRIEI
cry9fa        ryesyrtvef tt......pf nftqsqdiir tsi.qglsgn gevyldriei
cry9ea1       TYESFNTLEV TH......TI RFSQSDTTLR LNIFPSISGQ .EVYVDKLEI
cry9ea2       tyesfntlev th......ti rfsqsdttlr lnifpsisgq .evyvdklei
cry9ca1       TYESFFTREF TTTGPFNPPF TFTQAQEILT VN.AEGVSTG GEYYIDRIEI
cry9ba1       RYESFATREF TTD......F NFRQPQELIS V.FANAFSAG QEVYFDRIEI
Consensus     RYESYRT-EF TTSIRP--PF NFTQSQDIIR TSI-QGLSGN GEVYLDRIEI

              701                                                  750
cry9aa1       IPVNPTREAK EDLEAAKKAV .ASLFTRTRD GLQVNVKDYQ VDQAANLVSC
cry9aa2       ipvnptreak edleaakkav .aslftrtrd glqvnvkdyq vdqaanlvsc
cry9da1       IPVNPAREAE EDLEAAKKAA RQNLFTRTRD GLQVNVTDYQ VDQAANLVSC
cry9da2       ~~~~~~~~~~ ~~~~~~~~~~ ~~~~~~~~~~ ~~~~~~~~~~ ~~~~~~~~~~
cry9d_rv1     ipvnptreae edledakkav .aglftrtrd g~~~~~~~~~ ~~~~~~~~~~
cry9_like     ~~~~~~~~~~ ~~~~~~~~~~ ~~~~~~~~~~ ~~~~~~~~~~ ~~~~~~~~~~
cry9_rv1      ipvnpareae edleaakkav .aslftrtrd ~~~~~~~~~~ ~~~~~~~~~~
cry9eb1       IPVNPTREAE EDLEAAKKAV .ASLFTRTRD GLQVNVTDYQ VDQAANLVSC
cry9fa        ipvnptreae edleaakkav .aslftrtrd ~~~~~~~~~~ ~~~~~~~~~~
cry9ea1       VPINPTREAE EDLEDAKKAV .ASLFTRTRD GLQVNVTDYQ VDQAANLVSC
cry9ea2       vpinptreae edledakkav .aslftrtrd glqvnvtdyq vdqaanlvsc
cry9ca1       VPVNPAREAE EDLEAAKKAV .ASLFTRTRD GLQVNVTDYQ VDQAANLVSC
cry9ba1       IPVNPAREAK EDLEAAKKAV .ASLFTRTRD GLQVNVKDYQ VDQAANLVSC
Consensus     IPVNPTREAE EDLEAAKKAV -ASLFTRTRD GLQVNVTDYQ VDQAANLVSC
```

FIGURE 1E

```
          751                                                    800
cry9aa1   LSDEQYGYDK KMLLEAVRAA KRLSRERNLL QDPDFNTINS TEENGWKASN
cry9aa2   lsdeqygydk kmlleavraa krlsrernll qdpdfntins teengwkasn
cry9da1   LSDEQYGHDK KMLLEAVRAA KRLSRERNLL QDPDFNTINS TEENGWKASN
cry9da2   ~~~~~~~~~~ ~~~~~~~~~~ ~~~~~~~~~~ ~~~~~~~~~~ ~~~~~~~~~~
cry9d_rv1 ~~~~~~~~~~ ~~~~~~~~~~ ~~~~~~~~~~ ~~~~~~~~~~ ~~~~~~~~~~
cry9_like ~~~~~~~~~~ ~~~~~~~~~~ ~~~~~~~~~~ ~~~~~~~~~~ ~~~~~~~~~~
cry9_rv1  ~~~~~~~~~~ ~~~~~~~~~~ ~~~~~~~~~~ ~~~~~~~~~~ ~~~~~~~~~~
cry9eb1   LSDEQYAHDK KMLLEAVRAA KRLSRERNLL QDPDFNTINS TEENGWKASN
cry9fa    ~~~~~~~~~~ ~~~~~~~~~~ ~~~~~~~~~~ ~~~~~~~~~~ ~~~~~~~~~~
cry9ea1   LSDEQYGHDK KMLLEAVRAA KRLSRERNLL QDPDFNEINS TEENGWKASN
cry9ea2   lsdeqyghdk kmlleavraa krlsrernll qdpdfneins teengwkasn
cry9ca1   LSDEQYGHDK KMLLEAVRAA KRLSRERNLL QDPDFNTINS TEENGWKASN
cry9ba1   LSDEQYGYDK KMLLEAVRAA KRLSRERNLL QDPDFNTINS TEENGWKASN
Consensus LSDEQYGHDK KMLLEAVRAA KRLSRERNLL QDPDFNTINS TEENGWKASN

          801                                                    850
cry9aa1   GVTISEGGPF YKGRAIQLAS ARENYPTYIY QKVDASELKP YTRYRLDGFV
cry9aa2   gvtiseggpf ykgraiqlas arenyptyiy qkvdaselkp ytryrldgfv
cry9da1   GVTISEGGPF FKGRALQLAS ARENYPTYIY QKVDASVLKP YTRYRLDGFV
cry9da2   ~~~~~~~~~~ ~~~~~~~~~~ ~~~~~~~~~~ ~~~~~~~~~~ ~~~~~~~~~~
cry9d_rv1 ~~~~~~~~~~ ~~~~~~~~~~ ~~~~~~~~~~ ~~~~~~~~~~ ~~~~~~~~~~
cry9_like ~~~~~~~~~~ ~~~~~~~~~~ ~~~~~~~~~~ ~~~~~~~~~~ ~~~~~~~~~~
cry9_rv1  ~~~~~~~~~~ ~~~~~~~~~~ ~~~~~~~~~~ ~~~~~~~~~~ ~~~~~~~~~~
cry9eb1   GVTISEGGPF YKGRALQLAS ARENYPTYIY QKVDASELKP YTRYRLDGFV
cry9fa    ~~~~~~~~~~ ~~~~~~~~~~ ~~~~~~~~~~ ~~~~~~~~~~ ~~~~~~~~~~
cry9ea1   GVTISEGGPF FKGRALQLAS ARENYPTYIY QKVDASTLKP YTRYKLDGFV
cry9ea2   gvtiseggpf fkgralqlas arenyptyiy qkvdastlkp ytrykldgfv
cry9ca1   GVTISEGGPF FKGRALQLAS ARENYPTYIY QKVDASVLKP YTRYRLDGFV
cry9ba1   GVTISEGGPF YKGRALQLAS ARENYPTYIY QKVDASELKP YTRYRSDGFV
Consensus GVTISEGGPF -KGRALQLAS ARENYPTYIY QKVDASELKP YTRYRLDGFV

          851                                                    900
cry9aa1   KSSQDLEIDL IHHHKVHLVK NVPDNLVSDT YPDDSCSGIN RCQEQQMVNA
cry9aa2   kssqdleidl ihhhkvhlvk nvpdnlvsdt ypddscsgin rcqeqqmvna
cry9da1   KSSQDLEIDL IHYHKVHLVK NVPDNLVSDT YSDGSCSGMN RCEEQQMVNA
cry9da2   ~~~~~~~~~~ ~~~~~~~~~~ ~~~~~~~~~~ ~~~~~~~~~~ ~~~~~~~~~~
cry9d_rv1 ~~~~~~~~~~ ~~~~~~~~~~ ~~~~~~~~~~ ~~~~~~~~~~ ~~~~~~~~~~
cry9_like ~~~~~~~~~~ ~~~~~~~~~~ ~~~~~~~~~~ ~~~~~~~~~~ ~~~~~~~~~~
cry9_rv1  ~~~~~~~~~~ ~~~~~~~~~~ ~~~~~~~~~~ ~~~~~~~~~~ ~~~~~~~~~~
cry9eb1   KSSQDLEIDL IHHHKVHLVK NVLDNLVSDT YPDDSCSGIN RCEEQQMVNA
cry9fa    ~~~~~~~~~~ ~~~~~~~~~~ ~~~~~~~~~~ ~~~~~~~~~~ ~~~~~~~~~~
cry9ea1   QSSQDLEIDL IHHHKVHLVK NVPDNLVSDT YSDGSCSGIN RCEEQHQVDV
cry9ea2   qssqdleidl ihhhkvhlvk nvpdnlvsdt ysdgscsgin rceeqhqvdv
cry9ca1   KSSQDLEIDL IHHHKVHLVK NVPDNLVSDT YSDGSCSGIN RCDEQHQVDM
cry9ba1   KSSQDLEIDL IHHHKVHLVK NVPDNLVSDT YPDDSCSGIN RCQEQQMVNA
Consensus KSSQDLEIDL IHHHKVHLVK NVPDNLVSDT Y-D-SCSGIN RCEEQQMVNA
```

FIGURE 1F

```
           901                                                950
  cry9aa1 QLETEHHHPM DCCEAAQTHE FSSYIDTGDL NSSVDQGIWA IFKVRTTDGY
  cry9aa2 qletehhhpm dcceaaqthe fssyidtgdl nssvdqgiwa ifkvrttdgy
  cry9da1 QLETEHHHPM DCCEAAQTHE FSSYINTGDL NASVDQGIWV VLKVRTTDGY
  cry9da2 ~~~~~~~~~~ ~~~~~~~~~~ ~~~~~~~~~~ ~~~~~~~~~~ ~~~~~~~~~~
cry9d_rv1 ~~~~~~~~~~ ~~~~~~~~~~ ~~~~~~~~~~ ~~~~~~~~~~ ~~~~~~~~~~
cry9_like ~~~~~~~~~~ ~~~~~~~~~~ ~~~~~~~~~~ ~~~~~~~~~~ ~~~~~~~~~~
  cry9_rv1 ~~~~~~~~~~ ~~~~~~~~~~ ~~~~~~~~~~ ~~~~~~~~~~ ~~~~~~~~~~
  cry9eb1 QLETEHHHPM DCCEAAQTHE FSSYIDTGDL NSTVDQGIWV IFKVRTTDGY
   cry9fa ~~~~~~~~~~ ~~~~~~~~~~ ~~~~~~~~~~ ~~~~~~~~~~ ~~~~~~~~~~
  cry9ea1 QLDAE.DHPK DCCEAAQTHE FSSYIHTGDL NASVDQGIWV VLQVRTTDGY
  cry9ea2 qldae.dhpk dcceaaqthe fssyihtgdl nasvdqgiwv vlqvrttdgy
  cry9ca1 QLDAEH.HPM DCCEAAQTHE FSSYINTGDL NASVDQGIWV VLKVRTTDGY
  cry9ba1 QLETEHHHPM DCCEAAQTHE FSSYIDTGDL NSSVDQGIWA IFKVRTTDGY
Consensus QLETEHHHPM DCCEAAQTHE FSSYIDTGDL N-SVDQGIWV --KVRTTDGY

           951                                               1000
  cry9aa1 ATLGNLELVE VGPLSGESLE REQRDNTKWS AELGRKRAET DRVYQDAKQS
  cry9aa2 atlgnlelve vgplsgesle reqrdntkws aelgrkraet drvyqdakqs
  cry9da1 ATLGNLELVE VGPLSGESLE REQRDNAKWN AELGRKRAEI DRVYLAAKQA
  cry9da2 ~~~~~~~~~~ ~~~~~~~~~~ ~~~~~~~~~~ ~~~~~~~~~~ ~~~~~~~~~~
cry9d_rv1 ~~~~~~~~~~ ~~~~~~~~~~ ~~~~~~~~~~ ~~~~~~~~~~ ~~~~~~~~~~
cry9_like ~~~~~~~~~~ ~~~~~~~~~~ ~~~~~~~~~~ ~~~~~~~~~~ ~~~~~~~~~~
 cry9_rv1 ~~~~~~~~~~ ~~~~~~~~~~ ~~~~~~~~~~ ~~~~~~~~~~ ~~~~~~~~~~
  cry9eb1 ATLGNLELVE VGPLLGEPLE REQRENAKWN AELGRKRAET DRVYQDAKQS
   cry9fa ~~~~~~~~~~ ~~~~~~~~~~ ~~~~~~~~~~ ~~~~~~~~~~ ~~~~~~~~~~
  cry9ea1 ATLGNLELVE VGPLSGESLE REQRDNAKWN EEVGRKRAET DRIYQDAKQA
  cry9ea2 atlgnlelve vgplsgesle reqrdnakwn eevgrkraet driyqdakqa
  cry9ca1 ATLGNLELVE VGPLSGESLE REQRDNAKWN AELGRKRAEI DRVYLAAKQA
  cry9ba1 ATLGNLELVE VGPLSGESLE REQRDNTKWS AELGRKRAET DRVYQDAKQS
Consensus ATLGNLELVE VGPLSGESLE REQRDNAKWN AELGRKRAET DRVYQDAKQ-

           1001                                              1050
  cry9aa1 INHLFVDYQD QQLNPEIGMA DIMDAQNLVA SISDVYSDAV LQIPGINYEI
  cry9aa2 inhlfvdyqd qqlnpeigma dimdaqnlva sisdvysdav lqipginyei
  cry9da1 INHLFVDYQD QQLNPEIGLA EINEASNLVE SISGVYSDTL LQIPGINYEI
  cry9da2 ~~~~~~~~~~ ~~~~~~~~~~ ~~~~~~~~~~ ~~~~~~~~~~ ~~~~~~~~~~
cry9d_rv1 ~~~~~~~~~~ ~~~~~~~~~~ ~~~~~~~~~~ ~~~~~~~~~~ ~~~~~~~~~~
cry9_like ~~~~~~~~~~ ~~~~~~~~~~ ~~~~~~~~~~ ~~~~~~~~~~ ~~~~~~~~~~
 cry9_rv1 ~~~~~~~~~~ ~~~~~~~~~~ ~~~~~~~~~~ ~~~~~~~~~~ ~~~~~~~~~~
  cry9eb1 INHLFVDYQD QQLNPQIGMA DIMDAQNLVA SISDVYSDAV LQIPGINYEI
   cry9fa ~~~~~~~~~~ ~~~~~~~~~~ ~~~~~~~~~~ ~~~~~~~~~~ ~~~~~~~~~~
  cry9ea1 INHLFVDYQD QQLSPEVGMA DIIDAQNLIA SISDVYSDAV LQIPGINYEM
  cry9ea2 inhlfvdyqd qqlspevgma diidaqnlia sisdvysdav lqipginyem
  cry9ca1 INHLFVDYQD QQLNPEIGLA EINEASNLVE SISGVYSDTL LQIPGINYEI
  cry9ba1 INHLFVDYQD QQLNPEIGMA DIMDAQNLVA SISDVYSDAV LQIPGINYEI
Consensus INHLFVDYQD QQLNPEIGMA DIMDAQNLVA SISDVYSDAV LQIPGINYEI
```

FIGURE 1G

```
           1051                                                     1100
  cry9aa1  YTELSNRLQQ ASYLYTSRNA VQNGDFNNGL DSWNATAGAS VQQDGNTHFL
  cry9aa2  ytelsnrlqq asylytsrna vqngdfnngl dswnatagas vqqdgnthfl
  cry9da1  YTELSDRLQQ ASYLYTSRNA VQNGDFNSGL DSWNTTTDAS VQQDGNMHFL
  cry9da2  ~~~~~~~~~~ ~~~~~~~~~~ ~~~~~~~~~~ ~~~~~~~~~~ ~~~~~~~~~~
cry9d_rv1  ~~~~~~~~~~ ~~~~~~~~~~ ~~~~~~~~~~ ~~~~~~~~~~ ~~~~~~~~~~
cry9_like  ~~~~~~~~~~ ~~~~~~~~~~ ~~~~~~~~~~ ~~~~~~~~~~ ~~~~~~~~~~
  cry9_rv1 ~~~~~~~~~~ ~~~~~~~~~~ ~~~~~~~~~~ ~~~~~~~~~~ ~~~~~~~~~~
  cry9eb1  YTELSNRLQQ ASYLYTSRNA VQNGDFNNGL DSWNATAGAS VQQDGNTHFL
   cry9fa  ~~~~~~~~~~ ~~~~~~~~~~ ~~~~~~~~~~ ~~~~~~~~~~ ~~~~~~~~~~
  cry9ea1  YTELSNRLQQ ASYLYTSRNV VQNGDFNSGL DSWNATTDTA VQQDGNMHFL
  cry9ea2  ytelsnrlqq asylytsrnv vqngdfnsgl dswnattdta vqqdgnmhfl
  cry9ca1  YTELSDRLQQ ASYLYTSRNA VQNGDFNSGL DSWNTTMDAS VQQDGNMHFL
  cry9ba1  YTELSNRLQQ ASYLYTSRNA VQNGDFNNGL DSWNATAGAS VQQDGNTHFL
Consensus  YTELSNRLQQ ASYLYTSRNA VQNGDFN-GL DSWNATA-AS VQQDGN-HFL

           1101                                                     1150
  cry9aa1  VLSHWDAQVS QQFRVQPNCK YVLRVTAEKV GGGDGYVTIR DDAHHTETLT
  cry9aa2  vlshwdaqvs qqfrvqpnck yvlrvtaekv gggdgyvtir ddahhtetlt
  cry9da1  VLSHWDAQVS QQLRVNPNCK YVLRVTARKV GGGDGYVTIR DGAHHQETLT
  cry9da2  ~~~~~~~~~~ ~~~~~~~~~~ ~~~~~~~~~~ ~~~~~~~~~~ ~~~~~~~~~~
cry9d_rv1  ~~~~~~~~~~ ~~~~~~~~~~ ~~~~~~~~~~ ~~~~~~~~~~ ~~~~~~~~~~
cry9_like  ~~~~~~~~~~ ~~~~~~~~~~ ~~~~~~~~~~ ~~~~~~~~~~ ~~~~~~~~~~
  cry9_rv1 ~~~~~~~~~~ ~~~~~~~~~~ ~~~~~~~~~~ ~~~~~~~~~~ ~~~~~~~~~~
  cry9eb1  VLSHWDAQVS QQFRVQPNCK YVLRVTAEKV GGGDGYVTIR DGAHHTETLT
   cry9fa  ~~~~~~~~~~ ~~~~~~~~~~ ~~~~~~~~~~ ~~~~~~~~~~ ~~~~~~~~~~
  cry9ea1  VLSHWDAQVS QQFRVQPNCK YVLRVTAKKV GNGDGYVTIQ DGAHHRETLT
  cry9ea2  vlshwdaqvs qqfrvqpnck yvlrvtakkv gngdgyvtiq dgahhretlt
  cry9ca1  VLSHWDAQVS QQLRVNPNCK YVLRVTARKV GGGDGYVTIR DGAHHQETLT
  cry9ba1  VLSHWDAQVS QQFRVQPNCK YVLRVTAEKV GGGDGYVTIR DGAHHTETLT
Consensus  VLSHWDAQVS QQFRVQPNCK YVLRVTAEKV GGGDGYVTIR DGAHHTETLT

           1151                                                     1200
  cry9aa1  FNACDYDING TYVTDNTYLT KEVVFHPETQ HMWVEVNETE GAFHIDSIEF VETEK
  cry9aa2  fnacdyding tyvtdntylt kevvfhpetq hmwvevnete gafhidsief ~~~~~
  cry9da1  FNACDYDVNG TYVNDNSYIT EEVVFYPETK HMWVEVSESE GSFYIDSIEF IETQE
  cry9da2  ~~~~~~~~~~ ~~~~~~~~~~ ~~~~~~~~~~ ~~~~~~~~~~ ~~~~~~~~~~ ~~~~~
cry9d_rv1  ~~~~~~~~~~ ~~~~~~~~~~ ~~~~~~~~~~ ~~~~~~~~~~ ~~~~~~~~~~ ~~~~~
cry9_like  ~~~~~~~~~~ ~~~~~~~~~~ ~~~~~~~~~~ ~~~~~~~~~~ ~~~~~~~~~~ ~~~~~
  cry9_rv1 ~~~~~~~~~~ ~~~~~~~~~~ ~~~~~~~~~~ ~~~~~~~~~~ ~~~~~~~~~~ ~~~~~
  cry9eb1  FNACDYDING TYVTDNTYLT KEVIFYSHTE HMWVEVNETE GAFHIDSIEF VETEK
   cry9fa  ~~~~~~~~~~ ~~~~~~~~~~ ~~~~~~~~~~ ~~~~~~~~~~ ~~~~~~~~~~ ~~~~~
  cry9ea1  FNACDYDVNG THVNDNSYIT KELVFYPKTE HMWVEVSETE GTFYIDSIEF IETQE
  cry9ea2  fnacdydvng thvndnsyit kelvfypkte hmwvevsete gtfyidsief ietqe
  cry9ca1  FNACDYDVNG TYVNDNSYIT EEVVFYPETK HMWVEVSESE GSFYIDSIEF IETQE
  cry9ba1  FNACDYDING TYVTDNTYLT KEVIFYSHTE HMWVEVNETE GAFHIDSIEF VETEK
Consensus  FNACDYD-NG TYV-DN-Y-T KEVVFYPETE HMWVEV-ETE GAF-IDSIEF IETQE
```

FIGURE 1H

```
Endotoxin_N: domain 1 of 1, from 70 to 296: score 447.4, E = 1.6e-131
                   *->vqiglsivgtlLgalGvfPggGflvgfystLldlLWPsngpsnenvW
      query    70     IQVGINIVGRLLSFFGF-PFSSQWVTVYTYLLNSLWPDDENS---VW 112

                   eaFleqvEqLIdQrIseyvrnrAiarLeGLgnsydteViYleaLeeWekn
      query   113 DAFMKRIEELIDQKISEAVKGRALDELTGLQDNYN---LYVEALDEWLNR 159

                   pnnarsreaVrtrFnildslfvnaipsFavsagysenyevlLLPvYAQAA
      query   160 PNGAR-ASLVSQRFNILDSLFTQFMPSFGSGPGS-QNYSTILLPVYAQAA 207

                   NLHLlLLRDAvifGerWgltqadinstldednyYnrllerikeYtdHCvn
      query   208 NLHLLLLKDADIYGARWGLNQTQID------QFHSRQQSLTRTYTNHCVT 251

                   wYNtGLnnlrgtnldaesWvrYNryRReMTLtVLDlVAlFPnYDprl<-*        (SEQ ID NO:32)
      query   252 TYNDGLAELRGTS--VESWLKYHQYRREMTVTAMDLVALFPYYNVRQ    296    (SEQ ID NO:35)

Endotoxin_M: domain 1 of 1, from 301 to 523: score 189.3, E = 8.2e-54
                   *->tksqLTREiYTDPvgevspgsglseglcrrWginnypr...ltFsal
      query   301     ANPQLTREVYTDPIVFNPPEPP--SGAFCESFYNIRAArerLTFSQL 345

                   EnaliRsPHLfdfLnsltiyTnssrgplnttldinyWsGhrvtssytggs
      query   346 ENAIIRPPRLFERFQALGIYTGEARLNQNSAP-TNYWIGHFIRNTRLGD- 393

                   tlnniissplyGnttntaeppvtispcftnndiYRtlsatsnrlsgnnii
      query   394 ---STTITTNYGTTNN--RLTNFIPP--TTSDVYQINSISSNLAS----- 431

                   glnnpingvtrvdFygangtnseissntyrsskrgnggqrtidsideLPp
      query   432 -ALSTLFGVTRAQFHYGSGIIWSYVGQNNVLP---QCHQ-NYNSIEELPN 476

                   ettnePiyesYSHrLShvtflrsnttqggsdatr.ahvpvFsWTHrSad<        (SEQ ID NO:33)
      query   477 QS-DEPTVRSYSHRLSHITSFNF-SVQLNNPVISlGNMPVYVWTHRSVD  523    (SEQ ID NO:36)


Endotoxin_C: domain 1 of 1, from 533 to 670: score 263.8, E = 3e-76
                   *->ITQIPlVKaynlssgasVVkGPGFTGGDilrrtssnGsfgtlrvttk
      query   533     ITQLPAVKASTLGAGAIVVKGPGFTGGDVIRRTS-VGDFGTIRVS-- 576

                   linnplsqrYRiRIRYASttnlrfivsliggttsnqfnfpkTmnrgdnye
      query   577 -VTGSLTQQYRIRFRYASTIDFDFFVI-RGGTTINNFRFTHTMSSG---E 621
```

FIGURE 3-1

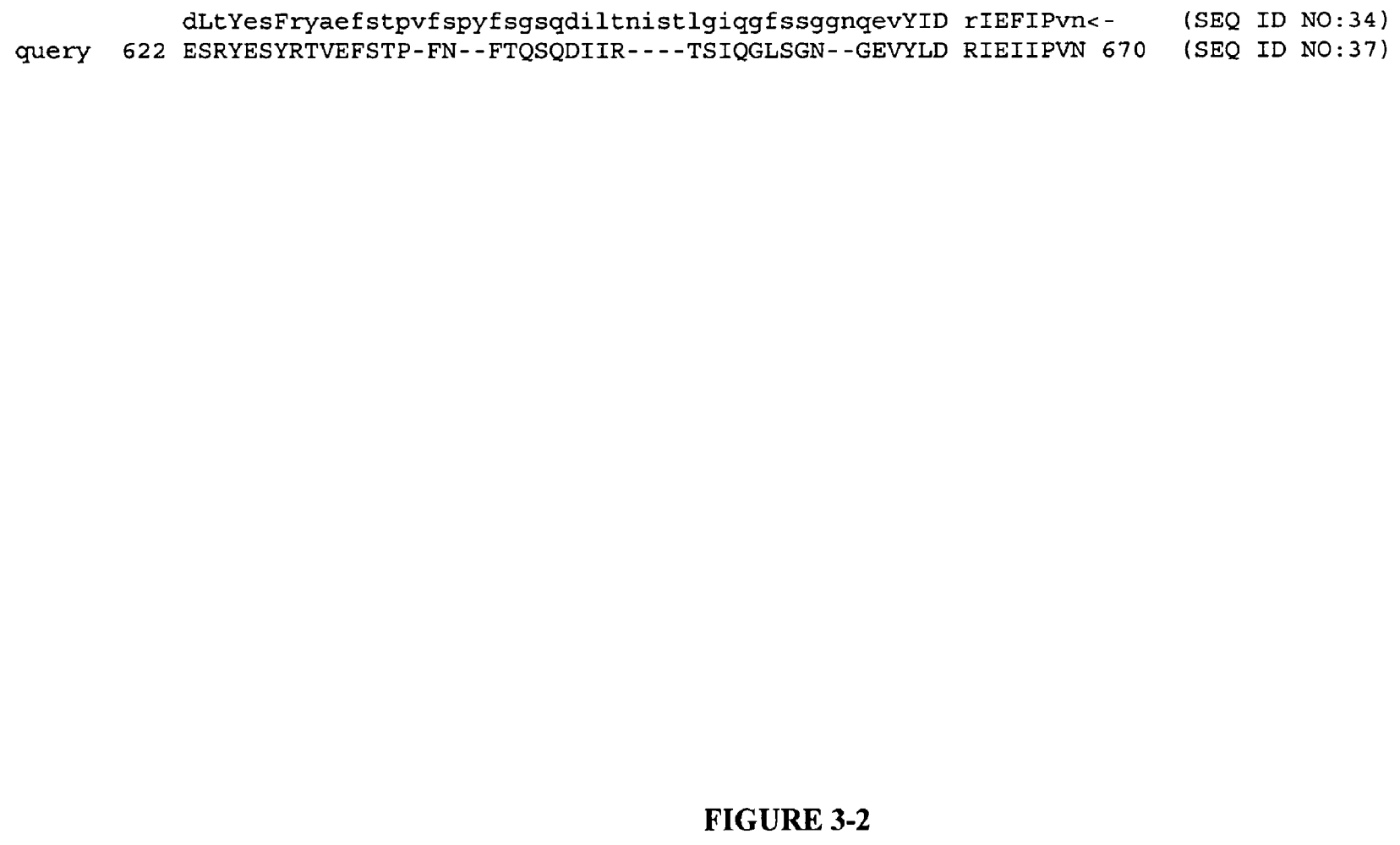

```
                dLtYesFryaefstpvfspyfsgsqdiltnistlgiqgfssggnqevYID rIEFIPvn<-     (SEQ ID NO:34)
query   622 ESRYESYRTVEFSTP-FN--FTQSQDIIR----TSIQGLSGN--GEVYLD RIEIIPVN 670   (SEQ ID NO:37)
```

FIGURE 3-2

SEQUENCE LISTING

<160> NUMBER OF SEQ ID NOS: 38

<210> SEQ ID NO 1
<211> LENGTH: 1841
<212> TYPE: DNA
<213> ORGANISM: Bacillus thuringiensis
<220> FEATURE:
<221> NAME/KEY: CDS
<222> LOCATION: (1)...(1841)

<400> SEQUENCE: 1 gat gta cta caa aca ggt att act att gta gga aga gta cta ggg ttt 48
Asp Val Leu Gln Thr Gly Ile Thr Ile Val Gly Arg Val Leu Gly Phe
1 5 10 15 tta ggt gtt cca ttt gct ggc caa tta gtt act ttc tat acg ttt ctc 96
Leu Gly Val Pro Phe Ala Gly Gln Leu Val Thr Phe Tyr Thr Phe Leu
20 25 30 tta aat cag ttg tgg cca act aat aat aat gca gta tgg gaa gct ttt 144
Leu Asn Gln Leu Trp Pro Thr Asn Asn Asn Ala Val Trp Glu Ala Phe
35 40 45 atg gca caa gta gaa gag ctt atc gac caa aga ata tcg gat caa gta 192
Met Ala Gln Val Glu Glu Leu Ile Asp Gln Arg Ile Ser Asp Gln Val
50 55 60 gta aga aat gca ctt gat gac cta act gga tta cac gat tat tat aat 240
Val Arg Asn Ala Leu Asp Asp Leu Thr Gly Leu His Asp Tyr Tyr Asn
65 70 75 80 gaa tat cta gcg gca tta gag gag tgg cta gat aga ccg aat ggc gcc 288
Glu Tyr Leu Ala Ala Leu Glu Glu Trp Leu Asp Arg Pro Asn Gly Ala
85 90 95 aga gct aac tta gct ttt caa agg ttt gaa aac ctg cat acc gca ttt 336
Arg Ala Asn Leu Ala Phe Gln Arg Phe Glu Asn Leu His Thr Ala Phe
100 105 110 gta act aga atg cca agt ttt gga act ggt cct ggt agt caa aga gat 384
Val Thr Arg Met Pro Ser Phe Gly Thr Gly Pro Gly Ser Gln Arg Asp
115 120 125 gcg gta gca ttg ctg acg gta tat gca caa gca gcg aat ctc cat ttg 432
Ala Val Ala Leu Leu Thr Val Tyr Ala Gln Ala Ala Asn Leu His Leu
130 135 140 tta tta tta aaa gat gca gaa att tat ggg gca aga tgg gga ctt caa 480
Leu Leu Leu Lys Asp Ala Glu Ile Tyr Gly Ala Arg Trp Gly Leu Gln
145 150 155 160 caa agt cag att aac tta tat ttt aat gct caa caa gat cgt act cga 528
Gln Ser Gln Ile Asn Leu Tyr Phe Asn Ala Gln Gln Asp Arg Thr Arg
165 170 175 att tat acc aat cat tgt gtg gca aca tat aat aga gga tta gaa gat 576
Ile Tyr Thr Asn His Cys Val Ala Thr Tyr Asn Arg Gly Leu Glu Asp
180 185 190 tta aaa ggc aca aat acg gaa agt tgg tat aat tat cat caa ttc cgt 624
Leu Lys Gly Thr Asn Thr Glu Ser Trp Tyr Asn Tyr His Gln Phe Arg
195 200 205 aga gag atg aca tta atg gca atg gat tta gta gcg tta ttc cca tat 672
Arg Glu Met Thr Leu Met Ala Met Asp Leu Val Ala Leu Phe Pro Tyr
210 215 220 tac aat gta cga caa tat cca aat ggg gca aat cct cag ctt aca cgt 720
Tyr Asn Val Arg Gln Tyr Pro Asn Gly Ala Asn Pro Gln Leu Thr Arg
225 230 235 240 gaa ata tat aca gat cca gtt gta ttt aat cca cca gcc aat cag gga 768
Glu Ile Tyr Thr Asp Pro Val Val Phe Asn Pro Pro Ala Asn Gln Gly
245 250 255

-continued

```
ctt tgt aga cgt tgg gga aat aac cct tat atg aca ttt tcg gga ctt      816
Leu Cys Arg Arg Trp Gly Asn Asn Pro Tyr Met Thr Phe Ser Gly Leu
            260                 265                 270

gag aat gct ttc att cgc cct ccg cat ctt ttt gat aga ttg aat agc      864
Glu Asn Ala Phe Ile Arg Pro Pro His Leu Phe Asp Arg Leu Asn Ser
        275                 280                 285

tta aca att aac agc cat cga ttt ccc att tca tca aat ttt atg gat      912
Leu Thr Ile Asn Ser His Arg Phe Pro Ile Ser Ser Asn Phe Met Asp
    290                 295                 300

tat tgg gca gga cat acg tta cgc cgt agt tat atg aat aat tcg gca      960
Tyr Trp Ala Gly His Thr Leu Arg Arg Ser Tyr Met Asn Asn Ser Ala
305                 310                 315                 320

gta caa gaa gat agt tat ggc gcg atc act ccc aca aga gtc aca att     1008
Val Gln Glu Asp Ser Tyr Gly Ala Ile Thr Pro Thr Arg Val Thr Ile
                325                 330                 335

aat ccc gga gtt aat gga aca aac cac ata gag tca acg gca gta gat     1056
Asn Pro Gly Val Asn Gly Thr Asn His Ile Glu Ser Thr Ala Val Asp
            340                 345                 350

ttt cgt tct ggt ctg gtg ggt ata tat ggc gtg cat aga gct tcg ttt     1104
Phe Arg Ser Gly Leu Val Gly Ile Tyr Gly Val His Arg Ala Ser Phe
        355                 360                 365

gtc ccg ggc ggc tta ttt aat ggt acc att tct cct gct aat gca ggg     1152
Val Pro Gly Gly Leu Phe Asn Gly Thr Ile Ser Pro Ala Asn Ala Gly
    370                 375                 380

tgt aga aat ctg cat gat aca aga gac gta tta cca ttg gaa gaa aat     1200
Cys Arg Asn Leu His Asp Thr Arg Asp Val Leu Pro Leu Glu Glu Asn
385                 390                 395                 400

aac gga agc cct tcc cat aga tta tct cat gtt act ttt ttt aag ttt     1248
Asn Gly Ser Pro Ser His Arg Leu Ser His Val Thr Phe Phe Lys Phe
                405                 410                 415

tca act aat cag gct ggg tct ctt gca aat ggt gga agc gta cct tta     1296
Ser Thr Asn Gln Ala Gly Ser Leu Ala Asn Gly Gly Ser Val Pro Leu
            420                 425                 430

tat gtt tgg gca cgt caa gat ata gat ttt aat aac aca att acc gca     1344
Tyr Val Trp Ala Arg Gln Asp Ile Asp Phe Asn Asn Thr Ile Thr Ala
        435                 440                 445

aat aga att aca caa cta cca ttg gta aag gca ttt gaa ata gct gcg     1392
Asn Arg Ile Thr Gln Leu Pro Leu Val Lys Ala Phe Glu Ile Ala Ala
    450                 455                 460

ggt act act atc gta aaa gga cca gga ttt aca gga ggg gat ata ctt     1440
Gly Thr Thr Ile Val Lys Gly Pro Gly Phe Thr Gly Gly Asp Ile Leu
465                 470                 475                 480

cga aga acg agc act ggt act tta gga aca ata aga gta aat gtt aat     1488
Arg Arg Thr Ser Thr Gly Thr Leu Gly Thr Ile Arg Val Asn Val Asn
                485                 490                 495

tca ccg tta acg caa cga tat cgc gta aga ttc cgt tat gct tcg aca     1536
Ser Pro Leu Thr Gln Arg Tyr Arg Val Arg Phe Arg Tyr Ala Ser Thr
            500                 505                 510

gta gat ttt gat ttc ttt gta tca cgt gga ggg act act gta aat aat     1584
Val Asp Phe Asp Phe Phe Val Ser Arg Gly Gly Thr Thr Val Asn Asn
        515                 520                 525

ttt aga ttc cca cgt aca atg agc aga ggt cag gaa tca aga tac gaa     1632
Phe Arg Phe Pro Arg Thr Met Ser Arg Gly Gln Glu Ser Arg Tyr Glu
    530                 535                 540

tcc tat gtc aca agt gag ttt acg act cct ttt acc ttt aca caa agt     1680
Ser Tyr Val Thr Ser Glu Phe Thr Thr Pro Phe Thr Phe Thr Gln Ser
545                 550                 555                 560

caa gat ttt att cga acg tct atc caa gga ctt agt ggg aat gga gaa     1728
Gln Asp Phe Ile Arg Thr Ser Ile Gln Gly Leu Ser Gly Asn Gly Glu
                565                 570                 575
```

-continued

```
gtg tat ctt gat aga att gaa atc atc cca gtt aac ccg gca cga gaa      1776
Val Tyr Leu Asp Arg Ile Glu Ile Ile Pro Val Asn Pro Ala Arg Glu
            580                 585                 590

gcg gag gag gat tta gaa gcg gcg aag aaa gcg gtg gcg agc ttg ttt      1824
Ala Glu Glu Asp Leu Glu Ala Ala Lys Lys Ala Val Ala Ser Leu Phe
        595                 600                 605

aca cgt aca agg gat gg                                               1841
Thr Arg Thr Arg Asp
    610


<210> SEQ ID NO 2
<211> LENGTH: 613
<212> TYPE: PRT
<213> ORGANISM: Bacillus thuringiensis

<400> SEQUENCE: 2

Asp Val Leu Gln Thr Gly Ile Thr Ile Val Gly Arg Val Leu Gly Phe
 1               5                  10                  15

Leu Gly Val Pro Phe Ala Gly Gln Leu Val Thr Phe Tyr Thr Phe Leu
            20                  25                  30

Leu Asn Gln Leu Trp Pro Thr Asn Asn Asn Ala Val Trp Glu Ala Phe
        35                  40                  45

Met Ala Gln Val Glu Glu Leu Ile Asp Gln Arg Ile Ser Asp Gln Val
    50                  55                  60

Val Arg Asn Ala Leu Asp Asp Leu Thr Gly Leu His Asp Tyr Tyr Asn
65                  70                  75                  80

Glu Tyr Leu Ala Ala Leu Glu Glu Trp Leu Asp Arg Pro Asn Gly Ala
                85                  90                  95

Arg Ala Asn Leu Ala Phe Gln Arg Phe Glu Asn Leu His Thr Ala Phe
            100                 105                 110

Val Thr Arg Met Pro Ser Phe Gly Thr Gly Pro Gly Ser Gln Arg Asp
        115                 120                 125

Ala Val Ala Leu Leu Thr Val Tyr Ala Gln Ala Ala Asn Leu His Leu
    130                 135                 140

Leu Leu Leu Lys Asp Ala Glu Ile Tyr Gly Ala Arg Trp Gly Leu Gln
145                 150                 155                 160

Gln Ser Gln Ile Asn Leu Tyr Phe Asn Ala Gln Gln Asp Arg Thr Arg
                165                 170                 175

Ile Tyr Thr Asn His Cys Val Ala Thr Tyr Asn Arg Gly Leu Glu Asp
            180                 185                 190

Leu Lys Gly Thr Asn Thr Glu Ser Trp Tyr Asn Tyr His Gln Phe Arg
        195                 200                 205

Arg Glu Met Thr Leu Met Ala Met Asp Leu Val Ala Leu Phe Pro Tyr
    210                 215                 220

Tyr Asn Val Arg Gln Tyr Pro Asn Gly Ala Asn Pro Gln Leu Thr Arg
225                 230                 235                 240

Glu Ile Tyr Thr Asp Pro Val Val Phe Asn Pro Pro Ala Asn Gln Gly
                245                 250                 255

Leu Cys Arg Arg Trp Gly Asn Asn Pro Tyr Met Thr Phe Ser Gly Leu
            260                 265                 270

Glu Asn Ala Phe Ile Arg Pro Pro His Leu Phe Asp Arg Leu Asn Ser
        275                 280                 285

Leu Thr Ile Asn Ser His Arg Phe Pro Ile Ser Ser Asn Phe Met Asp
    290                 295                 300

Tyr Trp Ala Gly His Thr Leu Arg Arg Ser Tyr Met Asn Asn Ser Ala
```

-continued 305 310 315 320

Val Gln Glu Asp Ser Tyr Gly Ala Ile Thr Pro Thr Arg Val Thr Ile
325 330 335

Asn Pro Gly Val Asn Gly Thr Asn His Ile Glu Ser Thr Ala Val Asp
340 345 350

Phe Arg Ser Gly Leu Val Gly Ile Tyr Gly Val His Arg Ala Ser Phe
355 360 365

Val Pro Gly Gly Leu Phe Asn Gly Thr Ile Ser Pro Ala Asn Ala Gly
370 375 380

Cys Arg Asn Leu His Asp Thr Arg Asp Val Leu Pro Leu Glu Glu Asn
385 390 395 400

Asn Gly Ser Pro Ser His Arg Leu Ser His Val Thr Phe Phe Lys Phe
405 410 415

Ser Thr Asn Gln Ala Gly Ser Leu Ala Asn Gly Gly Ser Val Pro Leu
420 425 430

Tyr Val Trp Ala Arg Gln Asp Ile Asp Phe Asn Asn Thr Ile Thr Ala
435 440 445

Asn Arg Ile Thr Gln Leu Pro Leu Val Lys Ala Phe Glu Ile Ala Ala
450 455 460

Gly Thr Thr Ile Val Lys Gly Pro Gly Phe Thr Gly Gly Asp Ile Leu
465 470 475 480

Arg Arg Thr Ser Thr Gly Thr Leu Gly Thr Ile Arg Val Asn Val Asn
485 490 495

Ser Pro Leu Thr Gln Arg Tyr Arg Val Arg Phe Arg Tyr Ala Ser Thr
500 505 510

Val Asp Phe Asp Phe Phe Val Ser Arg Gly Gly Thr Thr Val Asn Asn
515 520 525

Phe Arg Phe Pro Arg Thr Met Ser Arg Gly Gln Glu Ser Arg Tyr Glu
530 535 540

Ser Tyr Val Thr Ser Glu Phe Thr Thr Pro Phe Thr Phe Thr Gln Ser
545 550 555 560

Gln Asp Phe Ile Arg Thr Ser Ile Gln Gly Leu Ser Gly Asn Gly Glu
565 570 575

Val Tyr Leu Asp Arg Ile Glu Ile Ile Pro Val Asn Pro Ala Arg Glu
580 585 590

Ala Glu Glu Asp Leu Glu Ala Ala Lys Lys Ala Val Ala Ser Leu Phe
595 600 605

Thr Arg Thr Arg Asp
610

<210> SEQ ID NO 3
<211> LENGTH: 2043
<212> TYPE: DNA
<213> ORGANISM: Bacillus thuringiensis
<220> FEATURE:
<221> NAME/KEY: CDS
<222> LOCATION: (1)...(2043)

<400> SEQUENCE: 3 atg aat cga aat aat caa aat gaa tat gaa att att gac gga acc aat 48
Met Asn Arg Asn Asn Gln Asn Glu Tyr Glu Ile Ile Asp Gly Thr Asn
1 5 10 15 tgt gat tgt tcg tca gat gag gtt gtg aaa tat cct tta gca agt gag 96
Cys Asp Cys Ser Ser Asp Glu Val Val Lys Tyr Pro Leu Ala Ser Glu
20 25 30 caa aat ggt gtg tta caa aat atg aac tat aaa gaa tat tta caa acg 144

-continued

```
Gln Asn Gly Val Leu Gln Asn Met Asn Tyr Lys Glu Tyr Leu Gln Thr
         35                  40                  45

tat gat gga gac tat aca ggc tct ctt atc aat cct aac tta tct att      192
Tyr Asp Gly Asp Tyr Thr Gly Ser Leu Ile Asn Pro Asn Leu Ser Ile
     50                  55                  60

aat act aga gat gta cta caa act ggt att act att gta gga aga gta      240
Asn Thr Arg Asp Val Leu Gln Thr Gly Ile Thr Ile Val Gly Arg Val
 65                  70                  75                  80

cta ggg ttt tta ggt gtt cca ttt gct ggc caa tta gtt act ttc tat      288
Leu Gly Phe Leu Gly Val Pro Phe Ala Gly Gln Leu Val Thr Phe Tyr
                 85                  90                  95

acg ttt ctc tta aat cag ttg tgg cca act aat aat aat gca gta tgg      336
Thr Phe Leu Leu Asn Gln Leu Trp Pro Thr Asn Asn Asn Ala Val Trp
            100                 105                 110

gaa gct ttt atg gca caa gta gaa gag ctt atc gac caa aga ata tcg      384
Glu Ala Phe Met Ala Gln Val Glu Glu Leu Ile Asp Gln Arg Ile Ser
        115                 120                 125

gat caa gta gta aga aat gca ctt gat gac cta act gga tta cac gat      432
Asp Gln Val Val Arg Asn Ala Leu Asp Asp Leu Thr Gly Leu His Asp
    130                 135                 140

tat tat aat gaa tat cta gcg gca tta gag gag tgg cta gat aga ccg      480
Tyr Tyr Asn Glu Tyr Leu Ala Ala Leu Glu Glu Trp Leu Asp Arg Pro
145                 150                 155                 160

aat ggc gcc aga gct aac tta gct ttt caa agg ttt gaa aac ctg cat      528
Asn Gly Ala Arg Ala Asn Leu Ala Phe Gln Arg Phe Glu Asn Leu His
                165                 170                 175

acc gca ttt gta act aga atg cca agt ttt gga act ggt cct ggt agt      576
Thr Ala Phe Val Thr Arg Met Pro Ser Phe Gly Thr Gly Pro Gly Ser
            180                 185                 190

caa aga gat gcg gta gca ttg ctg acg gta tat gca caa gca gcg aat      624
Gln Arg Asp Ala Val Ala Leu Leu Thr Val Tyr Ala Gln Ala Ala Asn
        195                 200                 205

ctc cat ttg tta tta tta aaa gat gca gaa att tat ggg gca aga tgg      672
Leu His Leu Leu Leu Leu Lys Asp Ala Glu Ile Tyr Gly Ala Arg Trp
    210                 215                 220

gga ctt caa caa agt cag att aac tta tat ttt aat gct caa caa gat      720
Gly Leu Gln Gln Ser Gln Ile Asn Leu Tyr Phe Asn Ala Gln Gln Asp
225                 230                 235                 240

cgt act cga att tat acc aat cat tgt gtg gca aca tat aat aga gga      768
Arg Thr Arg Ile Tyr Thr Asn His Cys Val Ala Thr Tyr Asn Arg Gly
                245                 250                 255

tta gaa gat tta aaa ggc aca aat acg gaa agt tgg tat aat tat cat      816
Leu Glu Asp Leu Lys Gly Thr Asn Thr Glu Ser Trp Tyr Asn Tyr His
            260                 265                 270

caa ttc cgt aga gag atg aca tta atg gca atg gat tta gta gcg tta      864
Gln Phe Arg Arg Glu Met Thr Leu Met Ala Met Asp Leu Val Ala Leu
        275                 280                 285

ttc cca tat tac aat gta cga caa tat cca aat ggg gca aat cct cag      912
Phe Pro Tyr Tyr Asn Val Arg Gln Tyr Pro Asn Gly Ala Asn Pro Gln
    290                 295                 300

ctt aca cgt gaa ata tat aca gat cca gtt gta ttt aat cca cca gcc      960
Leu Thr Arg Glu Ile Tyr Thr Asp Pro Val Val Phe Asn Pro Pro Ala
305                 310                 315                 320

aat cag gga ctt tgt aga cgt tgg gga aat aac cct tat atg aca ttt     1008
Asn Gln Gly Leu Cys Arg Arg Trp Gly Asn Asn Pro Tyr Met Thr Phe
                325                 330                 335

tcg gga ctt gag aat gct ttc att cgc cct ccg cat ctt ttt gat aga     1056
Ser Gly Leu Glu Asn Ala Phe Ile Arg Pro Pro His Leu Phe Asp Arg
            340                 345                 350
```

-continued

```
ttg aat agc tta aca att aac agc cat cga ttt ccc att tca tca aat      1104
Leu Asn Ser Leu Thr Ile Asn Ser His Arg Phe Pro Ile Ser Ser Asn
        355                 360                 365

ttt atg gat tat tgg gca gga cat acg tta cgc cgt agt tat atg aat      1152
Phe Met Asp Tyr Trp Ala Gly His Thr Leu Arg Arg Ser Tyr Met Asn
    370                 375                 380

aat tcg gca gta caa gaa gat agt tat ggc gcg atc act ccc aca aga      1200
Asn Ser Ala Val Gln Glu Asp Ser Tyr Gly Ala Ile Thr Pro Thr Arg
385                 390                 395                 400

gtc aca att aat ccc gga gtt aat gga aca aac cac ata gag tca acg      1248
Val Thr Ile Asn Pro Gly Val Asn Gly Thr Asn His Ile Glu Ser Thr
                405                 410                 415

gca gta gat ttt cgt tct ggt ctg gtg ggt ata tat ggc gtg cat aga      1296
Ala Val Asp Phe Arg Ser Gly Leu Val Gly Ile Tyr Gly Val His Arg
            420                 425                 430

gct tcg ttt gtc ccg ggc ggc tta ttt aat ggt acc att tct cct gct      1344
Ala Ser Phe Val Pro Gly Gly Leu Phe Asn Gly Thr Ile Ser Pro Ala
        435                 440                 445

aat gca ggg tgt aga aat ctg cat gat aca aga gac gta tta cca ttg      1392
Asn Ala Gly Cys Arg Asn Leu His Asp Thr Arg Asp Val Leu Pro Leu
    450                 455                 460

gaa gaa aat aac gga agc cct tcc cat aga tta tct cat gtt act ttt      1440
Glu Glu Asn Asn Gly Ser Pro Ser His Arg Leu Ser His Val Thr Phe
465                 470                 475                 480

tta agt ttt caa act aat cag gct ggg tct ctt gca aat ggt gga agc      1488
Leu Ser Phe Gln Thr Asn Gln Ala Gly Ser Leu Ala Asn Gly Gly Ser
                485                 490                 495

gta cct tta tat gtt tgg gca cgt caa gat ata gat ttt aat aac aca      1536
Val Pro Leu Tyr Val Trp Ala Arg Gln Asp Ile Asp Phe Asn Asn Thr
            500                 505                 510

att acc gca aat aga att aca caa cta cca ttg gta aag gca ttt gaa      1584
Ile Thr Ala Asn Arg Ile Thr Gln Leu Pro Leu Val Lys Ala Phe Glu
        515                 520                 525

ata gct gcg ggt act act atc gta aaa gga cca gga ttt aca gga ggg      1632
Ile Ala Ala Gly Thr Thr Ile Val Lys Gly Pro Gly Phe Thr Gly Gly
    530                 535                 540

gat ata ctt cga aga acg agc act ggt act tta gga aca ata aga gta      1680
Asp Ile Leu Arg Arg Thr Ser Thr Gly Thr Leu Gly Thr Ile Arg Val
545                 550                 555                 560

aat gtt aat tca ccg tta acg caa cga tat cgc gta aga ttc cgt tat      1728
Asn Val Asn Ser Pro Leu Thr Gln Arg Tyr Arg Val Arg Phe Arg Tyr
                565                 570                 575

gct tcg aca gta gat ttt gat ttc ttt gta tca cgt gga ggg act act      1776
Ala Ser Thr Val Asp Phe Asp Phe Phe Val Ser Arg Gly Gly Thr Thr
            580                 585                 590

gta aat aat ttt aga ttc cca cgt aca atg agc aga ggt cag gaa tca      1824
Val Asn Asn Phe Arg Phe Pro Arg Thr Met Ser Arg Gly Gln Glu Ser
        595                 600                 605

aga tac gaa tcc tat gtc aca agt gag ttt acg act cct ttt acc ttt      1872
Arg Tyr Glu Ser Tyr Val Thr Ser Glu Phe Thr Thr Pro Phe Thr Phe
    610                 615                 620

aca caa agt caa gat ttt att cga acg tct atc caa gga ctt agt ggg      1920
Thr Gln Ser Gln Asp Phe Ile Arg Thr Ser Ile Gln Gly Leu Ser Gly
625                 630                 635                 640

aat gga gaa gtg tat ctt gat aga att gaa atc atc cca gtt aac ccg      1968
Asn Gly Glu Val Tyr Leu Asp Arg Ile Glu Ile Ile Pro Val Asn Pro
                645                 650                 655

gca cga gaa gcg gag gag gat tta gaa gcg gcg aag aaa gcg gtg gcg      2016
Ala Arg Glu Ala Glu Glu Asp Leu Glu Ala Ala Lys Lys Ala Val Ala
            660                 665                 670
```

```
agc ttg ttt aca cgt aca agg gac gga                                 2043
Ser Leu Phe Thr Arg Thr Arg Asp Gly
        675                 680


<210> SEQ ID NO 4
<211> LENGTH: 681
<212> TYPE: PRT
<213> ORGANISM: Bacillus thuringiensis

<400> SEQUENCE: 4

Met Asn Arg Asn Asn Gln Asn Glu Tyr Glu Ile Ile Asp Gly Thr Asn
 1               5                  10                  15

Cys Asp Cys Ser Ser Asp Glu Val Val Lys Tyr Pro Leu Ala Ser Glu
            20                  25                  30

Gln Asn Gly Val Leu Gln Asn Met Asn Tyr Lys Glu Tyr Leu Gln Thr
        35                  40                  45

Tyr Asp Gly Asp Tyr Thr Gly Ser Leu Ile Asn Pro Asn Leu Ser Ile
    50                  55                  60

Asn Thr Arg Asp Val Leu Gln Thr Gly Ile Thr Ile Val Gly Arg Val
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asn Asn Ala Val Trp
            100                 105                 110

Glu Ala Phe Met Ala Gln Val Glu Glu Leu Ile Asp Gln Arg Ile Ser
        115                 120                 125

Asp Gln Val Val Arg Asn Ala Leu Asp Asp Leu Thr Gly Leu His Asp
    130                 135                 140

Tyr Tyr Asn Glu Tyr Leu Ala Ala Leu Glu Glu Trp Leu Asp Arg Pro
145                 150                 155                 160

Asn Gly Ala Arg Ala Asn Leu Ala Phe Gln Arg Phe Glu Asn Leu His
                165                 170                 175

Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Gln Gln Ser Gln Ile Asn Leu Tyr Phe Asn Ala Gln Gln Asp
225                 230                 235                 240

Arg Thr Arg Ile Tyr Thr Asn His Cys Val Ala Thr Tyr Asn Arg Gly
                245                 250                 255

Leu Glu Asp Leu Lys Gly Thr Asn Thr Glu Ser Trp Tyr Asn Tyr His
            260                 265                 270

Gln Phe Arg Arg Glu Met Thr Leu Met Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Ile Tyr Thr Asp Pro Val Val Phe Asn Pro Pro Ala
305                 310                 315                 320

Asn Gln Gly Leu Cys Arg Arg Trp Gly Asn Asn Pro Tyr Met Thr Phe
                325                 330                 335

Ser Gly Leu Glu Asn Ala Phe Ile Arg Pro Pro His Leu Phe Asp Arg
            340                 345                 350
```

-continued

```
Leu Asn Ser Leu Thr Ile Asn Ser His Arg Phe Pro Ile Ser Ser Asn
        355                 360                 365

Phe Met Asp Tyr Trp Ala Gly His Thr Leu Arg Arg Ser Tyr Met Asn
    370                 375                 380

Asn Ser Ala Val Gln Glu Asp Ser Tyr Gly Ala Ile Thr Pro Thr Arg
385                 390                 395                 400

Val Thr Ile Asn Pro Gly Val Asn Gly Thr Asn His Ile Glu Ser Thr
                405                 410                 415

Ala Val Asp Phe Arg Ser Gly Leu Val Gly Ile Tyr Gly Val His Arg
            420                 425                 430

Ala Ser Phe Val Pro Gly Gly Leu Phe Asn Gly Thr Ile Ser Pro Ala
        435                 440                 445

Asn Ala Gly Cys Arg Asn Leu His Asp Thr Arg Asp Val Leu Pro Leu
    450                 455                 460

Glu Glu Asn Asn Gly Ser Pro Ser His Arg Leu Ser His Val Thr Phe
465                 470                 475                 480

Leu Ser Phe Gln Thr Asn Gln Ala Gly Ser Leu Ala Asn Gly Gly Ser
                485                 490                 495

Val Pro Leu Tyr Val Trp Ala Arg Gln Asp Ile Asp Phe Asn Asn Thr
            500                 505                 510

Ile Thr Ala Asn Arg Ile Thr Gln Leu Pro Leu Val Lys Ala Phe Glu
        515                 520                 525

Ile Ala Ala Gly Thr Thr Ile Val Lys Gly Pro Gly Phe Thr Gly Gly
    530                 535                 540

Asp Ile Leu Arg Arg Thr Ser Thr Gly Thr Leu Gly Thr Ile Arg Val
545                 550                 555                 560

Asn Val Asn Ser Pro Leu Thr Gln Arg Tyr Arg Val Arg Phe Arg Tyr
                565                 570                 575

Ala Ser Thr Val Asp Phe Asp Phe Phe Val Ser Arg Gly Gly Thr Thr
            580                 585                 590

Val Asn Asn Phe Arg Phe Pro Arg Thr Met Ser Arg Gly Gln Glu Ser
        595                 600                 605

Arg Tyr Glu Ser Tyr Val Thr Ser Glu Phe Thr Thr Pro Phe Thr Phe
    610                 615                 620

Thr Gln Ser Gln Asp Phe Ile Arg Thr Ser Ile Gln Gly Leu Ser Gly
625                 630                 635                 640

Asn Gly Glu Val Tyr Leu Asp Arg Ile Glu Ile Ile Pro Val Asn Pro
                645                 650                 655

Ala Arg Glu Ala Glu Glu Asp Leu Glu Ala Ala Lys Lys Ala Val Ala
            660                 665                 670

Ser Leu Phe Thr Arg Thr Arg Asp Gly
        675                 680


<210> SEQ ID NO 5
<211> LENGTH: 2088
<212> TYPE: DNA
<213> ORGANISM: Bacillus thuringiensis
<220> FEATURE:
<221> NAME/KEY: CDS
<222> LOCATION: (1)...(2088)

<400> SEQUENCE: 5

atg aat cga aat aat caa aat gaa tat gaa att att gat gcc cct cat       48
Met Asn Arg Asn Asn Gln Asn Glu Tyr Glu Ile Ile Asp Ala Pro His
 1               5                  10                  15

tgt gga tgt ccg tca gat gat gtt gtg aaa tat cct ttg aca gat gat       96
```

-continued

```
Cys Gly Cys Pro Ser Asp Asp Val Val Lys Tyr Pro Leu Thr Asp Asp
                20                  25                  30

ccg aat gct gga ttg caa aat atg aac tat aag gaa tat tta caa atg      144
Pro Asn Ala Gly Leu Gln Asn Met Asn Tyr Lys Glu Tyr Leu Gln Met
            35                  40                  45

tat ggt ggg gac tat aca gac cct ctt att aat cct aac tta tct gtt      192
Tyr Gly Gly Asp Tyr Thr Asp Pro Leu Ile Asn Pro Asn Leu Ser Val
    50                  55                  60

agt gga aaa gat gta ata caa gtt gga att aat att gta ggg aga tta      240
Ser Gly Lys Asp Val Ile Gln Val Gly Ile Asn Ile Val Gly Arg Leu
65                  70                  75                  80

cta agc ttt ttt gga ttc ccc ttt tct agt caa tgg gtt aca gta tat      288
Leu Ser Phe Phe Gly Phe Pro Phe Ser Ser Gln Trp Val Thr Val Tyr
                85                  90                  95

acc tat ctt tta aac agc ttg tgg ccg gat gac gag aat tct gtt tgg      336
Thr Tyr Leu Leu Asn Ser Leu Trp Pro Asp Asp Glu Asn Ser Val Trp
            100                 105                 110

gat gct ttt atg aag aga ata gaa gaa ctt att gat caa aaa atc tca      384
Asp Ala Phe Met Lys Arg Ile Glu Glu Leu Ile Asp Gln Lys Ile Ser
        115                 120                 125

gaa gca gta aag ggt aga gca ttg gat gag cta act gga tta caa gat      432
Glu Ala Val Lys Gly Arg Ala Leu Asp Glu Leu Thr Gly Leu Gln Asp
    130                 135                 140

aat tat aat tta tat gta gaa gca tta gat gag tgg ctg aat aga cca      480
Asn Tyr Asn Leu Tyr Val Glu Ala Leu Asp Glu Trp Leu Asn Arg Pro
145                 150                 155                 160

aat ggc gca agg gca tcc tta gtt tct cag cga ttt aac att tta gat      528
Asn Gly Ala Arg Ala Ser Leu Val Ser Gln Arg Phe Asn Ile Leu Asp
                165                 170                 175

agc tta ttt aca caa ttt atg cca agc ttt ggc tct ggt cct gga agt      576
Ser Leu Phe Thr Gln Phe Met Pro Ser Phe Gly Ser Gly Pro Gly Ser
            180                 185                 190

caa aat tat tca act ata tta ctt cca gta tat gca caa gca gca aac      624
Gln Asn Tyr Ser Thr Ile Leu Leu Pro Val Tyr Ala Gln Ala Ala Asn
        195                 200                 205

ctt cat ttg tta tta tta aaa gat gca gac att tat gga gct aga tgg      672
Leu His Leu Leu Leu Leu Lys Asp Ala Asp Ile Tyr Gly Ala Arg Trp
    210                 215                 220

ggg ctg aat caa act caa att gat caa ttc cat tct cgt caa caa agc      720
Gly Leu Asn Gln Thr Gln Ile Asp Gln Phe His Ser Arg Gln Gln Ser
225                 230                 235                 240

ctt act cgg act tat aca aat cat tgt gtt act acg tat aat gat gga      768
Leu Thr Arg Thr Tyr Thr Asn His Cys Val Thr Thr Tyr Asn Asp Gly
                245                 250                 255

tta gcg gaa tta aga ggc aca agc gtt gag agt tgg ctc aaa tat cat      816
Leu Ala Glu Leu Arg Gly Thr Ser Val Glu Ser Trp Leu Lys Tyr His
            260                 265                 270

caa tat cgt agg gaa atg aca gta acg gct atg gat tta gtg gca tta      864
Gln Tyr Arg Arg Glu Met Thr Val Thr Ala Met Asp Leu Val Ala Leu
        275                 280                 285

ttc cca tac tat aat gtt cga caa tat cca aat gga gca aat cca caa      912
Phe Pro Tyr Tyr Asn Val Arg Gln Tyr Pro Asn Gly Ala Asn Pro Gln
    290                 295                 300

ctt aca cgt gag gta tat aca gat cca atc gta ttt aat cca ccg gag      960
Leu Thr Arg Glu Val Tyr Thr Asp Pro Ile Val Phe Asn Pro Pro Glu
305                 310                 315                 320

cct cca agt ggc gct ttc tgc gaa agt ttt tat aat atc cga gcg gct     1008
Pro Pro Ser Gly Ala Phe Cys Glu Ser Phe Tyr Asn Ile Arg Ala Ala
                325                 330                 335
```

-continued

```
cga gaa cgc tta act ttt tcg caa ctt gaa aat gca ata att cgt cca      1056
Arg Glu Arg Leu Thr Phe Ser Gln Leu Glu Asn Ala Ile Ile Arg Pro
            340                 345                 350

ccg cgc ttg ttt gaa agg ttt caa gct tta ggg att tat aca ggc gag      1104
Pro Arg Leu Phe Glu Arg Phe Gln Ala Leu Gly Ile Tyr Thr Gly Glu
        355                 360                 365

gcg cgg ctg aat caa aat agt gct cca acg aac tat tgg att gga cat      1152
Ala Arg Leu Asn Gln Asn Ser Ala Pro Thr Asn Tyr Trp Ile Gly His
    370                 375                 380

ttt ata aga aat aca cgt tta ggg gac tca aca aca att act aca aat      1200
Phe Ile Arg Asn Thr Arg Leu Gly Asp Ser Thr Thr Ile Thr Thr Asn
385                 390                 395                 400

tat gga aca acc aat aat cgt tta act aat ttt att cct cct act acc      1248
Tyr Gly Thr Thr Asn Asn Arg Leu Thr Asn Phe Ile Pro Pro Thr Thr
                405                 410                 415

agt gat gtt tat caa att aat tca atc tca agt aat tta gcc tct gct      1296
Ser Asp Val Tyr Gln Ile Asn Ser Ile Ser Ser Asn Leu Ala Ser Ala
            420                 425                 430

tta agc act tta ttt ggg gtt act aga gca caa ttc cat tat gga tca      1344
Leu Ser Thr Leu Phe Gly Val Thr Arg Ala Gln Phe His Tyr Gly Ser
        435                 440                 445

gga att att tgg tcg tat gtc gga caa aat aac gtt ctt cca caa tgt      1392
Gly Ile Ile Trp Ser Tyr Val Gly Gln Asn Asn Val Leu Pro Gln Cys
    450                 455                 460

cat caa aac tat aat tca ata gaa gaa tta cca aac caa agc gat gaa      1440
His Gln Asn Tyr Asn Ser Ile Glu Glu Leu Pro Asn Gln Ser Asp Glu
465                 470                 475                 480

cct aca gtt aga agt tat agc cat aga tta tct cat atc acc tct ttt      1488
Pro Thr Val Arg Ser Tyr Ser His Arg Leu Ser His Ile Thr Ser Phe
                485                 490                 495

aat ttc agt gta cag ctt aat aat cct gta att tct ctt ggc aat atg      1536
Asn Phe Ser Val Gln Leu Asn Asn Pro Val Ile Ser Leu Gly Asn Met
            500                 505                 510

cct gta tat gtg tgg aca cat cgc agt gtg gac ctt aat aac aca att      1584
Pro Val Tyr Val Trp Thr His Arg Ser Val Asp Leu Asn Asn Thr Ile
        515                 520                 525

act tca gat aga att act caa tta cca gcg gta aag gca tcg aca cta      1632
Thr Ser Asp Arg Ile Thr Gln Leu Pro Ala Val Lys Ala Ser Thr Leu
    530                 535                 540

ggt gcg gga gct att gtc gtg aaa ggt cca gga ttt aca gga gga gat      1680
Gly Ala Gly Ala Ile Val Val Lys Gly Pro Gly Phe Thr Gly Gly Asp
545                 550                 555                 560

gta atc cga aga aca tct gtt ggt gat ttc gga aca ata aga gtg tcg      1728
Val Ile Arg Arg Thr Ser Val Gly Asp Phe Gly Thr Ile Arg Val Ser
                565                 570                 575

gtt act ggc tcg cta act cag caa tat cgc ata agg ttc cgt tat gct      1776
Val Thr Gly Ser Leu Thr Gln Gln Tyr Arg Ile Arg Phe Arg Tyr Ala
            580                 585                 590

tcg aca ata gat ttt gat ttc ttt gta ata cgt gga gga act act ata      1824
Ser Thr Ile Asp Phe Asp Phe Phe Val Ile Arg Gly Gly Thr Thr Ile
        595                 600                 605

aat aat ttt aga ttc aca cat aca atg agc agt gga gag gaa tca aga      1872
Asn Asn Phe Arg Phe Thr His Thr Met Ser Ser Gly Glu Glu Ser Arg
    610                 615                 620

tat gaa tcc tat cgt act gta gag ttt tcc act cct ttt aac ttt aca      1920
Tyr Glu Ser Tyr Arg Thr Val Glu Phe Ser Thr Pro Phe Asn Phe Thr
625                 630                 635                 640

caa agt caa gat ata att cga aca tct atc cag gga ctt agt gga aat      1968
Gln Ser Gln Asp Ile Ile Arg Thr Ser Ile Gln Gly Leu Ser Gly Asn
                645                 650                 655
```

-continued

```
ggg gaa gta tat ctt gat aga att gaa atc att cct gtg aat ccg aca      2016
Gly Glu Val Tyr Leu Asp Arg Ile Glu Ile Ile Pro Val Asn Pro Thr
            660                 665                 670

cga gaa gca gaa gag gat cta gaa gat gca aag aaa gcg gtg gca ggc      2064
Arg Glu Ala Glu Glu Asp Leu Glu Asp Ala Lys Lys Ala Val Ala Gly
        675                 680                 685

ttg ttt aca cgt aca agg gac gga                                      2088
Leu Phe Thr Arg Thr Arg Asp Gly
    690                 695


<210> SEQ ID NO 6
<211> LENGTH: 696
<212> TYPE: PRT
<213> ORGANISM: Bacillus thuringiensis

<400> SEQUENCE: 6

Met Asn Arg Asn Asn Gln Asn Glu Tyr Glu Ile Ile Asp Ala Pro His
 1               5                  10                  15

Cys Gly Cys Pro Ser Asp Asp Val Val Lys Tyr Pro Leu Thr Asp Asp
            20                  25                  30

Pro Asn Ala Gly Leu Gln Asn Met Asn Tyr Lys Glu Tyr Leu Gln Met
        35                  40                  45

Tyr Gly Gly Asp Tyr Thr Asp Pro Leu Ile Asn Pro Asn Leu Ser Val
    50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Thr Val Tyr
                85                  90                  95

Thr Tyr Leu Leu Asn Ser Leu Trp Pro Asp Asp Glu Asn Ser Val Trp
            100                 105                 110

Asp Ala Phe Met Lys Arg Ile Glu Glu Leu Ile Asp Gln Lys Ile Ser
        115                 120                 125

Glu Ala Val Lys Gly Arg Ala Leu Asp Glu Leu Thr Gly Leu Gln Asp
    130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
            180                 185                 190

Gln Asn Tyr Ser Thr Ile Leu Leu Pro Val Tyr Ala Gln Ala Ala Asn
        195                 200                 205

Leu His Leu Leu Leu Leu Lys Asp Ala Asp Ile Tyr Gly Ala Arg Trp
    210                 215                 220

Gly Leu Asn Gln Thr Gln Ile Asp Gln Phe His Ser Arg Gln Gln Ser
225                 230                 235                 240

Leu Thr Arg Thr Tyr Thr Asn His Cys Val Thr Thr Tyr Asn Asp Gly
                245                 250                 255

Leu Ala Glu Leu Arg Gly Thr Ser Val Glu Ser Trp Leu Lys Tyr His
            260                 265                 270

Gln Tyr Arg Arg Glu Met Thr Val Thr Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Val Tyr Thr Asp Pro Ile Val Phe Asn Pro Pro Glu
```

-continued

```
305                 310                 315                 320

Pro Pro Ser Gly Ala Phe Cys Glu Ser Phe Tyr Asn Ile Arg Ala Ala
                325                 330                 335

Arg Glu Arg Leu Thr Phe Ser Gln Leu Glu Asn Ala Ile Ile Arg Pro
            340                 345                 350

Pro Arg Leu Phe Glu Arg Phe Gln Ala Leu Gly Ile Tyr Thr Gly Glu
        355                 360                 365

Ala Arg Leu Asn Gln Asn Ser Ala Pro Thr Asn Tyr Trp Ile Gly His
    370                 375                 380

Phe Ile Arg Asn Thr Arg Leu Gly Asp Ser Thr Thr Ile Thr Thr Asn
385                 390                 395                 400

Tyr Gly Thr Thr Asn Asn Arg Leu Thr Asn Phe Ile Pro Pro Thr Thr
                405                 410                 415

Ser Asp Val Tyr Gln Ile Asn Ser Ile Ser Ser Asn Leu Ala Ser Ala
            420                 425                 430

Leu Ser Thr Leu Phe Gly Val Thr Arg Ala Gln Phe His Tyr Gly Ser
        435                 440                 445

Gly Ile Ile Trp Ser Tyr Val Gly Gln Asn Asn Val Leu Pro Gln Cys
    450                 455                 460

His Gln Asn Tyr Asn Ser Ile Glu Glu Leu Pro Asn Gln Ser Asp Glu
465                 470                 475                 480

Pro Thr Val Arg Ser Tyr Ser His Arg Leu Ser His Ile Thr Ser Phe
                485                 490                 495

Asn Phe Ser Val Gln Leu Asn Asn Pro Val Ile Ser Leu Gly Asn Met
            500                 505                 510

Pro Val Tyr Val Trp Thr His Arg Ser Val Asp Leu Asn Asn Thr Ile
        515                 520                 525

Thr Ser Asp Arg Ile Thr Gln Leu Pro Ala Val Lys Ala Ser Thr Leu
    530                 535                 540

Gly Ala Gly Ala Ile Val Val Lys Gly Pro Gly Phe Thr Gly Gly Asp
545                 550                 555                 560

Val Ile Arg Arg Thr Ser Val Gly Asp Phe Gly Thr Ile Arg Val Ser
                565                 570                 575

Val Thr Gly Ser Leu Thr Gln Gln Tyr Arg Ile Arg Phe Arg Tyr Ala
            580                 585                 590

Ser Thr Ile Asp Phe Asp Phe Phe Val Ile Arg Gly Gly Thr Thr Ile
        595                 600                 605

Asn Asn Phe Arg Phe Thr His Thr Met Ser Ser Gly Glu Glu Ser Arg
    610                 615                 620

Tyr Glu Ser Tyr Arg Thr Val Glu Phe Ser Thr Pro Phe Asn Phe Thr
625                 630                 635                 640

Gln Ser Gln Asp Ile Ile Arg Thr Ser Ile Gln Gly Leu Ser Gly Asn
                645                 650                 655

Gly Glu Val Tyr Leu Asp Arg Ile Glu Ile Ile Pro Val Asn Pro Thr
            660                 665                 670

Arg Glu Ala Glu Glu Asp Leu Glu Asp Ala Lys Lys Ala Val Ala Gly
        675                 680                 685

Leu Phe Thr Arg Thr Arg Asp Gly
    690                 695
```

<210> SEQ ID NO 7
<211> LENGTH: 25
<212> TYPE: PRT
<213> ORGANISM: Bacillus thuringiensis -continued
<220> FEATURE:
<223> OTHER INFORMATION: “Xaa” is any amino acid

<400> SEQUENCE: 7

Xaa Ile Asn Pro Asn Leu Ser Ile Asn Thr Xaa Asp Val Leu Gln Thr
1 5 10 15

Gly Ile Thr Ile Val Gly Xaa Val Leu
20 25

<210> SEQ ID NO 8
<211> LENGTH: 19
<212> TYPE: DNA
<213> ORGANISM: Artificial Sequence
<220> FEATURE:
<223> OTHER INFORMATION: Primer set 1--forward primer

<400> SEQUENCE: 8
gagatgtact acaaacagg 19

<210> SEQ ID NO 9
<211> LENGTH: 21
<212> TYPE: DNA
<213> ORGANISM: Artificial Sequence
<220> FEATURE:
<223> OTHER INFORMATION: Primer set 1--reverse primer

<400> SEQUENCE: 9
ccatcccttg tacgtgtaaa c 21

<210> SEQ ID NO 10
<211> LENGTH: 28
<212> TYPE: DNA
<213> ORGANISM: Artificial Sequence
<220> FEATURE:
<223> OTHER INFORMATION: Primer set 2--forward primer

<400> SEQUENCE: 10
ggatccatga atcgaaataa tcaaaatg 28

<210> SEQ ID NO 11
<211> LENGTH: 34
<212> TYPE: DNA
<213> ORGANISM: Artificial Sequence
<220> FEATURE:
<223> OTHER INFORMATION: Primer set 2--reverse primer

<400> SEQUENCE: 11
ctcgagctgt aatccgtccc ttgtacgtgt aaac 34

<210> SEQ ID NO 12
<211> LENGTH: 1156
<212> TYPE: PRT
<213> ORGANISM: Bacillus thuringiensis galleriae

<400> SEQUENCE: 12

Met Asn Gln Asn Lys His Gly Ile Ile Gly Ala Ser Asn Cys Gly Cys
1 5 10 15

Ala Ser Asp Asp Val Ala Lys Tyr Pro Leu Ala Asn Asn Pro Tyr Ser
20 25 30

Ser Ala Leu Asn Leu Asn Ser Cys Gln Asn Ser Ser Ile Leu Asn Trp
35 40 45

Ile Asn Ile Ile Gly Asp Ala Ala Lys Glu Ala Val Ser Ile Gly Thr
50 55 60

-continued

```
Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
```

-continued

```
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Asn Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Ala Lys Lys Ala Val
            660                 665                 670

Ala Ser Leu Phe Thr Arg Thr Arg Asp Gly Leu Gln Val Asn Val Lys
        675                 680                 685

Asp Tyr Gln Val Asp Gln Ala Ala Asn Leu Val Ser Cys Leu Ser Asp
    690                 695                 700

Glu Gln Tyr Gly Tyr Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Ile Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Val Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Glu Ala Ala Gln Thr His Glu Phe Ser Ser Tyr Ile Asp Thr Gly Asp
865                 870                 875                 880

Leu Asn Ser Ser Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Val
            900                 905                 910
```

-continued

```
Gly Pro Leu Ser Gly Glu Ser Leu Glu Arg Glu Gln Arg Asp Asn Thr
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu Ile Tyr Thr Glu Leu Ser Asn Arg
        995                 1000                1005

Leu Gln Gln Ala Ser Tyr Leu Tyr Thr Ser Arg Asn Ala Val Gln Asn
    1010                1015                1020

Gly Asp Phe Asn Asn Gly Leu Asp Ser Trp Asn Ala Thr Ala Gly Ala
1025                1030                1035                1040

Ser Val Gln Gln Asp Gly Asn Thr His Phe Leu Val Leu Ser His Trp
                1045                1050                1055

Asp Ala Gln Val Ser Gln Gln Phe Arg Val Gln Pro Asn Cys Lys Tyr
            1060                1065                1070

Val Leu Arg Val Thr Ala Glu Lys Val Gly Gly Gly Asp Gly Tyr Val
        1075                1080                1085

Thr Ile Arg Asp Asp Ala His His Thr Glu Thr Leu Thr Phe Asn Ala
    1090                1095                1100

Cys Asp Tyr Asp Ile Asn Gly Thr Tyr Val Thr Asp Asn Thr Tyr Leu
1105                1110                1115                1120

Thr Lys Glu Val Val Phe His Pro Glu Thr Gln His Met Trp Val Glu
                1125                1130                1135

Val Asn Glu Thr Glu Gly Ala Phe His Ile Asp Ser Ile Glu Phe Val
            1140                1145                1150

Glu Thr Glu Lys
        1155


<210> SEQ ID NO 13
<211> LENGTH: 1151
<212> TYPE: PRT
<213> ORGANISM: Bacillus thuringiensis DSIR517

<400> SEQUENCE: 13

Met Asn Gln Asn Lys His Gly Ile Ile Gly Ala Ser Asn Cys Gly Cys
 1               5                  10                  15

Ala Ser Asp Asp Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
```

-continued

```
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540
```

-continued

Gly Gly Ala Leu Leu Gln Arg Thr Asp His Gly Ser Leu Gly Val Leu
545 550 555 560

Arg Val Gln Phe Pro Leu His Leu Arg Gln Gln Tyr Arg Ile Arg Val
565 570 575

Arg Tyr Ala Ser Thr Thr Asn Ile Arg Leu Ser Val Asn Gly Ser Phe
580 585 590

Gly Thr Ile Ser Gln Asn Leu Pro Ser Thr Met Arg Leu Gly Glu Asp
595 600 605

Leu Arg Tyr Gly Ser Phe Ala Ile Arg Glu Phe Asn Thr Ser Ile Arg
610 615 620

Pro Thr Ala Ser Pro Asp Gln Ile Arg Leu Thr Ile Glu Pro Ser Phe
625 630 635 640

Ile Arg Gln Glu Val Tyr Val Asp Arg Ile Glu Phe Ile Pro Val Asn
645 650 655

Pro Thr Arg Glu Ala Lys Glu Asp Leu Glu Ala Ala Lys Lys Ala Val
660 665 670

Ala Ser Leu Phe Thr Arg Thr Arg Asp Gly Leu Gln Val Asn Val Lys
675 680 685

Asp Tyr Gln Val Asp Gln Ala Ala Asn Leu Val Ser Cys Leu Ser Asp
690 695 700

Glu Gln Tyr Gly Tyr Asp Lys Lys Met Leu Leu Glu Ala Val Arg Ala
705 710 715 720

Ala Lys Arg Leu Ser Arg Glu Arg Asn Leu Leu Gln Asp Pro Asp Phe
725 730 735

Asn Thr Ile Asn Ser Thr Glu Glu Asn Gly Trp Lys Ala Ser Asn Gly
740 745 750

Val Thr Ile Ser Glu Gly Gly Pro Phe Tyr Lys Gly Arg Ala Ile Gln
755 760 765

Leu Ala Ser Ala Arg Glu Asn Tyr Pro Thr Tyr Ile Tyr Gln Lys Val
770 775 780

Asp Ala Ser Glu Leu Lys Pro Tyr Thr Arg Tyr Arg Leu Asp Gly Phe
785 790 795 800

Val Lys Ser Ser Gln Asp Leu Glu Ile Asp Leu Ile His His His Lys
805 810 815

Val His Leu Val Lys Asn Val Pro Asp Asn Leu Val Ser Asp Thr Tyr
820 825 830

Pro Asp Asp Ser Cys Ser Gly Ile Asn Arg Cys Gln Glu Gln Gln Met
835 840 845

Val Asn Ala Gln Leu Glu Thr Glu His His His Pro Met Asp Cys Cys
850 855 860

Glu Ala Ala Gln Thr His Glu Phe Ser Ser Tyr Ile Asp Thr Gly Asp
865 870 875 880

Leu Asn Ser Ser Val Asp Gln Gly Ile Trp Ala Ile Phe Lys Val Arg
885 890 895

Thr Thr Asp Gly Tyr Ala Thr Leu Gly Asn Leu Glu Leu Val Glu Val
900 905 910

Gly Pro Leu Ser Gly Glu Ser Leu Glu Arg Glu Gln Arg Asp Asn Thr
915 920 925

Lys Trp Ser Ala Glu Leu Gly Arg Lys Arg Ala Glu Thr Asp Arg Val
930 935 940

Tyr Gln Asp Ala Lys Gln Ser Ile Asn His Leu Phe Val Asp Tyr Gln
945 950 955 960

-continued

```
Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu Ile Tyr Thr Glu Leu Ser Asn Arg
        995                 1000                1005

Leu Gln Gln Ala Ser Tyr Leu Tyr Thr Ser Arg Asn Ala Val Gln Asn
    1010                1015                1020

Gly Asp Phe Asn Asn Gly Leu Asp Ser Trp Asn Ala Thr Ala Gly Ala
1025                1030                1035                1040

Ser Val Gln Gln Asp Gly Asn Thr His Phe Leu Val Leu Ser His Trp
                1045                1050                1055

Asp Ala Gln Val Ser Gln Gln Phe Arg Val Gln Pro Asn Cys Lys Tyr
            1060                1065                1070

Val Leu Arg Val Thr Ala Glu Lys Val Gly Gly Gly Asp Gly Tyr Val
        1075                1080                1085

Thr Ile Arg Asp Asp Ala His His Thr Glu Thr Leu Thr Phe Asn Ala
    1090                1095                1100

Cys Asp Tyr Asp Ile Asn Gly Thr Tyr Val Thr Asp Asn Thr Tyr Leu
1105                1110                1115                1120

Thr Lys Glu Val Val Phe His Pro Glu Thr Gln His Met Trp Val Glu
                1125                1130                1135

Val Asn Glu Thr Glu Gly Ala Phe His Ile Asp Ser Ile Glu Phe
            1140                1145                1150


<210> SEQ ID NO 14
<211> LENGTH: 1169
<212> TYPE: PRT
<213> ORGANISM: Bacillus thuringiensis japonensis

<400> SEQUENCE: 14

Met Asn Arg Asn Asn Gln Asn Glu Tyr Glu Val Ile Asp Ala Pro His
 1               5                  10                  15

Cys Gly Cys Pro Ala Asp Asp Val Val Lys Tyr Pro Leu Thr Asp Asp
            20                  25                  30

Pro Asn Ala Gly Leu Gln Asn Met Asn Tyr Lys Glu Tyr Leu Gln Thr
        35                  40                  45

Tyr Gly Gly Asp Tyr Thr Asp Pro Leu Ile Asn Pro Asn Leu Ser Val
    50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Thr Val Tyr
                85                  90                  95

Thr Tyr Leu Leu Asn Ser Leu Trp Pro Asp Asp Glu Asn Ser Val Trp
            100                 105                 110

Asp Ala Phe Met Glu Arg Val Glu Glu Leu Ile Asp Gln Lys Ile Ser
        115                 120                 125

Glu Ala Val Lys Gly Arg Ala Leu Asp Asp Leu Thr Gly Leu Gln Tyr
    130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
            180                 185                 190
```

-continued

```
Gln Asn Tyr Ala Thr Ile Leu Leu Pro Val Tyr Ala Gln Ala Ala Asn
        195                 200                 205

Leu His Leu Leu Leu Leu Lys Asp Ala Asp Ile Tyr Gly Ala Arg Trp
    210                 215                 220

Gly Leu Asn Gln Thr Gln Ile Asp Gln Phe His Ser Arg Gln Gln Ser
225                 230                 235                 240

Leu Thr Gln Thr Tyr Thr Asn His Cys Val Thr Ala Tyr Asn Asp Gly
                245                 250                 255

Leu Ala Glu Leu Arg Gly Thr Thr Ala Glu Ser Trp Phe Lys Tyr Asn
            260                 265                 270

Gln Tyr Arg Arg Glu Met Thr Leu Thr Ala Met Asp Leu Val Ala Leu
        275                 280                 285

Phe Pro Tyr Tyr Asn Leu Arg Gln Tyr Pro Asp Gly Thr Asn Pro Gln
    290                 295                 300

Leu Thr Arg Glu Val Tyr Thr Asp Pro Ile Ala Phe Asp Pro Leu Glu
305                 310                 315                 320

Gln Pro Thr Thr Gln Leu Cys Arg Ser Trp Tyr Ile Asn Pro Ala Phe
                325                 330                 335

Arg Asn His Leu Asn Phe Ser Val Leu Glu Asn Ser Leu Ile Arg Pro
            340                 345                 350

Pro His Leu Phe Glu Arg Leu Ser Asn Leu Gln Ile Leu Val Asn Tyr
        355                 360                 365

Gln Thr Asn Gly Ser Ala Trp Arg Gly Ser Arg Val Arg Tyr His Tyr
    370                 375                 380

Leu His Ser Ser Ile Ile Gln Glu Lys Ser Tyr Gly Leu Leu Ser Asp
385                 390                 395                 400

Pro Val Gly Ala Asn Ile Asn Val Gln Asn Asn Asp Ile Tyr Gln Ile
                405                 410                 415

Ile Ser Gln Val Ser Asn Phe Ala Ser Pro Val Gly Ser Ser Tyr Ser
            420                 425                 430

Val Trp Asp Thr Asn Phe Tyr Leu Ser Ser Gly Gln Val Ser Gly Ile
        435                 440                 445

Ser Gly Tyr Thr Gln Gln Gly Ile Pro Ala Val Cys Leu Gln Gln Arg
    450                 455                 460

Asn Ser Thr Asp Glu Leu Pro Ser Leu Asn Pro Glu Gly Asp Ile Ile
465                 470                 475                 480

Arg Asn Tyr Ser His Arg Leu Ser His Ile Thr Gln Tyr Arg Phe Gln
                485                 490                 495

Ala Thr Gln Ser Gly Ser Pro Ser Thr Val Ser Ala Asn Leu Pro Thr
            500                 505                 510

Cys Val Trp Thr His Arg Asp Val Asp Leu Asp Asn Thr Ile Thr Ala
        515                 520                 525

Asn Gln Ile Thr Gln Leu Pro Leu Val Lys Ala Tyr Glu Leu Ser Ser
    530                 535                 540

Gly Ala Thr Val Val Lys Gly Pro Gly Phe Thr Gly Gly Asp Val Ile
545                 550                 555                 560

Arg Arg Thr Asn Thr Gly Gly Phe Gly Ala Ile Arg Val Ser Val Thr
                565                 570                 575

Gly Pro Leu Thr Gln Arg Tyr Arg Ile Arg Phe Arg Tyr Ala Ser Thr
            580                 585                 590

Ile Asp Phe Asp Phe Phe Val Thr Arg Gly Gly Thr Thr Ile Asn Asn
        595                 600                 605
```

-continued

```
Phe Arg Phe Thr Arg Thr Met Asn Arg Gly Gln Glu Ser Arg Tyr Glu
    610                 615                 620

Ser Tyr Arg Thr Val Glu Phe Thr Thr Pro Phe Asn Phe Thr Gln Ser
625                 630                 635                 640

Gln Asp Ile Ile Arg Thr Ser Ile Gln Gly Leu Ser Gly Asn Gly Glu
                645                 650                 655

Val Tyr Leu Asp Arg Ile Glu Ile Ile Pro Val Asn Pro Ala Arg Glu
            660                 665                 670

Ala Glu Glu Asp Leu Glu Ala Ala Lys Lys Ala Ala Arg Gln Asn Leu
        675                 680                 685

Phe Thr Arg Thr Arg Asp Gly Leu Gln Val Asn Val Thr Asp Tyr Gln
    690                 695                 700

Val Asp Gln Ala Ala Asn Leu Val Ser Cys Leu Ser Asp Glu Gln Tyr
705                 710                 715                 720

Gly His Asp Lys Lys Met Leu Leu Glu Ala Val Arg Ala Ala Lys Arg
                725                 730                 735

Leu Ser Arg Glu Arg Asn Leu Leu Gln Asp Pro Asp Phe Asn Thr Ile
            740                 745                 750

Asn Ser Thr Glu Glu Asn Gly Trp Lys Ala Ser Asn Gly Val Thr Ile
        755                 760                 765

Ser Glu Gly Gly Pro Phe Phe Lys Gly Arg Ala Leu Gln Leu Ala Ser
    770                 775                 780

Ala Arg Glu Asn Tyr Pro Thr Tyr Ile Tyr Gln Lys Val Asp Ala Ser
785                 790                 795                 800

Val Leu Lys Pro Tyr Thr Arg Tyr Arg Leu Asp Gly Phe Val Lys Ser
                805                 810                 815

Ser Gln Asp Leu Glu Ile Asp Leu Ile His Tyr His Lys Val His Leu
            820                 825                 830

Val Lys Asn Val Pro Asp Asn Leu Val Ser Asp Thr Tyr Ser Asp Gly
        835                 840                 845

Ser Cys Ser Gly Met Asn Arg Cys Glu Glu Gln Gln Met Val Asn Ala
    850                 855                 860

Gln Leu Glu Thr Glu His His His Pro Met Asp Cys Cys Glu Ala Ala
865                 870                 875                 880

Gln Thr His Glu Phe Ser Ser Tyr Ile Asn Thr Gly Asp Leu Asn Ala
                885                 890                 895

Ser Val Asp Gln Gly Ile Trp Val Val Leu Lys Val Arg Thr Thr Asp
            900                 905                 910

Gly Tyr Ala Thr Leu Gly Asn Leu Glu Leu Val Glu Val Gly Pro Leu
        915                 920                 925

Ser Gly Glu Ser Leu Glu Arg Glu Gln Arg Asp Asn Ala Lys Trp Asn
    930                 935                 940

Ala Glu Leu Gly Arg Lys Arg Ala Glu Ile Asp Arg Val Tyr Leu Ala
945                 950                 955                 960

Ala Lys Gln Ala Ile Asn His Leu Phe Val Asp Tyr Gln Asp Gln Gln
                965                 970                 975

Leu Asn Pro Glu Ile Gly Leu Ala Glu Ile Asn Glu Ala Ser Asn Leu
            980                 985                 990

Val Glu Ser Ile Ser Gly Val Tyr Ser Asp Thr Leu Leu Gln Ile Pro
        995                 1000                1005

Gly Ile Asn Tyr Glu Ile Tyr Thr Glu Leu Ser Asp Arg Leu Gln Gln
    1010                1015                1020

Ala Ser Tyr Leu Tyr Thr Ser Arg Asn Ala Val Gln Asn Gly Asp Phe
```

-continued

```
1025                1030                1035                1040

Asn Ser Gly Leu Asp Ser Trp Asn Thr Thr Thr Asp Ala Ser Val Gln
                1045                1050                1055

Gln Asp Gly Asn Met His Phe Leu Val Leu Ser His Trp Asp Ala Gln
            1060                1065                1070

Val Ser Gln Gln Leu Arg Val Asn Pro Asn Cys Lys Tyr Val Leu Arg
        1075                1080                1085

Val Thr Ala Arg Lys Val Gly Gly Gly Asp Gly Tyr Val Thr Ile Arg
    1090                1095                1100

Asp Gly Ala His His Gln Glu Thr Leu Thr Phe Asn Ala Cys Asp Tyr
1105                1110                1115                1120

Asp Val Asn Gly Thr Tyr Val Asn Asp Asn Ser Tyr Ile Thr Glu Glu
                1125                1130                1135

Val Val Phe Tyr Pro Glu Thr Lys His Met Trp Val Glu Val Ser Glu
            1140                1145                1150

Ser Glu Gly Ser Phe Tyr Ile Asp Ser Ile Glu Phe Ile Glu Thr Gln
        1155                1160                1165

Glu


<210> SEQ ID NO 15
<211> LENGTH: 645
<212> TYPE: PRT
<213> ORGANISM: Bacillus thuringiensis japonensis

<400> SEQUENCE: 15

His Cys Gly Cys Pro Ala Asp Asp Val Val Lys Tyr Pro Leu Thr Asp
 1               5                  10                  15

Asp Pro Asn Ala Gly Leu Gln Asn Met Asn Tyr Lys Glu Tyr Leu Gln
            20                  25                  30

Thr Tyr Gly Gly Asp Tyr Thr Asp Pro Leu Ile Asn Pro Asn Leu Ser
        35                  40                  45

Val Ser Gly Lys Asp Val Ile Gln Val Gly Ile Asn Ile Val Gly Arg
    50                  55                  60

Leu Leu Ser Phe Phe Gly Phe Pro Phe Ser Ser Gln Trp Val Thr Val
65                  70                  75                  80

Tyr Thr Tyr Leu Leu Asn Ser Leu Trp Pro Asp Asp Glu Asn Ser Val
                85                  90                  95

Trp Asp Ala Phe Met Glu Arg Val Glu Glu Leu Ile Asp Gln Lys Ile
            100                 105                 110

Ser Glu Ala Val Lys Gly Arg Ala Leu Asp Asp Leu Thr Gly Leu Gln
        115                 120                 125

Tyr Asn Tyr Asn Leu Tyr Val Glu Ala Leu Asp Glu Trp Leu Asn Arg
    130                 135                 140

Pro Asn Gly Ala Arg Ala Ser Leu Val Ser Gln Arg Phe Asn Ile Leu
145                 150                 155                 160

Asp Ser Leu Phe Thr Gln Phe Met Pro Ser Phe Gly Ser Gly Pro Gly
                165                 170                 175

Ser Gln Asn Tyr Ala Thr Ile Leu Leu Pro Val Tyr Ala Gln Ala Ala
            180                 185                 190

Asn Leu His Leu Leu Leu Leu Lys Asp Ala Asp Ile Tyr Gly Ala Arg
        195                 200                 205

Trp Gly Leu Asn Gln Thr Gln Ile Asp Gln Phe His Ser Arg Gln Gln
    210                 215                 220

Ser Leu Thr Gln Thr Tyr Thr Asn His Cys Val Thr Ala Tyr Asn Asp
```

-continued

```
225                 230                 235                 240

Gly Leu Ala Glu Leu Arg Gly Thr Thr Ala Glu Ser Trp Phe Lys Tyr
                245                 250                 255

Asn Gln Tyr Arg Arg Glu Met Thr Leu Thr Ala Met Asp Leu Val Ala
            260                 265                 270

Leu Phe Pro Tyr Tyr Asn Leu Arg Gln Tyr Pro Asp Gly Thr Asn Pro
        275                 280                 285

Gln Leu Thr Arg Glu Val Tyr Thr Asp Pro Ile Ala Phe Asp Pro Leu
    290                 295                 300

Glu Gln Pro Thr Thr Gln Leu Cys Arg Ser Trp Tyr Ile Asn Pro Ala
305                 310                 315                 320

Phe Arg Asn His Leu Asn Phe Ser Val Leu Glu Asn Ser Leu Ile Arg
                325                 330                 335

Pro Pro His Leu Phe Glu Arg Leu Ser Asn Leu Gln Ile Leu Val Asn
            340                 345                 350

Tyr Gln Thr Asn Gly Ser Ala Trp Arg Gly Ser Arg Val Arg Tyr His
        355                 360                 365

Tyr Leu His Ser Ser Ile Ile Gln Glu Lys Ser Tyr Gly Leu Leu Ser
    370                 375                 380

Asp Pro Val Gly Ala Asn Ile Asn Val Gln Asn Asn Asp Ile Tyr Gln
385                 390                 395                 400

Ile Ile Ser Gln Val Ser Asn Phe Ala Ser Pro Val Gly Ser Ser Tyr
                405                 410                 415

Ser Val Trp Asp Thr Asn Phe Tyr Leu Ser Ser Gly Gln Val Ser Gly
            420                 425                 430

Ile Ser Gly Tyr Thr Gln Gln Gly Ile Pro Ala Val Cys Leu Gln Gln
        435                 440                 445

Arg Asn Ser Thr Asp Glu Leu Pro Ser Leu Asn Pro Glu Gly Asp Ile
    450                 455                 460

Ile Arg Asn Tyr Ser His Arg Leu Ser His Ile Thr Gln Tyr Arg Phe
465                 470                 475                 480

Gln Ala Thr Gln Ser Gly Ser Pro Ser Thr Val Ser Ala Asn Leu Pro
                485                 490                 495

Thr Cys Val Trp Thr His Arg Asp Val Asp Leu Asp Asn Thr Ile Thr
            500                 505                 510

Ala Asn Gln Ile Thr Gln Leu Pro Leu Val Lys Ala Tyr Glu Leu Ser
        515                 520                 525

Ser Gly Ala Thr Val Val Lys Gly Pro Gly Phe Thr Gly Gly Asp Val
    530                 535                 540

Ile Arg Arg Thr Asn Thr Gly Gly Phe Gly Ala Ile Arg Val Ser Val
545                 550                 555                 560

Thr Gly Pro Leu Thr Gln Arg Tyr Arg Ile Arg Phe Arg Tyr Ala Ser
                565                 570                 575

Thr Ile Asp Phe Asp Phe Phe Val Thr Arg Gly Gly Thr Thr Ile Asn
            580                 585                 590

Asn Phe Arg Phe Thr Arg Thr Met Asn Arg Gly Gln Glu Ser Arg Tyr
        595                 600                 605

Glu Ser Tyr Arg Thr Val Glu Phe Thr Thr Pro Phe Asn Phe Thr Gln
    610                 615                 620

Ser Gln Asp Ile Ile Arg Thr Ser Ile Gln Gly Leu Ser Gly Asn Gly
625                 630                 635                 640

Glu Val Tyr Leu Asp
                645
```

-continued

<210> SEQ ID NO 16
<211> LENGTH: 638
<212> TYPE: PRT
<213> ORGANISM: Bacillus thuringiensis galleriae

<400> SEQUENCE: 16

```
Glu Ile Ile Asp Gly Thr Asn Cys Gly Cys Ser Ser Asp Glu Val Val
 1               5                  10                  15

Lys Tyr Pro Leu Thr Asp Asp Pro Asn Ala Gly Leu Gln Asn Met Asn
            20                  25                  30

Tyr Lys Glu Tyr Leu Gln Thr Tyr Asp Gly Asp Tyr Thr Gly Ser Leu
        35                  40                  45

Ile Asn Pro Asn Leu Ser Ile Asn Thr Arg Asp Val Leu Gln Thr Gly
    50                  55                  60

Ile Asn Ile Val Gly Arg Val Leu Gly Phe Leu Gly Val Pro Phe Ala
65                  70                  75                  80

Gly Gln Leu Val Thr Phe Tyr Thr Phe Leu Leu Asn Gln Leu Trp Pro
                85                  90                  95

Thr Asn Asn Asn Ala Val Trp Glu Ala Phe Met Ala Gln Ile Glu Glu
            100                 105                 110

Leu Ile Asp Gln Arg Ile Ser Glu Gln Val Val Arg Asn Ala Leu Asp
        115                 120                 125

Ala Leu Thr Gly Ile His Asp Tyr Tyr Asn Glu Tyr Leu Ala Ala Leu
    130                 135                 140

Glu Glu Trp Leu Glu Arg Pro Asn Gly Ala Arg Ala Asn Leu Ala Phe
145                 150                 155                 160

Gln Arg Phe Glu Asn Leu His Gln Leu Phe Val Ser Gln Met Pro Ser
                165                 170                 175

Phe Gly Ser Gly Pro Gly Ser Glu Arg Asp Ala Val Ala Leu Leu Thr
            180                 185                 190

Val Tyr Ala Gln Ala Ala Asn Leu His Leu Leu Leu Leu Lys Asp Ala
        195                 200                 205

Glu Ile Tyr Gly Ala Arg Trp Gly Leu Asn Gln Gly Gln Ile Asn Leu
    210                 215                 220

Tyr Phe Asn Ala Gln Gln Asp Arg Thr Gln Ile Tyr Thr Asn His Cys
225                 230                 235                 240

Val Ala Thr Tyr Asn Arg Gly Leu Glu Asn Leu Arg Gly Thr Asn Thr
                245                 250                 255

Glu Ser Trp Tyr Asn Tyr His Gln Phe Arg Arg Glu Met Thr Leu Met
            260                 265                 270

Ala Met Asp Leu Val Ala Leu Phe Pro Tyr Tyr Asn Leu Arg Gln Tyr
        275                 280                 285

Pro Asn Gly Ala Asn Pro Gln Leu Thr Arg Glu Ile Tyr Thr Asp Pro
    290                 295                 300

Val Val Phe Asn Pro Pro Ala Asn Gln Gly Leu Cys Arg Arg Trp Arg
305                 310                 315                 320

Asn Asn Pro Tyr Met Thr Phe Ser Glu Leu Glu Asn Thr Phe Ile Arg
                325                 330                 335

Pro Pro His Leu Phe Asp Arg Leu Asn Ser Leu Thr Ile Asn Ser His
            340                 345                 350

Arg Phe Pro Ile Ser Ser Asn Phe Met Asp Tyr Trp Ala Gly His Thr
        355                 360                 365

Leu Arg Arg Ser Tyr Met Asn Asn Ser Ala Val Gln Glu Asp Ser Tyr
```

-continued

```
    370                 375                 380

Gly Ala Thr Thr Ser Thr Arg Val Thr Ile Asn Thr Gly Val Asn Gly
385                 390                 395                 400

Thr Asn Arg Ile Glu Ser Thr Ala Val Asp Phe Arg Ser Gly Leu Leu
                405                 410                 415

Gly Val Tyr Gly Val His Arg Ala Ser Phe Val Pro Gly Gly Leu Phe
            420                 425                 430

Asn Gly Thr Ile Ser Pro Ala Asn Ala Gly Cys Arg Asn Leu His Asp
        435                 440                 445

Thr Arg Asp Glu Leu Pro Leu Glu Glu Asn Asn Gly Ser Pro Ser His
    450                 455                 460

Arg Leu Ser His Val Thr Phe Leu Ser Phe Leu Thr Asp Gln Ala Gly
465                 470                 475                 480

Ser Ile Arg Asn Ser Gly Ala Val Pro Leu Tyr Val Trp Ala Arg Gln
                485                 490                 495

Asp Ile Asp Leu Asn Asn Thr Ile Thr Ala Asn Arg Ile Thr Gln Leu
            500                 505                 510

Pro Leu Val Lys Ala Ser Glu Ile Ala Ala Gly Thr Thr Val Val Arg
        515                 520                 525

Gly Pro Gly Phe Thr Gly Gly Asp Ile Leu Arg Arg Thr Ser Ala Gly
    530                 535                 540

Thr Leu Gly Thr Ile Arg Val Asn Val Asn Ser Pro Leu Thr Gln Arg
545                 550                 555                 560

Tyr Arg Val Arg Phe Arg Tyr Ala Ser Thr Thr Asp Phe Asn Phe Phe
                565                 570                 575

Val Ile Arg Gly Gly Thr Thr Val Asn Asn Phe Thr Phe Pro Arg Thr
            580                 585                 590

Met Asn Ser Gly Gln Glu Ser Arg Tyr Glu Ser Tyr Val Thr Arg Glu
        595                 600                 605

Phe Ser Thr Ser Phe Asn Phe Leu Gln Ile Gln Asp Thr Leu Arg Leu
    610                 615                 620

Thr Val Gln Ser Phe Ser Ser Gly Gln Gln Val Tyr Val Asp
625                 630                 635


<210> SEQ ID NO 17
<211> LENGTH: 1152
<212> TYPE: PRT
<213> ORGANISM: Bacillus thuringiensis

<400> SEQUENCE: 17

Met Asn Arg Asn Asn Gln Asn Asp Tyr Glu Val Ile Asp Ala Ser Asn
 1               5                  10                  15

Cys Gly Cys Ala Ser Asp Asp Val Val Gln Tyr Pro Leu Ala Arg Asp
            20                  25                  30

Pro Asn Ala Val Phe Gln Asn Met His Tyr Lys Asp Tyr Leu Gln Thr
        35                  40                  45

Tyr Asp Gly Asp Tyr Thr Gly Ser Phe Ile Asn Pro Asn Leu Ser Ile
    50                  55                  60

Asn Pro Arg Asp Val Leu Gln Thr Gly Ile Asn Ile Val Gly Arg Leu
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asp Asn Ala Val Trp
            100                 105                 110
```

-continued

```
Glu Ala Phe Met Ala Gln Ile Glu Glu Leu Ile Asn Gln Arg Ile Ser
        115                 120                 125

Glu Ala Val Val Gly Thr Ala Ala Asp His Leu Thr Gly Leu His Asp
    130                 135                 140

Asn Tyr Glu Leu Tyr Val Glu Ala Leu Glu Glu Trp Leu Glu Arg Pro
145                 150                 155                 160

Asn Ala Ala Arg Thr Asn Leu Leu Phe Asn Arg Phe Thr Thr Leu Asp
                165                 170                 175

Ser Leu Phe Thr Gln Phe Met Pro Ser Phe Gly Thr Gly Pro Gly Ser
            180                 185                 190

Gln Asn Tyr Ala Val Pro Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Asn Gln Asn Gln Ile Asn Ser Phe His Thr Arg Gln Gln Glu
225                 230                 235                 240

Arg Thr Gln Tyr Tyr Thr Asn His Cys Val Thr Thr Tyr Asn Thr Gly
                245                 250                 255

Leu Asp Arg Leu Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
                325                 330                 335

Ser Glu Leu Glu Asn Ala Phe Ile Arg Pro Pro His Leu Phe Asp Arg
            340                 345                 350

Leu Asn Arg Leu Thr Ile Ser Arg Asn Arg Tyr Thr Ala Pro Thr Thr
        355                 360                 365

Asn Ser Tyr Leu Asp Tyr Trp Ser Gly His Thr Leu Gln Ser Gln Tyr
    370                 375                 380

Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Asn Ala Ile Asp Ser
                405                 410                 415

Arg Ala Arg Asn Phe Gly Asn Leu Tyr Ala Asn Leu Tyr Gly Val Ser
            420                 425                 430

Tyr Leu Asn Ile Phe Pro Thr Gly Val Met Ser Glu Ile Thr Ser Ala
        435                 440                 445

Pro Asn Thr Cys Trp Gln Asp Leu Thr Thr Thr Glu Glu Leu Pro Leu
    450                 455                 460

Val Asn Asn Asn Phe Asn Leu Leu Ser His Val Thr Phe Leu Arg Phe
465                 470                 475                 480

Asn Thr Thr Gln Gly Gly Pro Leu Ala Thr Val Gly Phe Val Pro Thr
                485                 490                 495

Tyr Val Trp Thr Arg Gln Asp Val Asp Phe Asn Asn Ile Ile Thr Pro
            500                 505                 510

Asn Arg Ile Thr Gln Ile Pro Val Val Lys Ala Tyr Glu Leu Ser Ser
        515                 520                 525

Gly Ala Thr Val Val Lys Gly Pro Gly Phe Thr Gly Gly Asp Val Ile
```

-continued

```
    530                 535                 540

Arg Arg Thr Asn Thr Gly Gly Phe Gly Ala Ile Arg Val Ser Val Thr
545                 550                 555                 560

Gly Pro Leu Thr Gln Arg Tyr Arg Ile Arg Phe Arg Tyr Ala Ser Thr
                565                 570                 575

Ile Asp Phe Asp Phe Phe Val Thr Arg Gly Gly Thr Thr Ile Asn Asn
            580                 585                 590

Phe Arg Phe Thr Arg Thr Met Asn Arg Gly Gln Glu Ser Arg Tyr Glu
        595                 600                 605

Ser Tyr Arg Thr Val Glu Phe Thr Thr Pro Phe Asn Phe Thr Gln Ser
    610                 615                 620

Gln Asp Ile Ile Arg Thr Ser Ile Gln Gly Leu Ser Gly Asn Gly Glu
625                 630                 635                 640

Val Tyr Leu Asp Arg Ile Glu Ile Ile Pro Val Asn Pro Thr Arg Glu
                645                 650                 655

Ala Glu Glu Asp Leu Glu Ala Ala Lys Lys Ala Val Ala Ser Leu Phe
            660                 665                 670

Thr Arg Thr Arg Asp Gly Leu Gln Val Asn Val Thr Asp Tyr Gln Val
        675                 680                 685

Asp Gln Ala Ala Asn Leu Val Ser Cys Leu Ser Asp Glu Gln Tyr Ala
    690                 695                 700

His Asp Lys Lys Met Leu Leu Glu Ala Val Arg Ala Ala Lys Arg Leu
705                 710                 715                 720

Ser Arg Glu Arg Asn Leu Leu Gln Asp Pro Asp Phe Asn Thr Ile Asn
                725                 730                 735

Ser Thr Glu Glu Asn Gly Trp Lys Ala Ser Asn Gly Val Thr Ile Ser
            740                 745                 750

Glu Gly Gly Pro Phe Tyr Lys Gly Arg Ala Leu Gln Leu Ala Ser Ala
        755                 760                 765

Arg Glu Asn Tyr Pro Thr Tyr Ile Tyr Gln Lys Val Asp Ala Ser Glu
    770                 775                 780

Leu Lys Pro Tyr Thr Arg Tyr Arg Leu Asp Gly Phe Val Lys Ser Ser
785                 790                 795                 800

Gln Asp Leu Glu Ile Asp Leu Ile His His His Lys Val His Leu Val
                805                 810                 815

Lys Asn Val Leu Asp Asn Leu Val Ser Asp Thr Tyr Pro Asp Asp Ser
            820                 825                 830

Cys Ser Gly Ile Asn Arg Cys Glu Glu Gln Gln Met Val Asn Ala Gln
        835                 840                 845

Leu Glu Thr Glu His His His Pro Met Asp Cys Cys Glu Ala Ala Gln
    850                 855                 860

Thr His Glu Phe Ser Ser Tyr Ile Asp Thr Gly Asp Leu Asn Ser Thr
865                 870                 875                 880

Val Asp Gln Gly Ile Trp Val Ile Phe Lys Val Arg Thr Thr Asp Gly
                885                 890                 895

Tyr Ala Thr Leu Gly Asn Leu Glu Leu Val Glu Val Gly Pro Leu Leu
            900                 905                 910

Gly Glu Pro Leu Glu Arg Glu Gln Arg Glu Asn Ala Lys Trp Asn Ala
        915                 920                 925

Glu Leu Gly Arg Lys Arg Ala Glu Thr Asp Arg Val Tyr Gln Asp Ala
    930                 935                 940

Lys Gln Ser Ile Asn His Leu Phe Val Asp Tyr Gln Asp Gln Gln Leu
945                 950                 955                 960
```

-continued

```
Asn Pro Gln Ile Gly Met Ala Asp Ile Met Asp Ala Gln Asn Leu Val
                965                 970                 975

Ala Ser Ile Ser Asp Val Tyr Ser Asp Ala Val Leu Gln Ile Pro Gly
            980                 985                 990

Ile Asn Tyr Glu Ile Tyr Thr Glu Leu Ser Asn Arg Leu Gln Gln Ala
        995                 1000                1005

Ser Tyr Leu Tyr Thr Ser Arg Asn Ala Val Gln Asn Gly Asp Phe Asn
    1010                1015                1020

Asn Gly Leu Asp Ser Trp Asn Ala Thr Ala Gly Ala Ser Val Gln Gln
1025                1030                1035                1040

Asp Gly Asn Thr His Phe Leu Val Leu Ser His Trp Asp Ala Gln Val
                1045                1050                1055

Ser Gln Gln Phe Arg Val Gln Pro Asn Cys Lys Tyr Val Leu Arg Val
            1060                1065                1070

Thr Ala Glu Lys Val Gly Gly Gly Asp Gly Tyr Val Thr Ile Arg Asp
        1075                1080                1085

Gly Ala His His Thr Glu Thr Leu Thr Phe Asn Ala Cys Asp Tyr Asp
    1090                1095                1100

Ile Asn Gly Thr Tyr Val Thr Asp Asn Thr Tyr Leu Thr Lys Glu Val
1105                1110                1115                1120

Ile Phe Tyr Ser His Thr Glu His Met Trp Val Glu Val Asn Glu Thr
                1125                1130                1135

Glu Gly Ala Phe His Ile Asp Ser Ile Glu Phe Val Glu Thr Glu Lys
            1140                1145                1150


<210> SEQ ID NO 18
<211> LENGTH: 1150
<212> TYPE: PRT
<213> ORGANISM: Bacillus thuringiensis aizawai

<400> SEQUENCE: 18

Met Asn Arg Asn Asn Pro Asn Glu Tyr Glu Ile Ile Asp Ala Pro Tyr
 1               5                   10                  15

Cys Gly Cys Pro Ser Asp Asp Asp Val Arg Tyr Pro Leu Ala Ser Asp
            20                  25                  30

Pro Asn Ala Ala Phe Gln Asn Met Asn Tyr Lys Glu Tyr Leu Gln Thr
        35                  40                  45

Tyr Asp Gly Asp Tyr Thr Gly Ser Leu Ile Asn Pro Asn Leu Ser Ile
    50                  55                  60

Asn Pro Arg Asp Val Leu Gln Thr Gly Ile Asn Ile Val Gly Arg Ile
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asp Gln Lys Ile Ser
        115                 120                 125

Ala Gln Val Val Arg Asn Ala Leu Asp Asp Leu Thr Gly Leu His Asp
    130                 135                 140

Tyr Tyr Glu Glu Tyr Leu Ala Ala Leu Glu Glu Trp Leu Glu Arg Pro
145                 150                 155                 160

Asn Gly Ala Arg Ala Asn Leu Val Thr Gln Arg Phe Glu Asn Leu His
                165                 170                 175

Thr Ala Phe Val Thr Arg Met Pro Ser Phe Gly Thr Gly Pro Gly Ser
```

-continued

```
            180                 185                 190

Gln Arg Asp Ala Val Ala Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Gln Gln Gly Gln Ile Asn Leu Tyr Phe Asn Ala Gln Gln Glu
225                 230                 235                 240

Arg Thr Arg Ile Tyr Thr Asn His Cys Val Glu Thr Tyr Asn Arg Gly
                245                 250                 255

Leu Glu Asp Val Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
        275                 280                 285

Phe Pro Phe Tyr Asn Val Arg Gln Tyr Pro Asn Gly Ala Asn Pro Gln
    290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
                325                 330                 335

Ser Glu Leu Glu Asn Ala Phe Ile Arg Pro Pro His Leu Phe Glu Arg
            340                 345                 350

Leu Asn Arg Leu Thr Ile Ser Arg Asn Arg Tyr Thr Ala Pro Thr Thr
        355                 360                 365

Asn Ser Phe Leu Asp Tyr Trp Ser Gly His Thr Leu Gln Ser Gln His
    370                 375                 380

Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Arg Ala Ile Asp Ser
                405                 410                 415

Arg Ala Arg Asn Phe Gly Asn Leu Tyr Ala Asn Leu Tyr Gly Val Ser
            420                 425                 430

Ser Leu Asn Ile Phe Pro Thr Gly Val Met Ser Glu Ile Thr Asn Ala
        435                 440                 445

Ala Asn Thr Cys Arg Gln Asp Leu Thr Thr Thr Glu Glu Leu Pro Leu
    450                 455                 460

Glu Asn Asn Asn Phe Asn Leu Leu Ser His Val Thr Phe Leu Arg Phe
465                 470                 475                 480

Asn Thr Thr Gln Gly Gly Pro Leu Ala Thr Leu Gly Phe Val Pro Thr
                485                 490                 495

Tyr Val Trp Thr Arg Glu Asp Val Asp Phe Thr Asn Thr Ile Thr Ala
            500                 505                 510

Asp Arg Ile Thr Gln Leu Pro Trp Val Lys Ala Ser Glu Ile Gly Gly
        515                 520                 525

Gly Thr Thr Val Val Lys Gly Pro Gly Phe Thr Gly Gly Asp Ile Leu
    530                 535                 540

Arg Arg Thr Asp Gly Gly Ala Val Gly Thr Ile Arg Ala Asn Val Asn
545                 550                 555                 560

Ala Pro Leu Thr Gln Gln Tyr Arg Ile Arg Leu Arg Tyr Ala Ser Thr
                565                 570                 575

Thr Ser Phe Val Val Asn Leu Phe Val Asn Asn Ser Ala Ala Gly Phe
            580                 585                 590

Thr Leu Pro Ser Thr Met Ala Gln Asn Gly Ser Leu Thr Tyr Glu Ser
        595                 600                 605
```

-continued

Phe Asn Thr Leu Glu Val Thr His Thr Ile Arg Phe Ser Gln Ser Asp
610 615 620

Thr Thr Leu Arg Leu Asn Ile Phe Pro Ser Ile Ser Gly Gln Glu Val
625 630 635 640

Tyr Val Asp Lys Leu Glu Ile Val Pro Ile Asn Pro Thr Arg Glu Ala
645 650 655

Glu Glu Asp Leu Glu Asp Ala Lys Lys Ala Val Ala Ser Leu Phe Thr
660 665 670

Arg Thr Arg Asp Gly Leu Gln Val Asn Val Thr Asp Tyr Gln Val Asp
675 680 685

Gln Ala Ala Asn Leu Val Ser Cys Leu Ser Asp Glu Gln Tyr Gly His
690 695 700

Asp Lys Lys Met Leu Leu Glu Ala Val Arg Ala Ala Lys Arg Leu Ser
705 710 715 720

Arg Glu Arg Asn Leu Leu Gln Asp Pro Asp Phe Asn Glu Ile Asn Ser
725 730 735

Thr Glu Glu Asn Gly Trp Lys Ala Ser Asn Gly Val Thr Ile Ser Glu
740 745 750

Gly Gly Pro Phe Phe Lys Gly Arg Ala Leu Gln Leu Ala Ser Ala Arg
755 760 765

Glu Asn Tyr Pro Thr Tyr Ile Tyr Gln Lys Val Asp Ala Ser Thr Leu
770 775 780

Lys Pro Tyr Thr Arg Tyr Lys Leu Asp Gly Phe Val Gln Ser Ser Gln
785 790 795 800

Asp Leu Glu Ile Asp Leu Ile His His His Lys Val His Leu Val Lys
805 810 815

Asn Val Pro Asp Asn Leu Val Ser Asp Thr Tyr Ser Asp Gly Ser Cys
820 825 830

Ser Gly Ile Asn Arg Cys Glu Glu Gln His Gln Val Asp Val Gln Leu
835 840 845

Asp Ala Glu Asp His Pro Lys Asp Cys Cys Glu Ala Ala Gln Thr His
850 855 860

Glu Phe Ser Ser Tyr Ile His Thr Gly Asp Leu Asn Ala Ser Val Asp
865 870 875 880

Gln Gly Ile Trp Val Val Leu Gln Val Arg Thr Thr Asp Gly Tyr Ala
885 890 895

Thr Leu Gly Asn Leu Glu Leu Val Glu Val Gly Pro Leu Ser Gly Glu
900 905 910

Ser Leu Glu Arg Glu Gln Arg Asp Asn Ala Lys Trp Asn Glu Glu Val
915 920 925

Gly Arg Lys Arg Ala Glu Thr Asp Arg Ile Tyr Gln Asp Ala Lys Gln
930 935 940

Ala Ile Asn His Leu Phe Val Asp Tyr Gln Asp Gln Gln Leu Ser Pro
945 950 955 960

Glu Val Gly Met Ala Asp Ile Ile Asp Ala Gln Asn Leu Ile Ala Ser
965 970 975

Ile Ser Asp Val Tyr Ser Asp Ala Val Leu Gln Ile Pro Gly Ile Asn
980 985 990

Tyr Glu Met Tyr Thr Glu Leu Ser Asn Arg Leu Gln Gln Ala Ser Tyr
995 1000 1005

Leu Tyr Thr Ser Arg Asn Val Val Gln Asn Gly Asp Phe Asn Ser Gly
1010 1015 1020

-continued

```
Leu Asp Ser Trp Asn Ala Thr Thr Asp Thr Ala Val Gln Gln Asp Gly
1025                1030                1035                1040

Asn Met His Phe Leu Val Leu Ser His Trp Asp Ala Gln Val Ser Gln
                1045                1050                1055

Gln Phe Arg Val Gln Pro Asn Cys Lys Tyr Val Leu Arg Val Thr Ala
            1060                1065                1070

Lys Lys Val Gly Asn Gly Asp Gly Tyr Val Thr Ile Gln Asp Gly Ala
        1075                1080                1085

His His Arg Glu Thr Leu Thr Phe Asn Ala Cys Asp Tyr Asp Val Asn
    1090                1095                1100

Gly Thr His Val Asn Asp Asn Ser Tyr Ile Thr Lys Glu Leu Val Phe
1105                1110                1115                1120

Tyr Pro Lys Thr Glu His Met Trp Val Glu Val Ser Glu Thr Glu Gly
                1125                1130                1135

Thr Phe Tyr Ile Asp Ser Ile Glu Phe Ile Glu Thr Gln Glu
            1140                1145                1150


<210> SEQ ID NO 19
<211> LENGTH: 1150
<212> TYPE: PRT
<213> ORGANISM: Bacillus thuringiensis B-Hm-16

<400> SEQUENCE: 19

Met Asn Arg Asn Asn Pro Asn Glu Tyr Glu Ile Ile Asp Ala Pro Tyr
 1               5                  10                  15

Cys Gly Cys Pro Ser Asp Asp Asp Val Arg Tyr Pro Leu Ala Ser Asp
            20                  25                  30

Pro Asn Ala Ala Phe Gln Asn Met Asn Tyr Lys Glu Tyr Leu Gln Thr
        35                  40                  45

Tyr Asp Gly Asp Tyr Thr Gly Ser Leu Ile Asn Pro Asn Leu Ser Ile
    50                  55                  60

Asn Pro Arg Asp Val Leu Gln Thr Gly Ile Asn Ile Val Gly Arg Ile
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asp Gln Lys Ile Ser
        115                 120                 125

Ala Gln Val Val Arg Asn Ala Leu Asp Asp Leu Thr Gly Leu His Asp
    130                 135                 140

Tyr Tyr Glu Glu Tyr Leu Ala Ala Leu Glu Glu Trp Leu Glu Arg Pro
145                 150                 155                 160

Asn Gly Ala Arg Ala Asn Leu Val Thr Gln Arg Phe Glu Asn Leu His
                165                 170                 175

Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Gln Gln Gly Gln Ile Asn Leu Tyr Phe Asn Ala Gln Gln Glu
225                 230                 235                 240

Arg Thr Arg Ile Tyr Thr Asn His Cys Val Glu Thr Tyr Asn Arg Gly
                245                 250                 255
```

-continued

```
Leu Glu Asp Val Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
        275                 280                 285

Phe Pro Phe Tyr Asn Val Arg Gln Tyr Pro Asn Gly Ala Asn Pro Gln
    290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
                325                 330                 335

Ser Glu Leu Glu Asn Ala Phe Ile Arg Pro Pro His Leu Phe Glu Arg
            340                 345                 350

Leu Asn Arg Leu Thr Ile Ser Arg Asn Arg Tyr Thr Ala Pro Thr Thr
        355                 360                 365

Asn Ser Phe Leu Asp Tyr Trp Ser Gly His Thr Leu Gln Ser Gln His
    370                 375                 380

Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Arg Ala Ile Asp Ser
                405                 410                 415

Arg Ala Arg Asn Phe Gly Asn Leu Tyr Ala Asn Leu Tyr Gly Val Ser
            420                 425                 430

Ser Leu Asn Ile Phe Pro Thr Gly Val Met Ser Glu Ile Thr Asn Ala
        435                 440                 445

Ala Asn Thr Cys Arg Gln Asp Leu Thr Thr Thr Glu Glu Leu Pro Leu
    450                 455                 460

Glu Asn Asn Asn Phe Asn Leu Leu Ser His Val Thr Phe Leu Arg Phe
465                 470                 475                 480

Asn Thr Thr Gln Gly Gly Pro Leu Ala Thr Leu Gly Phe Val Pro Thr
                485                 490                 495

Tyr Val Trp Thr Arg Glu Asp Val Asp Phe Thr Asn Thr Ile Thr Ala
            500                 505                 510

Asp Arg Ile Thr Gln Leu Pro Trp Val Lys Ala Ser Glu Ile Gly Gly
        515                 520                 525

Gly Thr Thr Val Val Lys Gly Pro Gly Phe Thr Gly Gly Asp Ile Leu
    530                 535                 540

Arg Arg Thr Asp Gly Gly Ala Val Gly Thr Ile Arg Ala Asn Val Asn
545                 550                 555                 560

Ala Pro Leu Thr Gln Gln Tyr Arg Ile Arg Leu Arg Tyr Ala Ser Thr
                565                 570                 575

Thr Ser Phe Val Val Asn Leu Phe Val Asn Asn Ser Ala Ala Gly Phe
            580                 585                 590

Thr Leu Pro Ser Thr Met Ala Gln Asn Gly Ser Leu Thr Tyr Glu Ser
        595                 600                 605

Phe Asn Thr Leu Glu Val Thr His Thr Ile Arg Phe Ser Gln Ser Asp
    610                 615                 620

Thr Thr Leu Arg Leu Asn Ile Phe Pro Ser Ile Ser Gly Gln Glu Val
625                 630                 635                 640

Tyr Val Asp Lys Leu Glu Ile Val Pro Ile Asn Pro Thr Arg Glu Ala
                645                 650                 655

Glu Glu Asp Leu Glu Asp Ala Lys Lys Ala Val Ala Ser Leu Phe Thr
            660                 665                 670
```

-continued

```
Arg Thr Arg Asp Gly Leu Gln Val Asn Val Thr Asp Tyr Gln Val Asp
        675                 680                 685

Gln Ala Ala Asn Leu Val Ser Cys Leu Ser Asp Glu Gln Tyr Gly His
    690                 695                 700

Asp Lys Lys Met Leu Leu Glu Ala Val Arg Ala Ala Lys Arg Leu Ser
705                 710                 715                 720

Arg Glu Arg Asn Leu Leu Gln Asp Pro Asp Phe Asn Glu Ile Asn Ser
                725                 730                 735

Thr Glu Glu Asn Gly Trp Lys Ala Ser Asn Gly Val Thr Ile Ser Glu
            740                 745                 750

Gly Gly Pro Phe Phe Lys Gly Arg Ala Leu Gln Leu Ala Ser Ala Arg
        755                 760                 765

Glu Asn Tyr Pro Thr Tyr Ile Tyr Gln Lys Val Asp Ala Ser Thr Leu
    770                 775                 780

Lys Pro Tyr Thr Arg Tyr Lys Leu Asp Gly Phe Val Gln Ser Ser Gln
785                 790                 795                 800

Asp Leu Glu Ile Asp Leu Ile His His His Lys Val His Leu Val Lys
                805                 810                 815

Asn Val Pro Asp Asn Leu Val Ser Asp Thr Tyr Ser Asp Gly Ser Cys
            820                 825                 830

Ser Gly Ile Asn Arg Cys Glu Glu Gln His Gln Val Asp Val Gln Leu
        835                 840                 845

Asp Ala Glu Asp His Pro Lys Asp Cys Cys Glu Ala Ala Gln Thr His
    850                 855                 860

Glu Phe Ser Ser Tyr Ile His Thr Gly Asp Leu Asn Ala Ser Val Asp
865                 870                 875                 880

Gln Gly Ile Trp Val Val Leu Gln Val Arg Thr Thr Asp Gly Tyr Ala
                885                 890                 895

Thr Leu Gly Asn Leu Glu Leu Val Glu Val Gly Pro Leu Ser Gly Glu
            900                 905                 910

Ser Leu Glu Arg Glu Gln Arg Asp Asn Ala Lys Trp Asn Glu Glu Val
        915                 920                 925

Gly Arg Lys Arg Ala Glu Thr Asp Arg Ile Tyr Gln Asp Ala Lys Gln
    930                 935                 940

Ala Ile Asn His Leu Phe Val Asp Tyr Gln Asp Gln Gln Leu Ser Pro
945                 950                 955                 960

Glu Val Gly Met Ala Asp Ile Ile Asp Ala Gln Asn Leu Ile Ala Ser
                965                 970                 975

Ile Ser Asp Val Tyr Ser Asp Ala Val Leu Gln Ile Pro Gly Ile Asn
            980                 985                 990

Tyr Glu Met Tyr Thr Glu Leu Ser Asn Arg Leu Gln Gln Ala Ser Tyr
        995                 1000                1005

Leu Tyr Thr Ser Arg Asn Val Val Gln Asn Gly Asp Phe Asn Ser Gly
    1010                1015                1020

Leu Asp Ser Trp Asn Ala Thr Thr Asp Thr Ala Val Gln Gln Asp Gly
1025                1030                1035                1040

Asn Met His Phe Leu Val Leu Ser His Trp Asp Ala Gln Val Ser Gln
                1045                1050                1055

Gln Phe Arg Val Gln Pro Asn Cys Lys Tyr Val Leu Arg Val Thr Ala
            1060                1065                1070

Lys Lys Val Gly Asn Gly Asp Gly Tyr Val Thr Ile Gln Asp Gly Ala
        1075                1080                1085

His His Arg Glu Thr Leu Thr Phe Asn Ala Cys Asp Tyr Asp Val Asn
```

-continued

```
    1090                1095                1100

Gly Thr His Val Asn Asp Asn Ser Tyr Ile Thr Lys Glu Leu Val Phe
1105                1110                1115                1120

Tyr Pro Lys Thr Glu His Met Trp Val Glu Val Ser Glu Thr Glu Gly
                1125                1130                1135

Thr Phe Tyr Ile Asp Ser Ile Glu Phe Ile Glu Thr Gln Glu
            1140                1145                1150


<210> SEQ ID NO 20
<211> LENGTH: 1157
<212> TYPE: PRT
<213> ORGANISM: Bacillus thuringiensis tolworthi

<400> SEQUENCE: 20

Met Asn Arg Asn Asn Gln Asn Glu Tyr Glu Ile Ile Asp Ala Pro His
 1               5                  10                  15

Cys Gly Cys Pro Ser Asp Asp Asp Val Arg Tyr Pro Leu Ala Ser Asp
            20                  25                  30

Pro Asn Ala Ala Leu Gln Asn Met Asn Tyr Lys Asp Tyr Leu Gln Met
        35                  40                  45

Thr Asp Glu Asp Tyr Thr Asp Ser Tyr Ile Asn Pro Ser Leu Ser Ile
    50                  55                  60

Ser Gly Arg Asp Ala Val Gln Thr Ala Leu Thr Val Val Gly Arg Ile
65                  70                  75                  80

Leu Gly Ala Leu Gly Val Pro Phe Ser Gly Gln Ile Val Ser Phe Tyr
                85                  90                  95

Gln Phe Leu Leu Asn Thr Leu Trp Pro Val Asn Asp Thr Ala Ile Trp
            100                 105                 110

Glu Ala Phe Met Arg Gln Val Glu Glu Leu Val Asn Gln Gln Ile Thr
        115                 120                 125

Glu Phe Ala Arg Asn Gln Ala Leu Ala Arg Leu Gln Gly Leu Gly Asp
    130                 135                 140

Ser Phe Asn Val Tyr Gln Arg Ser Leu Gln Asn Trp Leu Ala Asp Arg
145                 150                 155                 160

Asn Asp Thr Arg Asn Leu Ser Val Val Arg Ala Gln Phe Ile Ala Leu
                165                 170                 175

Asp Leu Asp Phe Val Asn Ala Ile Pro Leu Phe Ala Val Asn Gly Gln
            180                 185                 190

Gln Val Pro Leu Leu Ser Val Tyr Ala Gln Ala Val Asn Leu His Leu
        195                 200                 205

Leu Leu Leu Lys Asp Ala Ser Leu Phe Gly Glu Gly Trp Gly Phe Thr
    210                 215                 220

Gln Gly Glu Ile Ser Thr Tyr Tyr Asp Arg Gln Leu Glu Leu Thr Ala
225                 230                 235                 240

Lys Tyr Thr Asn Tyr Cys Glu Thr Trp Tyr Asn Thr Gly Leu Asp Arg
                245                 250                 255

Leu Arg Gly Thr Asn Thr Glu Ser Trp Leu Arg Tyr His Gln Phe Arg
            260                 265                 270

Arg Glu Met Thr Leu Val Val Leu Asp Val Val Ala Leu Phe Pro Tyr
        275                 280                 285

Tyr Asp Val Arg Leu Tyr Pro Thr Gly Ser Asn Pro Gln Leu Thr Arg
    290                 295                 300

Glu Val Tyr Thr Asp Pro Ile Val Phe Asn Pro Pro Ala Asn Val Gly
305                 310                 315                 320
```

-continued

```
Leu Cys Arg Arg Trp Gly Thr Asn Pro Tyr Asn Thr Phe Ser Glu Leu
                325                 330                 335

Glu Asn Ala Phe Ile Arg Pro Pro His Leu Phe Asp Arg Leu Asn Ser
            340                 345                 350

Leu Thr Ile Ser Ser Asn Arg Phe Pro Val Ser Ser Asn Phe Met Asp
        355                 360                 365

Tyr Trp Ser Gly His Thr Leu Arg Arg Ser Tyr Leu Asn Asp Ser Ala
    370                 375                 380

Val Gln Glu Asp Ser Tyr Gly Leu Ile Thr Thr Thr Arg Ala Thr Ile
385                 390                 395                 400

Asn Pro Gly Val Asp Gly Thr Asn Arg Ile Glu Ser Thr Ala Val Asp
                405                 410                 415

Phe Arg Ser Ala Leu Ile Gly Ile Tyr Gly Val Asn Arg Ala Ser Phe
            420                 425                 430

Val Pro Gly Gly Leu Phe Asn Gly Thr Thr Ser Pro Ala Asn Gly Gly
        435                 440                 445

Cys Arg Asp Leu Tyr Asp Thr Asn Asp Glu Leu Pro Pro Asp Glu Ser
    450                 455                 460

Thr Gly Ser Ser Thr His Arg Leu Ser His Val Thr Phe Phe Ser Phe
465                 470                 475                 480

Gln Thr Asn Gln Ala Gly Ser Ile Ala Asn Ala Gly Ser Val Pro Thr
                485                 490                 495

Tyr Val Trp Thr Arg Arg Asp Val Asp Leu Asn Asn Thr Ile Thr Pro
            500                 505                 510

Asn Arg Ile Thr Gln Leu Pro Leu Val Lys Ala Ser Ala Pro Val Ser
        515                 520                 525

Gly Thr Thr Val Leu Lys Gly Pro Gly Phe Thr Gly Gly Gly Ile Leu
    530                 535                 540

Arg Arg Thr Thr Asn Gly Thr Phe Gly Thr Leu Arg Val Thr Val Asn
545                 550                 555                 560

Ser Pro Leu Thr Gln Gln Tyr Arg Leu Arg Val Arg Phe Ala Ser Thr
                565                 570                 575

Gly Asn Phe Ser Ile Arg Val Leu Arg Gly Gly Val Ser Ile Gly Asp
            580                 585                 590

Val Arg Leu Gly Ser Thr Met Asn Arg Gly Gln Glu Leu Thr Tyr Glu
        595                 600                 605

Ser Phe Phe Thr Arg Glu Phe Thr Thr Thr Gly Pro Phe Asn Pro Pro
    610                 615                 620

Phe Thr Phe Thr Gln Ala Gln Glu Ile Leu Thr Val Asn Ala Glu Gly
625                 630                 635                 640

Val Ser Thr Gly Gly Glu Tyr Tyr Ile Asp Arg Ile Glu Ile Val Pro
                645                 650                 655

Val Asn Pro Ala Arg Glu Ala Glu Glu Asp Leu Glu Ala Ala Lys Lys
            660                 665                 670

Ala Val Ala Ser Leu Phe Thr Arg Thr Arg Asp Gly Leu Gln Val Asn
        675                 680                 685

Val Thr Asp Tyr Gln Val Asp Gln Ala Ala Asn Leu Val Ser Cys Leu
    690                 695                 700

Ser Asp Glu Gln Tyr Gly His Asp Lys Lys Met Leu Leu Glu Ala Val
705                 710                 715                 720

Arg Ala Ala Lys Arg Leu Ser Arg Glu Arg Asn Leu Leu Gln Asp Pro
                725                 730                 735

Asp Phe Asn Thr Ile Asn Ser Thr Glu Glu Asn Gly Trp Lys Ala Ser
```

-continued

```
            740                 745                 750

Asn Gly Val Thr Ile Ser Glu Gly Gly Pro Phe Phe Lys Gly Arg Ala
        755                 760                 765

Leu Gln Leu Ala Ser Ala Arg Glu Asn Tyr Pro Thr Tyr Ile Tyr Gln
    770                 775                 780

Lys Val Asp Ala Ser Val Leu Lys Pro Tyr Thr Arg Tyr Arg Leu Asp
785                 790                 795                 800

Gly Phe Val Lys Ser Ser Gln Asp Leu Glu Ile Asp Leu Ile His His
                805                 810                 815

His Lys Val His Leu Val Lys Asn Val Pro Asp Asn Leu Val Ser Asp
            820                 825                 830

Thr Tyr Ser Asp Gly Ser Cys Ser Gly Ile Asn Arg Cys Asp Glu Gln
        835                 840                 845

His Gln Val Asp Met Gln Leu Asp Ala Glu His His Pro Met Asp Cys
    850                 855                 860

Cys Glu Ala Ala Gln Thr His Glu Phe Ser Ser Tyr Ile Asn Thr Gly
865                 870                 875                 880

Asp Leu Asn Ala Ser Val Asp Gln Gly Ile Trp Val Val Leu Lys Val
                885                 890                 895

Arg Thr Thr Asp Gly Tyr Ala Thr Leu Gly Asn Leu Glu Leu Val Glu
            900                 905                 910

Val Gly Pro Leu Ser Gly Glu Ser Leu Glu Arg Glu Gln Arg Asp Asn
        915                 920                 925

Ala Lys Trp Asn Ala Glu Leu Gly Arg Lys Arg Ala Glu Ile Asp Arg
    930                 935                 940

Val Tyr Leu Ala Ala Lys Gln Ala Ile Asn His Leu Phe Val Asp Tyr
945                 950                 955                 960

Gln Asp Gln Gln Leu Asn Pro Glu Ile Gly Leu Ala Glu Ile Asn Glu
                965                 970                 975

Ala Ser Asn Leu Val Glu Ser Ile Ser Gly Val Tyr Ser Asp Thr Leu
            980                 985                 990

Leu Gln Ile Pro Gly Ile Asn Tyr Glu Ile Tyr Thr Glu Leu Ser Asp
        995                 1000                1005

Arg Leu Gln Gln Ala Ser Tyr Leu Tyr Thr Ser Arg Asn Ala Val Gln
    1010                1015                1020

Asn Gly Asp Phe Asn Ser Gly Leu Asp Ser Trp Asn Thr Thr Met Asp
1025                1030                1035                1040

Ala Ser Val Gln Gln Asp Gly Asn Met His Phe Leu Val Leu Ser His
                1045                1050                1055

Trp Asp Ala Gln Val Ser Gln Gln Leu Arg Val Asn Pro Asn Cys Lys
            1060                1065                1070

Tyr Val Leu Arg Val Thr Ala Arg Lys Val Gly Gly Gly Asp Gly Tyr
        1075                1080                1085

Val Thr Ile Arg Asp Gly Ala His His Gln Glu Thr Leu Thr Phe Asn
    1090                1095                1100

Ala Cys Asp Tyr Asp Val Asn Gly Thr Tyr Val Asn Asp Asn Ser Tyr
1105                1110                1115                1120

Ile Thr Glu Glu Val Val Phe Tyr Pro Glu Thr Lys His Met Trp Val
                1125                1130                1135

Glu Val Ser Glu Ser Glu Gly Ser Phe Tyr Ile Asp Ser Ile Glu Phe
            1140                1145                1150

Ile Glu Thr Gln Glu
        1155
```

-continued

<210> SEQ ID NO 21
<211> LENGTH: 1144
<212> TYPE: PRT
<213> ORGANISM: Bacillus thuringiensis galleriae

<400> SEQUENCE: 21

```
Val Phe Glu Leu Lys Thr Cys Ile Trp His Ala Phe Phe Leu Thr Lys
 1               5                  10                  15

Leu Ser Ser Tyr Lys Asp Tyr Leu Lys Met Ser Glu Gly Asp Tyr Ile
            20                  25                  30

Asp Ser Tyr Ile Asn Pro Gly Asn Val Arg Thr Gly Leu Gln Thr Gly
        35                  40                  45

Ile Asp Ile Val Ala Val Val Val Gly Ala Leu Gly Gly Pro Val Gly
    50                  55                  60

Gly Ile Leu Thr Gly Phe Leu Ser Thr Leu Phe Gly Phe Leu Trp Pro
65                  70                  75                  80

Ser Asn Asp Gln Ala Val Trp Glu Ala Phe Ile Glu Gln Met Glu Glu
                85                  90                  95

Leu Ile Glu Gln Arg Ile Ser Asp Gln Val Val Arg Thr Ala Leu Asp
            100                 105                 110

Asp Leu Thr Gly Ile Gln Asn Tyr Tyr Asn Gln Tyr Leu Ile Ala Leu
        115                 120                 125

Lys Glu Trp Glu Glu Arg Pro Asn Gly Val Arg Ala Asn Leu Val Leu
    130                 135                 140

Gln Arg Phe Glu Ile Leu His Ala Leu Phe Val Ser Ser Met Pro Ser
145                 150                 155                 160

Phe Gly Ser Gly Pro Gly Ser Gln Arg Phe Gln Ala Gln Leu Leu Val
                165                 170                 175

Val Tyr Ala Gln Ala Ala Asn Leu His Leu Leu Leu Leu Ala Asp Ala
            180                 185                 190

Glu Lys Tyr Gly Ala Arg Trp Gly Leu Arg Glu Ser Gln Ile Gly Asn
        195                 200                 205

Leu Tyr Phe Asn Glu Leu Gln Thr Arg Thr Arg Asp Tyr Thr Asn His
    210                 215                 220

Cys Val Asn Ala Tyr Asn Asn Gly Leu Ala Gly Leu Arg Gly Thr Ser
225                 230                 235                 240

Ala Glu Ser Trp Leu Lys Tyr His Gln Phe Arg Arg Glu Ala Thr Leu
                245                 250                 255

Met Ala Met Asp Leu Ile Ala Leu Phe Pro Tyr Tyr Asn Thr Arg Arg
            260                 265                 270

Tyr Pro Ile Ala Val Asn Pro Gln Leu Thr Arg Glu Val Tyr Thr Asp
        275                 280                 285

Pro Leu Gly Val Pro Ser Glu Glu Ser Ser Leu Phe Pro Glu Leu Arg
    290                 295                 300

Cys Leu Arg Trp Gln Glu Thr Ser Ala Met Thr Phe Ser Asn Leu Glu
305                 310                 315                 320

Asn Ala Ile Ile Ser Ser Pro His Leu Phe Asp Thr Ile Asn Asn Leu
                325                 330                 335

Met Ile Tyr Thr Gly Ser Phe Ser Val His Leu Thr Asn Gln Leu Ile
            340                 345                 350

Glu Gly Trp Ile Gly His Ser Val Thr Ser Ser Leu Leu Ala Ser Gly
        355                 360                 365

Pro Thr Thr Val Leu Arg Arg Asn Tyr Gly Ser Thr Thr Ser Ile Val
```

-continued

```
    370                 375                 380

Asn Tyr Phe Ser Phe Asn Asp Arg Asp Val Tyr Gln Ile Asn Thr Arg
385                 390                 395                 400

Ser His Thr Gly Leu Gly Phe Gln Asn Ala Pro Leu Phe Gly Ile Thr
                405                 410                 415

Arg Ala Gln Phe Tyr Pro Gly Gly Thr Tyr Ser Val Thr Gln Arg Asn
            420                 425                 430

Ala Leu Thr Cys Glu Gln Asn Tyr Asn Ser Ile Asp Glu Leu Pro Ser
        435                 440                 445

Leu Asp Pro Asn Glu Pro Ile Ser Arg Ser Tyr Ser His Arg Leu Ser
    450                 455                 460

His Ile Thr Ser Tyr Leu His Arg Val Leu Thr Ile Asp Gly Ile Asn
465                 470                 475                 480

Ile Tyr Ser Gly Asn Leu Pro Thr Tyr Val Trp Thr His Arg Asp Val
                485                 490                 495

Asp Leu Thr Asn Thr Ile Thr Ala Asp Arg Ile Thr Gln Leu Pro Leu
            500                 505                 510

Val Lys Ser Phe Glu Ile Pro Ala Gly Thr Thr Val Val Arg Gly Pro
        515                 520                 525

Gly Phe Thr Gly Gly Asp Ile Leu Arg Arg Thr Gly Val Gly Thr Phe
    530                 535                 540

Gly Thr Ile Arg Val Arg Thr Thr Ala Pro Leu Thr Gln Arg Tyr Arg
545                 550                 555                 560

Ile Arg Phe Arg Phe Ala Ser Thr Thr Asn Leu Phe Ile Gly Ile Arg
                565                 570                 575

Val Gly Asp Arg Gln Val Asn Tyr Phe Asp Phe Gly Arg Thr Met Asn
            580                 585                 590

Arg Gly Asp Glu Leu Arg Tyr Glu Ser Phe Ala Thr Arg Glu Phe Thr
        595                 600                 605

Thr Asp Phe Asn Phe Arg Gln Pro Gln Glu Leu Ile Ser Val Phe Ala
    610                 615                 620

Asn Ala Phe Ser Ala Gly Gln Glu Val Tyr Phe Asp Arg Ile Glu Ile
625                 630                 635                 640

Ile Pro Val Asn Pro Ala Arg Glu Ala Lys Glu Asp Leu Glu Ala Ala
                645                 650                 655

Lys Lys Ala Val Ala Ser Leu Phe Thr Arg Thr Arg Asp Gly Leu Gln
            660                 665                 670

Val Asn Val Lys Asp Tyr Gln Val Asp Gln Ala Ala Asn Leu Val Ser
        675                 680                 685

Cys Leu Ser Asp Glu Gln Tyr Gly Tyr Asp Lys Lys Met Leu Leu Glu
    690                 695                 700

Ala Val Arg Ala Ala Lys Arg Leu Ser Arg Glu Arg Asn Leu Leu Gln
705                 710                 715                 720

Asp Pro Asp Phe Asn Thr Ile Asn Ser Thr Glu Glu Asn Gly Trp Lys
                725                 730                 735

Ala Ser Asn Gly Val Thr Ile Ser Glu Gly Gly Pro Phe Tyr Lys Gly
            740                 745                 750

Arg Ala Leu Gln Leu Ala Ser Ala Arg Glu Asn Tyr Pro Thr Tyr Ile
        755                 760                 765

Tyr Gln Lys Val Asp Ala Ser Glu Leu Lys Pro Tyr Thr Arg Tyr Arg
    770                 775                 780

Ser Asp Gly Phe Val Lys Ser Ser Gln Asp Leu Glu Ile Asp Leu Ile
785                 790                 795                 800
```

-continued

```
His His His Lys Val His Leu Val Lys Asn Val Pro Asp Asn Leu Val
                805                 810                 815

Ser Asp Thr Tyr Pro Asp Asp Ser Cys Ser Gly Ile Asn Arg Cys Gln
            820                 825                 830

Glu Gln Gln Met Val Asn Ala Gln Leu Glu Thr Glu His His His Pro
        835                 840                 845

Met Asp Cys Cys Glu Ala Ala Gln Thr His Glu Phe Ser Ser Tyr Ile
    850                 855                 860

Asp Thr Gly Asp Leu Asn Ser Ser Val Asp Gln Gly Ile Trp Ala Ile
865                 870                 875                 880

Phe Lys Val Arg Thr Thr Asp Gly Tyr Ala Thr Leu Gly Asn Leu Glu
                885                 890                 895

Leu Val Glu Val Gly Pro Leu Ser Gly Glu Ser Leu Glu Arg Glu Gln
            900                 905                 910

Arg Asp Asn Thr Lys Trp Ser Ala Glu Leu Gly Arg Lys Arg Ala Glu
        915                 920                 925

Thr Asp Arg Val Tyr Gln Asp Ala Lys Gln Ser Ile Asn His Leu Phe
    930                 935                 940

Val Asp Tyr Gln Asp Gln Gln Leu Asn Pro Glu Ile Gly Met Ala Asp
945                 950                 955                 960

Ile Met Asp Ala Gln Asn Leu Val Ala Ser Ile Ser Asp Val Tyr Ser
                965                 970                 975

Asp Ala Val Leu Gln Ile Pro Gly Ile Asn Tyr Glu Ile Tyr Thr Glu
            980                 985                 990

Leu Ser Asn Arg Leu Gln Gln Ala Ser Tyr Leu Tyr Thr Ser Arg Asn
        995                 1000                1005

Ala Val Gln Asn Gly Asp Phe Asn Asn Gly Leu Asp Ser Trp Asn Ala
    1010                1015                1020

Thr Ala Gly Ala Ser Val Gln Gln Asp Gly Asn Thr His Phe Leu Val
1025                1030                1035                1040

Leu Ser His Trp Asp Ala Gln Val Ser Gln Gln Phe Arg Val Gln Pro
                1045                1050                1055

Asn Cys Lys Tyr Val Leu Arg Val Thr Ala Glu Lys Val Gly Gly Gly
            1060                1065                1070

Asp Gly Tyr Val Thr Ile Arg Asp Gly Ala His His Thr Glu Thr Leu
        1075                1080                1085

Thr Phe Asn Ala Cys Asp Tyr Asp Ile Asn Gly Thr Tyr Val Thr Asp
    1090                1095                1100

Asn Thr Tyr Leu Thr Lys Glu Val Ile Phe Tyr Ser His Thr Glu His
1105                1110                1115                1120

Met Trp Val Glu Val Asn Glu Thr Glu Gly Ala Phe His Ile Asp Ser
                1125                1130                1135

Ile Glu Phe Val Glu Thr Glu Lys
            1140
```

```
<210> SEQ ID NO 22
<211> LENGTH: 1205
<212> TYPE: PRT
<213> ORGANISM: Artificial Sequence
<220> FEATURE:
<223> OTHER INFORMATION: consensus sequence; "Xaa" is any amino acid

<400> SEQUENCE: 22

Met Asn Arg Asn Asn Gln Asn Glu Tyr Glu Ile Ile Asp Ala Pro Xaa
 1               5                  10                  15
```

-continued

```
Cys Gly Cys Pro Ser Asp Asp Val Val Lys Tyr Pro Leu Ala Asp Asp
            20                  25                  30

Pro Asn Ala Gly Leu Leu Asn Gln Asn Met Asn Tyr Lys Glu Tyr Leu
        35                  40                  45

Gln Thr Tyr Asp Gly Asp Tyr Thr Asp Ser Leu Ile Asn Pro Asn Leu
    50                  55                  60

Ser Ile Asn Gly Arg Asp Val Leu Gln Thr Gly Ile Asn Ile Val Gly
65                  70                  75                  80

Arg Xaa Leu Gly Phe Leu Gly Val Pro Phe Ala Gly Gln Leu Val Thr
                85                  90                  95

Phe Tyr Thr Phe Leu Leu Asn Gln Leu Trp Pro Thr Asn Asp Asn Ala
            100                 105                 110

Val Trp Glu Ala Phe Met Ala Gln Ile Glu Glu Leu Ile Asp Gln Arg
        115                 120                 125

Ile Ser Glu Xaa Val Val Xaa Asn Ala Leu Asp Asp Leu Thr Gly Leu
    130                 135                 140

His Asp Xaa Tyr Asn Leu Tyr Leu Glu Ala Leu Glu Glu Trp Leu Glu
145                 150                 155                 160

Arg Pro Asn Gly Ala Arg Ala Ala Asn Leu Val Phe Gln Arg Phe Glu
                165                 170                 175

Ile Leu Asp Ser Leu Phe Val Gln Phe Met Pro Ser Phe Gly Leu Thr
            180                 185                 190

Gly Pro Gly Ser Leu Ala Arg Gln Asn Tyr Ala Val Ala Leu Leu Thr
        195                 200                 205

Val Tyr Ala Gln Ala Ala Asn Leu His Leu Leu Leu Leu Lys Asp Ala
    210                 215                 220

Glu Ile Tyr Gly Ala Arg Trp Gly Leu Asn Gln Gly Gln Ile Phe Asn
225                 230                 235                 240

Leu Tyr Xaa Xaa Arg Gln Gln Glu Arg Thr Xaa Ile Tyr Thr Asn His
                245                 250                 255

Cys Val Thr Thr Tyr Asn Arg Gly Leu Xaa Glu Leu Arg Gln Arg Gly
            260                 265                 270

Thr Asn Thr Glu Ser Trp Leu Asn Tyr His Gln Phe Arg Arg Glu Met
        275                 280                 285

Thr Leu Met Ala Met Asp Leu Val Ala Leu Phe Pro Tyr Tyr Asn Val
    290                 295                 300

Arg Gln Tyr Pro Asn Gly Ala Asn Pro Gln Leu Thr Arg Glu Ile Tyr
305                 310                 315                 320

Thr Asp Pro Ile Val Phe Asn Pro Xaa Glu Pro Ala Asn Leu Arg Gly
                325                 330                 335

Gln Gly Leu Cys Arg Arg Trp Gly Asn Asn Pro Ala Phe Arg Asn Tyr
            340                 345                 350

Asn Thr Phe Ser Glu Leu Glu Asn Ala Phe Ile Arg Pro Arg Pro His
        355                 360                 365

Leu Phe Asp Arg Leu Asn Asn Leu Thr Ile Ser Xaa Asn Arg Xaa Thr
    370                 375                 380

Ala Pro Thr Xaa Ser Ser Phe Asp Arg Leu Asp Tyr Trp Ser Gly His
385                 390                 395                 400

Thr Leu Arg Ser Ser Tyr Ala Asn Asn Gln Phe Ser Thr Thr Gln Glu
                405                 410                 415

Thr Ser Tyr Gly Gln Ile Thr Ser Asn Xaa Thr Arg Leu Ile Asn Thr
            420                 425                 430
```

-continued

```
Gly Thr Asn Gly Xaa Asn Xaa Ile Asp Ser Arg Ala Cys Arg Asn Phe
        435                 440                 445

Gly Xaa Leu Xaa Ala Asn Leu Tyr Gly Val Ser Arg Ala Asn Phe Tyr
    450                 455                 460

Phe Pro Xaa Ser Glu Gly Val Met Ser Gly Ile Thr Ser Ala Ala Asn
465                 470                 475                 480

Thr Gly Xaa Xaa Xaa Xaa Cys Arg Gln Asp Leu Asn Thr Thr Asp Glu
                485                 490                 495

Leu Pro Leu Glu Asn Asn Asn Gly Pro Xaa Xaa Arg Ser Tyr Ser His
            500                 505                 510

Arg Leu Ser His Val Thr Phe Leu Arg Phe Asn Thr Thr Gln Gly Gly
        515                 520                 525

Ser Pro Leu Ala Thr Ser Gly Xaa Val Pro Thr Tyr Val Trp Thr Arg
    530                 535                 540

Arg Asp Val Asp Leu Asn Asn Thr Ile Thr Ala Asn Arg Ile Thr Gln
545                 550                 555                 560

Leu Pro Leu Val Lys Ala Ser Glu Xaa Gly Ser Gly Thr Thr Val Val
                565                 570                 575

Lys Gly Pro Gly Phe Thr Gly Gly Asp Ile Leu Arg Arg Thr Xaa Thr
            580                 585                 590

Gly Xaa Phe Gly Thr Ile Arg Val Ser Val Thr Gly Pro Leu Thr Gln
        595                 600                 605

Arg Tyr Arg Ile Arg Phe Arg Tyr Ala Ser Thr Thr Asp Phe Xaa Xaa
    610                 615                 620

Asp Phe Phe Val Thr Arg Gly Gly Thr Thr Ile Asn Asn Phe Arg Phe
625                 630                 635                 640

Pro Arg Thr Met Asn Arg Gly Gln Glu Ser Arg Tyr Glu Ser Tyr Arg
                645                 650                 655

Thr Xaa Glu Phe Thr Thr Ser Ile Arg Pro Xaa Xaa Pro Phe Asn Phe
            660                 665                 670

Thr Gln Ser Gln Asp Ile Ile Arg Thr Ser Ile Xaa Gln Gly Leu Ser
        675                 680                 685

Gly Asn Gly Glu Val Tyr Leu Asp Arg Ile Glu Ile Ile Pro Val Asn
    690                 695                 700

Pro Thr Arg Glu Ala Glu Glu Asp Leu Glu Ala Ala Lys Lys Ala Val
705                 710                 715                 720

Xaa Ala Ser Leu Phe Thr Arg Thr Arg Asp Gly Leu Gln Val Asn Val
                725                 730                 735

Thr Asp Tyr Gln Val Asp Gln Ala Ala Asn Leu Val Ser Cys Leu Ser
            740                 745                 750

Asp Glu Gln Tyr Gly His Asp Lys Lys Met Leu Leu Glu Ala Val Arg
        755                 760                 765

Ala Ala Lys Arg Leu Ser Arg Glu Arg Asn Leu Leu Gln Asp Pro Asp
    770                 775                 780

Phe Asn Thr Ile Asn Ser Thr Glu Glu Asn Gly Trp Lys Ala Ser Asn
785                 790                 795                 800

Gly Val Thr Ile Ser Glu Gly Gly Pro Phe Xaa Lys Gly Arg Ala Leu
                805                 810                 815

Gln Leu Ala Ser Ala Arg Glu Asn Tyr Pro Thr Tyr Ile Tyr Gln Lys
            820                 825                 830

Val Asp Ala Ser Glu Leu Lys Pro Tyr Thr Arg Tyr Arg Leu Asp Gly
        835                 840                 845

Phe Val Lys Ser Ser Gln Asp Leu Glu Ile Asp Leu Ile His His His
```

-continued 850 855 860

Lys Val His Leu Val Lys Asn Val Pro Asp Asn Leu Val Ser Asp Thr
865 870 875 880

Tyr Xaa Asp Xaa Ser Cys Ser Gly Ile Asn Arg Cys Glu Glu Gln Gln
885 890 895

Met Val Asn Ala Gln Leu Glu Thr Glu His His His Pro Met Asp Cys
900 905 910

Cys Glu Ala Ala Gln Thr His Glu Phe Ser Ser Tyr Ile Asp Thr Gly
915 920 925

Asp Leu Asn Xaa Ser Val Asp Gln Gly Ile Trp Val Xaa Xaa Lys Val
930 935 940

Arg Thr Thr Asp Gly Tyr Ala Thr Leu Gly Asn Leu Glu Leu Val Glu
945 950 955 960

Val Gly Pro Leu Ser Gly Glu Ser Leu Glu Arg Glu Gln Arg Asp Asn
965 970 975

Ala Lys Trp Asn Ala Glu Leu Gly Arg Lys Arg Ala Glu Thr Asp Arg
980 985 990

Val Tyr Gln Asp Ala Lys Gln Xaa Ile Asn His Leu Phe Val Asp Tyr
995 1000 1005

Gln Asp Gln Gln Leu Asn Pro Glu Ile Gly Met Ala Asp Ile Met Asp
1010 1015 1020

Ala Gln Asn Leu Val Ala Ser Ile Ser Asp Val Tyr Ser Asp Ala Val
1025 1030 1035 1040

Leu Gln Ile Pro Gly Ile Asn Tyr Glu Ile Tyr Thr Glu Leu Ser Asn
1045 1050 1055

Arg Leu Gln Gln Ala Ser Tyr Leu Tyr Thr Ser Arg Asn Ala Val Gln
1060 1065 1070

Asn Gly Asp Phe Asn Xaa Gly Leu Asp Ser Trp Asn Ala Thr Ala Xaa
1075 1080 1085

Ala Ser Val Gln Gln Asp Gly Asn Xaa His Phe Leu Val Leu Ser His
1090 1095 1100

Trp Asp Ala Gln Val Ser Gln Gln Phe Arg Val Gln Pro Asn Cys Lys
1105 1110 1115 1120

Tyr Val Leu Arg Val Thr Ala Glu Lys Val Gly Gly Gly Asp Gly Tyr
1125 1130 1135

Val Thr Ile Arg Asp Gly Ala His His Thr Glu Thr Leu Thr Phe Asn
1140 1145 1150

Ala Cys Asp Tyr Asp Xaa Asn Gly Thr Tyr Val Xaa Asp Asn Xaa Tyr
1155 1160 1165

Xaa Thr Lys Glu Val Val Phe Tyr Pro Glu Thr Glu His Met Trp Val
1170 1175 1180

Glu Val Xaa Glu Thr Glu Gly Ala Phe Xaa Ile Asp Ser Ile Glu Phe
1185 1190 1195 1200

Ile Glu Thr Gln Glu
1205

<210> SEQ ID NO 23
<211> LENGTH: 610
<212> TYPE: PRT
<213> ORGANISM: Bacillus thuringiensis

<400> SEQUENCE: 23

Asp Val Leu Gln Thr Gly Ile Asn Ile Val Gly Arg Leu Leu Gly Phe
1 5 10 15

-continued

```
Leu Gly Val Pro Phe Ala Gly Gln Leu Val Thr Phe Tyr Thr Phe Leu
            20                  25                  30

Leu Asn Gln Leu Trp Pro Thr Asn Asp Asn Ala Val Trp Glu Ala Phe
        35                  40                  45

Met Ala Gln Ile Glu Glu Leu Ile Asn Gln Arg Ile Ser Glu Ala Val
    50                  55                  60

Val Gly Thr Ala Ala Asp His Leu Thr Gly Leu His Asp Asn Tyr Glu
65                  70                  75                  80

Leu Tyr Val Glu Ala Leu Glu Glu Trp Leu Glu Arg Pro Asn Ala Ala
                85                  90                  95

Arg Thr Asn Leu Leu Phe Asn Arg Phe Thr Thr Leu Asp Ser Leu Phe
            100                 105                 110

Thr Gln Phe Met Pro Ser Phe Gly Thr Gly Pro Gly Ser Gln Asn Tyr
        115                 120                 125

Ala Val Pro Leu Leu Thr Val Tyr Ala Gln Ala Ala Asn Leu His Leu
    130                 135                 140

Leu Leu Leu Lys Asp Ala Glu Ile Tyr Gly Ala Arg Trp Gly Leu Asn
145                 150                 155                 160

Gln Asn Gln Ile Asn Ser Phe His Thr Arg Gln Gln Glu Arg Thr Gln
                165                 170                 175

Tyr Tyr Thr Asn His Cys Val Thr Thr Tyr Asn Thr Gly Leu Asp Arg
            180                 185                 190

Leu Arg Gly Thr Asn Thr Glu Ser Trp Leu Asn Tyr His Arg Phe Arg
        195                 200                 205

Arg Glu Met Thr Leu Met Ala Met Asp Leu Val Ala Leu Phe Pro Tyr
    210                 215                 220

Tyr Asn Val Arg Gln Tyr Pro Asn Gly Ala Asn Pro Gln Leu Thr Arg
225                 230                 235                 240

Glu Ile Tyr Thr Asp Pro Ile Val Tyr Asn Pro Pro Ala Asn Gln Gly
                245                 250                 255

Ile Cys Arg Arg Trp Gly Asn Asn Pro Tyr Asn Thr Phe Ser Glu Leu
            260                 265                 270

Glu Asn Ala Phe Ile Arg Pro Pro His Leu Phe Asp Arg Leu Asn Arg
        275                 280                 285

Leu Thr Ile Ser Arg Asn Arg Tyr Thr Ala Pro Thr Thr Asn Ser Tyr
    290                 295                 300

Leu Asp Tyr Trp Ser Gly His Thr Leu Gln Ser Gln Tyr Ala Asn Asn
305                 310                 315                 320

Pro Thr Thr Tyr Glu Thr Ser Tyr Gly Gln Ile Thr Ser Asn Thr Arg
                325                 330                 335

Leu Phe Asn Thr Thr Asn Gly Ala Asn Ala Ile Asp Ser Arg Ala Arg
            340                 345                 350

Asn Phe Gly Asn Leu Tyr Ala Asn Leu Tyr Gly Val Ser Tyr Leu Asn
        355                 360                 365

Ile Phe Pro Thr Gly Val Met Ser Glu Ile Thr Ser Ala Pro Asn Thr
    370                 375                 380

Cys Trp Gln Asp Leu Thr Thr Thr Glu Glu Leu Pro Leu Val Asn Asn
385                 390                 395                 400

Asn Phe Asn Leu Leu Ser His Val Thr Phe Leu Arg Phe Asn Thr Thr
                405                 410                 415

Gln Gly Gly Pro Leu Ala Thr Val Gly Phe Val Pro Thr Tyr Val Trp
            420                 425                 430

Thr Arg Gln Asp Val Asp Phe Asn Asn Ile Ile Thr Pro Asn Arg Ile
```

-continued

```
        435                 440                 445

Thr Gln Ile Pro Val Val Lys Ala Tyr Glu Leu Ser Ser Gly Ala Thr
    450                 455                 460

Val Val Lys Gly Pro Gly Phe Thr Gly Gly Asp Val Ile Arg Arg Thr
465                 470                 475                 480

Asn Thr Gly Gly Phe Gly Ala Ile Arg Val Ser Val Thr Gly Pro Leu
                485                 490                 495

Thr Gln Arg Tyr Arg Ile Arg Phe Arg Tyr Ala Ser Thr Ile Asp Phe
            500                 505                 510

Asp Phe Phe Val Thr Arg Gly Gly Thr Thr Ile Asn Asn Phe Arg Phe
        515                 520                 525

Thr Arg Thr Met Asn Arg Gly Gln Glu Ser Arg Tyr Glu Ser Tyr Arg
    530                 535                 540

Thr Val Glu Phe Thr Thr Pro Phe Asn Phe Thr Gln Ser Gln Asp Ile
545                 550                 555                 560

Ile Arg Thr Ser Ile Gln Gly Leu Ser Gly Asn Gly Glu Val Tyr Leu
                565                 570                 575

Asp Arg Ile Glu Ile Ile Pro Val Asn Pro Thr Arg Glu Ala Glu Glu
            580                 585                 590

Asp Leu Glu Ala Ala Lys Lys Ala Val Ala Ser Leu Phe Thr Arg Thr
        595                 600                 605

Arg Asp
    610


<210> SEQ ID NO 24
<211> LENGTH: 3510
<212> TYPE: DNA
<213> ORGANISM: Bacillus thuringiensis
<220> FEATURE:
<221> NAME/KEY: CDS
<222> LOCATION: (1)...(3510)

<400> SEQUENCE: 24

atg aat cga aat cat caa aat gaa tat gaa att att gat gcc cct cat       48
Met Asn Arg Asn His Gln Asn Glu Tyr Glu Ile Ile Asp Ala Pro His
 1               5                  10                  15

tgt gga tgt ccg tca gat gat gtt gtg aaa tat cct ttg aca gat gat       96
Cys Gly Cys Pro Ser Asp Asp Val Val Lys Tyr Pro Leu Thr Asp Asp
            20                  25                  30

ccg aat gct gga ttg caa aat atg aac tat aag gaa tat tta caa atg      144
Pro Asn Ala Gly Leu Gln Asn Met Asn Tyr Lys Glu Tyr Leu Gln Met
        35                  40                  45

tat ggt ggg gac tat aca gac cct ctt att aat cct aac tta tct gtt      192
Tyr Gly Gly Asp Tyr Thr Asp Pro Leu Ile Asn Pro Asn Leu Ser Val
     50                  55                  60

agt gga aaa gat gta ata caa gtt gga att aat att gta ggg aga tta      240
Ser Gly Lys Asp Val Ile Gln Val Gly Ile Asn Ile Val Gly Arg Leu
 65                  70                  75                  80

cta agc ttt ttt gga ttc ccc ttt tct agt caa tgg gtt aca gta tat      288
Leu Ser Phe Phe Gly Phe Pro Phe Ser Ser Gln Trp Val Thr Val Tyr
                85                  90                  95

acc tat ctt tta aac agc ttg tgg ccg gat gac gag aat tct gtt tgg      336
Thr Tyr Leu Leu Asn Ser Leu Trp Pro Asp Asp Glu Asn Ser Val Trp
            100                 105                 110

gat gct ttt atg aag aga ata gaa gaa ctt att gat caa aaa atc tca      384
Asp Ala Phe Met Lys Arg Ile Glu Glu Leu Ile Asp Gln Lys Ile Ser
        115                 120                 125

gaa gca gta aag ggt aga gca ttg gat gag cta act gga tta caa gat      432
```

-continued

```
Glu Ala Val Lys Gly Arg Ala Leu Asp Glu Leu Thr Gly Leu Gln Asp
    130                 135                 140

aat tat aat tta tat gta gaa gca tta gat gag tgg ctg aat aga cca      480
Asn Tyr Asn Leu Tyr Val Glu Ala Leu Asp Glu Trp Leu Asn Arg Pro
145                 150                 155                 160

aat ggc gca agg gca tcc tta gtt tct cag cga ttt aac att tta gat      528
Asn Gly Ala Arg Ala Ser Leu Val Ser Gln Arg Phe Asn Ile Leu Asp
                165                 170                 175

agc tta ttt aca caa ttt atg cca agc ttt ggc tct ggt cct gga agt      576
Ser Leu Phe Thr Gln Phe Met Pro Ser Phe Gly Ser Gly Pro Gly Ser
            180                 185                 190

caa aat tat tca act ata tta ctt cca gta tat gca caa gca gca aac      624
Gln Asn Tyr Ser Thr Ile Leu Leu Pro Val Tyr Ala Gln Ala Ala Asn
        195                 200                 205

ctt cat ttg tta tta tta aaa gat gca gac att tat gga gct aga tgg      672
Leu His Leu Leu Leu Leu Lys Asp Ala Asp Ile Tyr Gly Ala Arg Trp
    210                 215                 220

ggg ctg aat caa act caa att gat caa ttc cat tct cgt caa caa agc      720
Gly Leu Asn Gln Thr Gln Ile Asp Gln Phe His Ser Arg Gln Gln Ser
225                 230                 235                 240

ctt act cgg act tat aca aat cat tgt gtt act acg tat aat gat gga      768
Leu Thr Arg Thr Tyr Thr Asn His Cys Val Thr Thr Tyr Asn Asp Gly
                245                 250                 255

tta gcg gaa tta aga ggc aca agc gtt gag agt tgg ctc aaa tat cat      816
Leu Ala Glu Leu Arg Gly Thr Ser Val Glu Ser Trp Leu Lys Tyr His
            260                 265                 270

caa tat cgt agg gaa atg aca gta acg gct atg gat tta gtg gca tta      864
Gln Tyr Arg Arg Glu Met Thr Val Thr Ala Met Asp Leu Val Ala Leu
        275                 280                 285

ttc cca tac tat aat gtt cga caa tat cca aat gga gca aat cca caa      912
Phe Pro Tyr Tyr Asn Val Arg Gln Tyr Pro Asn Gly Ala Asn Pro Gln
    290                 295                 300

ctt aca cgt gag gta tat aca gat cca atc gta ttt aat cca ccg gag      960
Leu Thr Arg Glu Val Tyr Thr Asp Pro Ile Val Phe Asn Pro Pro Glu
305                 310                 315                 320

cct cca agt ggc gct ttc tgc gaa agt ttt tat aat atc cga gcg gct     1008
Pro Pro Ser Gly Ala Phe Cys Glu Ser Phe Tyr Asn Ile Arg Ala Ala
                325                 330                 335

cga gaa cgc tta act ttt tcg caa ctt gaa aat gca ata att cgt cca     1056
Arg Glu Arg Leu Thr Phe Ser Gln Leu Glu Asn Ala Ile Ile Arg Pro
            340                 345                 350

ccg cgc ttg ttt gaa agg ttt caa gct tta ggg att tat aca ggc gag     1104
Pro Arg Leu Phe Glu Arg Phe Gln Ala Leu Gly Ile Tyr Thr Gly Glu
        355                 360                 365

gcg cgg ctg aat caa aat agt gct cca acg aac tat tgg att gga cat     1152
Ala Arg Leu Asn Gln Asn Ser Ala Pro Thr Asn Tyr Trp Ile Gly His
    370                 375                 380

ttt ata aga aat aca cgt tta ggg gac tca aca aca att act aca aat     1200
Phe Ile Arg Asn Thr Arg Leu Gly Asp Ser Thr Thr Ile Thr Thr Asn
385                 390                 395                 400

tat gga aca acc aat aat cgt tta act aat ttt att cct cct act acc     1248
Tyr Gly Thr Thr Asn Asn Arg Leu Thr Asn Phe Ile Pro Pro Thr Thr
                405                 410                 415

agt gat gtt tat caa att aat tca atc tca agt aat tta gcc tct gct     1296
Ser Asp Val Tyr Gln Ile Asn Ser Ile Ser Ser Asn Leu Ala Ser Ala
            420                 425                 430

tta agc act tta ttt ggg gtt act aga gca caa ttc cat tat gga tca     1344
Leu Ser Thr Leu Phe Gly Val Thr Arg Ala Gln Phe His Tyr Gly Ser
        435                 440                 445
```

-continued

```
gga att att tgg tcg tat gtc gga caa aat aac gtt ctt cca caa tgt     1392
Gly Ile Ile Trp Ser Tyr Val Gly Gln Asn Asn Val Leu Pro Gln Cys
    450                 455                 460

cat caa aac tat aat tca ata gaa gaa tta cca aac caa agc gat gaa     1440
His Gln Asn Tyr Asn Ser Ile Glu Glu Leu Pro Asn Gln Ser Asp Glu
465                 470                 475                 480

cct aca gtt aga agt tat agc cat aga tta tct cat atc acc tct ttt     1488
Pro Thr Val Arg Ser Tyr Ser His Arg Leu Ser His Ile Thr Ser Phe
                485                 490                 495

aat ttc agt gta cag ctt aat aat cct gta att tct ctt ggc aat atg     1536
Asn Phe Ser Val Gln Leu Asn Asn Pro Val Ile Ser Leu Gly Asn Met
            500                 505                 510

cct gta tat gtg tgg aca cat cgc agt gtg gac ctt aat aac aca att     1584
Pro Val Tyr Val Trp Thr His Arg Ser Val Asp Leu Asn Asn Thr Ile
        515                 520                 525

act tca gat aga att act caa tta cca gcg gta aag gca tcg aca cta     1632
Thr Ser Asp Arg Ile Thr Gln Leu Pro Ala Val Lys Ala Ser Thr Leu
    530                 535                 540

ggt gcg gga gct att gtc gtg aaa ggt cca gga ttt aca gga gga gat     1680
Gly Ala Gly Ala Ile Val Val Lys Gly Pro Gly Phe Thr Gly Gly Asp
545                 550                 555                 560

gta atc cga aga aca tct gtt ggt gat ttc gga aca ata aga gtg tcg     1728
Val Ile Arg Arg Thr Ser Val Gly Asp Phe Gly Thr Ile Arg Val Ser
                565                 570                 575

gtt act ggc tcg cta act cag caa tat cgc ata agg ttc cgt tat gct     1776
Val Thr Gly Ser Leu Thr Gln Gln Tyr Arg Ile Arg Phe Arg Tyr Ala
            580                 585                 590

tcg aca ata gat ttt gat ttc ttt gta ata cgt gga gga act act ata     1824
Ser Thr Ile Asp Phe Asp Phe Phe Val Ile Arg Gly Gly Thr Thr Ile
        595                 600                 605

aat aat ttt aga ttc aca cat aca atg agc agt gga gag gaa tca aga     1872
Asn Asn Phe Arg Phe Thr His Thr Met Ser Ser Gly Glu Glu Ser Arg
    610                 615                 620

tat gaa tcc tat cgt act gta gag ttt tcc act cct ttt aac ttt aca     1920
Tyr Glu Ser Tyr Arg Thr Val Glu Phe Ser Thr Pro Phe Asn Phe Thr
625                 630                 635                 640

caa agt caa gat ata att cga aca tct atc cag gga ctt agt gga aat     1968
Gln Ser Gln Asp Ile Ile Arg Thr Ser Ile Gln Gly Leu Ser Gly Asn
                645                 650                 655

ggg gaa gta tat ctt gat aga att gaa atc att cct gtg aat ccg aca     2016
Gly Glu Val Tyr Leu Asp Arg Ile Glu Ile Ile Pro Val Asn Pro Thr
            660                 665                 670

cga gaa gca gaa gag gat cta gaa gat gca aag aaa gcg gtg gca ggc     2064
Arg Glu Ala Glu Glu Asp Leu Glu Asp Ala Lys Lys Ala Val Ala Gly
        675                 680                 685

ttg ttt aca cgt aca aga gat gga tta cag gta aat gtg aca gat tac     2112
Leu Phe Thr Arg Thr Arg Asp Gly Leu Gln Val Asn Val Thr Asp Tyr
    690                 695                 700

caa gtg gat cga gcg gca aat tta gtg tca tgc tta tca gat gaa caa     2160
Gln Val Asp Arg Ala Ala Asn Leu Val Ser Cys Leu Ser Asp Glu Gln
705                 710                 715                 720

tat tcg cat gat aaa aaa atg cta atg gaa gct gta cgc gcg gca aaa     2208
Tyr Ser His Asp Lys Lys Met Leu Met Glu Ala Val Arg Ala Ala Lys
                725                 730                 735

cgt ctc agc cga gaa cgc aat tta ctt cag gat ccg gat ttc aat gaa     2256
Arg Leu Ser Arg Glu Arg Asn Leu Leu Gln Asp Pro Asp Phe Asn Glu
            740                 745                 750

ata aat agt acg gaa gag aat ggt tgg aaa gca agt aac ggt att atc     2304
Ile Asn Ser Thr Glu Glu Asn Gly Trp Lys Ala Ser Asn Gly Ile Ile
        755                 760                 765
```

-continued

```
att agc gag ggc ggt cca ttc ttt aaa ggc cgt gtc ctt cag tta gca     2352
Ile Ser Glu Gly Gly Pro Phe Phe Lys Gly Arg Val Leu Gln Leu Ala
    770                 775                 780

agc gca aga gaa aat tat cca aca tac att tat caa aag gta gat gca     2400
Ser Ala Arg Glu Asn Tyr Pro Thr Tyr Ile Tyr Gln Lys Val Asp Ala
785                 790                 795                 800

tcg gtg tta aag cct tat aca cgc tat aga ctg gat gga ttt gtg aag     2448
Ser Val Leu Lys Pro Tyr Thr Arg Tyr Arg Leu Asp Gly Phe Val Lys
                805                 810                 815

agt agt gaa gat tta gaa att gat ctc gtt cat caa cat aaa gtc cat     2496
Ser Ser Glu Asp Leu Glu Ile Asp Leu Val His Gln His Lys Val His
            820                 825                 830

ctt gta aaa aat gta ccg gat aat tta gta tca gat act tac cca gat     2544
Leu Val Lys Asn Val Pro Asp Asn Leu Val Ser Asp Thr Tyr Pro Asp
        835                 840                 845

ggt tct tgc aga gga gtt aac cgt tgt gat gaa cag cat cag gta gat     2592
Gly Ser Cys Arg Gly Val Asn Arg Cys Asp Glu Gln His Gln Val Asp
    850                 855                 860

gta cag ata gat aca gaa cat cat cca atg gat tgc tgt gaa gcg gct     2640
Val Gln Ile Asp Thr Glu His His Pro Met Asp Cys Cys Glu Ala Ala
865                 870                 875                 880

caa acc cat gag ttt tct tcc tat att aat aca gga gat cta aat tca     2688
Gln Thr His Glu Phe Ser Ser Tyr Ile Asn Thr Gly Asp Leu Asn Ser
                885                 890                 895

agt gta gat cag ggt atc tgg gtt gta ttg aaa gtt cga aca gca gat     2736
Ser Val Asp Gln Gly Ile Trp Val Val Leu Lys Val Arg Thr Ala Asp
            900                 905                 910

ggt tat gcg acg cta gga aat ctt gaa ttg gta gag gtt ggt cca tta     2784
Gly Tyr Ala Thr Leu Gly Asn Leu Glu Leu Val Glu Val Gly Pro Leu
        915                 920                 925

tcg ggt gaa tct cta gaa cgc gaa caa aga gat aat gcg aaa tgg aat     2832
Ser Gly Glu Ser Leu Glu Arg Glu Gln Arg Asp Asn Ala Lys Trp Asn
    930                 935                 940

gca gag cta gga aga gag cgt gca gaa aca gat cgc gtg tat cta gct     2880
Ala Glu Leu Gly Arg Glu Arg Ala Glu Thr Asp Arg Val Tyr Leu Ala
945                 950                 955                 960

gcg aaa caa gca att aat cat cta ttt gta gac tat caa gat caa caa     2928
Ala Lys Gln Ala Ile Asn His Leu Phe Val Asp Tyr Gln Asp Gln Gln
                965                 970                 975

tta aat ccg gaa ata ggg cta gca gag att aat gaa gcc tca aat ctt     2976
Leu Asn Pro Glu Ile Gly Leu Ala Glu Ile Asn Glu Ala Ser Asn Leu
            980                 985                 990

gtg gag tca att aca ggt gtg tat agt gat aca gta ttg cag att cct     3024
Val Glu Ser Ile Thr Gly Val Tyr Ser Asp Thr Val Leu Gln Ile Pro
        995                 1000                1005

ggg att agc tac gaa att tac aca gag tta tcc gat cga tta caa caa     3072
Gly Ile Ser Tyr Glu Ile Tyr Thr Glu Leu Ser Asp Arg Leu Gln Gln
    1010                1015                1020

gca tcg tat ctg tat acg tct cgc aat gcc gtg caa aac ggt gat ttt     3120
Ala Ser Tyr Leu Tyr Thr Ser Arg Asn Ala Val Gln Asn Gly Asp Phe
1025                1030                1035                1040

gac agc ggg tta gat agt tgg aat gca act acg gat gca tcg gtt cag     3168
Asp Ser Gly Leu Asp Ser Trp Asn Ala Thr Thr Asp Ala Ser Val Gln
                1045                1050                1055

caa gat ggc aat atg cat ttc tta gtt ctt tct cat tgg gat gca caa     3216
Gln Asp Gly Asn Met His Phe Leu Val Leu Ser His Trp Asp Ala Gln
            1060                1065                1070

gtt act caa caa tta aga gta aac ccg aat tgt aaa tat gtc tta cgt     3264
Val Thr Gln Gln Leu Arg Val Asn Pro Asn Cys Lys Tyr Val Leu Arg
```

-continued

```
        1075                1080                1085

gtg aca gca aga aaa gta gga ggc gga gat ggg tac gtc aca atc cga     3312
Val Thr Ala Arg Lys Val Gly Gly Gly Asp Gly Tyr Val Thr Ile Arg
    1090                1095                1100

gat ggg gct cat cac cga gaa act ctt aca ttt aat gca tgt gac tac     3360
Asp Gly Ala His His Arg Glu Thr Leu Thr Phe Asn Ala Cys Asp Tyr
1105                1110                1115                1120

gat gta aat ggt acg tat gta aat gac aat acg tat att aca aaa gaa     3408
Asp Val Asn Gly Thr Tyr Val Asn Asp Asn Thr Tyr Ile Thr Lys Glu
                1125                1130                1135

gtg gta ttc tat cct cat aca gaa cat acg tgg gta gag gtg agt gaa     3456
Val Val Phe Tyr Pro His Thr Glu His Thr Trp Val Glu Val Ser Glu
            1140                1145                1150

tcc gaa ggt gca ttc tat ata gac agt att gag ttg att gaa aca caa     3504
Ser Glu Gly Ala Phe Tyr Ile Asp Ser Ile Glu Leu Ile Glu Thr Gln
        1155                1160                1165

gaa tag                                                             3510
Glu  *


<210> SEQ ID NO 25
<211> LENGTH: 1169
<212> TYPE: PRT
<213> ORGANISM: Bacillus thuringiensis

<400> SEQUENCE: 25

Met Asn Arg Asn His Gln Asn Glu Tyr Glu Ile Ile Asp Ala Pro His
 1               5                  10                  15

Cys Gly Cys Pro Ser Asp Asp Val Val Lys Tyr Pro Leu Thr Asp Asp
            20                  25                  30

Pro Asn Ala Gly Leu Gln Asn Met Asn Tyr Lys Glu Tyr Leu Gln Met
        35                  40                  45

Tyr Gly Gly Asp Tyr Thr Asp Pro Leu Ile Asn Pro Asn Leu Ser Val
    50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Thr Val Tyr
                85                  90                  95

Thr Tyr Leu Leu Asn Ser Leu Trp Pro Asp Asp Glu Asn Ser Val Trp
            100                 105                 110

Asp Ala Phe Met Lys Arg Ile Glu Glu Leu Ile Asp Gln Lys Ile Ser
        115                 120                 125

Glu Ala Val Lys Gly Arg Ala Leu Asp Glu Leu Thr Gly Leu Gln Asp
    130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
            180                 185                 190

Gln Asn Tyr Ser Thr Ile Leu Leu Pro Val Tyr Ala Gln Ala Ala Asn
        195                 200                 205

Leu His Leu Leu Leu Leu Lys Asp Ala Asp Ile Tyr Gly Ala Arg Trp
    210                 215                 220

Gly Leu Asn Gln Thr Gln Ile Asp Gln Phe His Ser Arg Gln Gln Ser
225                 230                 235                 240

Leu Thr Arg Thr Tyr Thr Asn His Cys Val Thr Thr Tyr Asn Asp Gly
```

-continued

```
                245                 250                 255

Leu Ala Glu Leu Arg Gly Thr Ser Val Glu Ser Trp Leu Lys Tyr His
            260                 265                 270

Gln Tyr Arg Arg Glu Met Thr Val Thr Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Val Tyr Thr Asp Pro Ile Val Phe Asn Pro Pro Glu
305                 310                 315                 320

Pro Pro Ser Gly Ala Phe Cys Glu Ser Phe Tyr Asn Ile Arg Ala Ala
                325                 330                 335

Arg Glu Arg Leu Thr Phe Ser Gln Leu Glu Asn Ala Ile Ile Arg Pro
            340                 345                 350

Pro Arg Leu Phe Glu Arg Phe Gln Ala Leu Gly Ile Tyr Thr Gly Glu
        355                 360                 365

Ala Arg Leu Asn Gln Asn Ser Ala Pro Thr Asn Tyr Trp Ile Gly His
    370                 375                 380

Phe Ile Arg Asn Thr Arg Leu Gly Asp Ser Thr Thr Ile Thr Thr Asn
385                 390                 395                 400

Tyr Gly Thr Thr Asn Asn Arg Leu Thr Asn Phe Ile Pro Pro Thr Thr
                405                 410                 415

Ser Asp Val Tyr Gln Ile Asn Ser Ile Ser Ser Asn Leu Ala Ser Ala
            420                 425                 430

Leu Ser Thr Leu Phe Gly Val Thr Arg Ala Gln Phe His Tyr Gly Ser
        435                 440                 445

Gly Ile Ile Trp Ser Tyr Val Gly Gln Asn Asn Val Leu Pro Gln Cys
    450                 455                 460

His Gln Asn Tyr Asn Ser Ile Glu Glu Leu Pro Asn Gln Ser Asp Glu
465                 470                 475                 480

Pro Thr Val Arg Ser Tyr Ser His Arg Leu Ser His Ile Thr Ser Phe
                485                 490                 495

Asn Phe Ser Val Gln Leu Asn Asn Pro Val Ile Ser Leu Gly Asn Met
            500                 505                 510

Pro Val Tyr Val Trp Thr His Arg Ser Val Asp Leu Asn Asn Thr Ile
        515                 520                 525

Thr Ser Asp Arg Ile Thr Gln Leu Pro Ala Val Lys Ala Ser Thr Leu
    530                 535                 540

Gly Ala Gly Ala Ile Val Val Lys Gly Pro Gly Phe Thr Gly Gly Asp
545                 550                 555                 560

Val Ile Arg Arg Thr Ser Val Gly Asp Phe Gly Thr Ile Arg Val Ser
                565                 570                 575

Val Thr Gly Ser Leu Thr Gln Gln Tyr Arg Ile Arg Phe Arg Tyr Ala
            580                 585                 590

Ser Thr Ile Asp Phe Asp Phe Phe Val Ile Arg Gly Gly Thr Thr Ile
        595                 600                 605

Asn Asn Phe Arg Phe Thr His Thr Met Ser Ser Gly Glu Glu Ser Arg
    610                 615                 620

Tyr Glu Ser Tyr Arg Thr Val Glu Phe Ser Thr Pro Phe Asn Phe Thr
625                 630                 635                 640

Gln Ser Gln Asp Ile Ile Arg Thr Ser Ile Gln Gly Leu Ser Gly Asn
                645                 650                 655

Gly Glu Val Tyr Leu Asp Arg Ile Glu Ile Ile Pro Val Asn Pro Thr
            660                 665                 670
```

-continued

```
Arg Glu Ala Glu Glu Asp Leu Glu Asp Ala Lys Lys Ala Val Ala Gly
        675                 680                 685

Leu Phe Thr Arg Thr Arg Asp Gly Leu Gln Val Asn Val Thr Asp Tyr
    690                 695                 700

Gln Val Asp Arg Ala Ala Asn Leu Val Ser Cys Leu Ser Asp Glu Gln
705                 710                 715                 720

Tyr Ser His Asp Lys Lys Met Leu Met Glu Ala Val Arg Ala Ala Lys
                725                 730                 735

Arg Leu Ser Arg Glu Arg Asn Leu Leu Gln Asp Pro Asp Phe Asn Glu
            740                 745                 750

Ile Asn Ser Thr Glu Glu Asn Gly Trp Lys Ala Ser Asn Gly Ile Ile
        755                 760                 765

Ile Ser Glu Gly Gly Pro Phe Phe Lys Gly Arg Val Leu Gln Leu Ala
    770                 775                 780

Ser Ala Arg Glu Asn Tyr Pro Thr Tyr Ile Tyr Gln Lys Val Asp Ala
785                 790                 795                 800

Ser Val Leu Lys Pro Tyr Thr Arg Tyr Arg Leu Asp Gly Phe Val Lys
                805                 810                 815

Ser Ser Glu Asp Leu Glu Ile Asp Leu Val His Gln His Lys Val His
            820                 825                 830

Leu Val Lys Asn Val Pro Asp Asn Leu Val Ser Asp Thr Tyr Pro Asp
        835                 840                 845

Gly Ser Cys Arg Gly Val Asn Arg Cys Asp Glu Gln His Gln Val Asp
    850                 855                 860

Val Gln Ile Asp Thr Glu His His Pro Met Asp Cys Cys Glu Ala Ala
865                 870                 875                 880

Gln Thr His Glu Phe Ser Ser Tyr Ile Asn Thr Gly Asp Leu Asn Ser
                885                 890                 895

Ser Val Asp Gln Gly Ile Trp Val Val Leu Lys Val Arg Thr Ala Asp
            900                 905                 910

Gly Tyr Ala Thr Leu Gly Asn Leu Glu Leu Val Glu Val Gly Pro Leu
        915                 920                 925

Ser Gly Glu Ser Leu Glu Arg Glu Gln Arg Asp Asn Ala Lys Trp Asn
    930                 935                 940

Ala Glu Leu Gly Arg Glu Arg Ala Glu Thr Asp Arg Val Tyr Leu Ala
945                 950                 955                 960

Ala Lys Gln Ala Ile Asn His Leu Phe Val Asp Tyr Gln Asp Gln Gln
                965                 970                 975

Leu Asn Pro Glu Ile Gly Leu Ala Glu Ile Asn Glu Ala Ser Asn Leu
            980                 985                 990

Val Glu Ser Ile Thr Gly Val Tyr Ser Asp Thr Val Leu Gln Ile Pro
        995                 1000                1005

Gly Ile Ser Tyr Glu Ile Tyr Thr Glu Leu Ser Asp Arg Leu Gln Gln
    1010                1015                1020

Ala Ser Tyr Leu Tyr Thr Ser Arg Asn Ala Val Gln Asn Gly Asp Phe
1025                1030                1035                1040

Asp Ser Gly Leu Asp Ser Trp Asn Ala Thr Thr Asp Ala Ser Val Gln
                1045                1050                1055

Gln Asp Gly Asn Met His Phe Leu Val Leu Ser His Trp Asp Ala Gln
            1060                1065                1070

Val Thr Gln Gln Leu Arg Val Asn Pro Asn Cys Lys Tyr Val Leu Arg
        1075                1080                1085
```

-continued

```
Val Thr Ala Arg Lys Val Gly Gly Gly Asp Gly Tyr Val Thr Ile Arg
    1090                1095                1100

Asp Gly Ala His His Arg Glu Thr Leu Thr Phe Asn Ala Cys Asp Tyr
1105                1110                1115                1120

Asp Val Asn Gly Thr Tyr Val Asn Asp Asn Thr Tyr Ile Thr Lys Glu
                1125                1130                1135

Val Val Phe Tyr Pro His Thr Glu His Thr Trp Val Glu Val Ser Glu
            1140                1145                1150

Ser Glu Gly Ala Phe Tyr Ile Asp Ser Ile Glu Leu Ile Glu Thr Gln
        1155                1160                1165

Glu


<210> SEQ ID NO 26
<211> LENGTH: 3465
<212> TYPE: DNA
<213> ORGANISM: Bacillus thuringiensis
<220> FEATURE:
<221> NAME/KEY: CDS
<222> LOCATION: (1)...(3465)

<400> SEQUENCE: 26

atg aat cga aat aat caa aat gaa tat gaa att att gac gga acc aat       48
Met Asn Arg Asn Asn Gln Asn Glu Tyr Glu Ile Ile Asp Gly Thr Asn
 1               5                  10                  15

tgt gat tgt tcg tca gat gag gtt gtg aaa tat cct tta gca agt gag       96
Cys Asp Cys Ser Ser Asp Glu Val Val Lys Tyr Pro Leu Ala Ser Glu
            20                  25                  30

caa aat ggt gtg tta caa aat atg aac tat aaa gaa tat tta caa acg      144
Gln Asn Gly Val Leu Gln Asn Met Asn Tyr Lys Glu Tyr Leu Gln Thr
        35                  40                  45

tat gat gga gac tat aca ggc tct ctt atc aat cct aac tta tct att      192
Tyr Asp Gly Asp Tyr Thr Gly Ser Leu Ile Asn Pro Asn Leu Ser Ile
    50                  55                  60

aat act aga gat gta cta caa act ggt att act att gta gga aga gta      240
Asn Thr Arg Asp Val Leu Gln Thr Gly Ile Thr Ile Val Gly Arg Val
 65                 70                  75                  80

cta ggg ttt tta ggt gtt cca ttt gct ggc caa tta gtt act ttc tat      288
Leu Gly Phe Leu Gly Val Pro Phe Ala Gly Gln Leu Val Thr Phe Tyr
                85                  90                  95

acg ttt ctc tta aat cag ttg tgg cca act aat aat aat gca gta tgg      336
Thr Phe Leu Leu Asn Gln Leu Trp Pro Thr Asn Asn Asn Ala Val Trp
            100                 105                 110

gaa gct ttt atg gca caa gta gaa gag ctt atc gac caa aga ata tcg      384
Glu Ala Phe Met Ala Gln Val Glu Glu Leu Ile Asp Gln Arg Ile Ser
        115                 120                 125

gat caa gta gta aga aat gca ctt gat gac cta act gga tta cac gat      432
Asp Gln Val Val Arg Asn Ala Leu Asp Asp Leu Thr Gly Leu His Asp
    130                 135                 140

tat tat aat gaa tat cta gcg gca tta gag gag tgg cta gat aga ccg      480
Tyr Tyr Asn Glu Tyr Leu Ala Ala Leu Glu Glu Trp Leu Asp Arg Pro
145                 150                 155                 160

aat ggc gcc aga gct aac tta gct ttt caa agg ttt gaa aac ctg cat      528
Asn Gly Ala Arg Ala Asn Leu Ala Phe Gln Arg Phe Glu Asn Leu His
                165                 170                 175

acc gca ttt gta act aga atg cca agt ttt gga act ggt cct ggt agt      576
Thr Ala Phe Val Thr Arg Met Pro Ser Phe Gly Thr Gly Pro Gly Ser
            180                 185                 190

caa aga gat gcg gta gca ttg ctg acg gta tat gca caa gca gcg aat      624
Gln Arg Asp Ala Val Ala Leu Leu Thr Val Tyr Ala Gln Ala Ala Asn
        195                 200                 205
```

-continued

```
ctc cat ttg tta tta tta aaa gat gca gaa att tat ggg gca aga tgg      672
Leu His Leu Leu Leu Leu Lys Asp Ala Glu Ile Tyr Gly Ala Arg Trp
    210                 215                 220

gga ctt caa caa agt cag att aac tta tat ttt aat gct caa caa gat      720
Gly Leu Gln Gln Ser Gln Ile Asn Leu Tyr Phe Asn Ala Gln Gln Asp
225                 230                 235                 240

cgt act cga att tat acc aat cat tgt gtg gca aca tat aat aga gga      768
Arg Thr Arg Ile Tyr Thr Asn His Cys Val Ala Thr Tyr Asn Arg Gly
                245                 250                 255

tta gaa gat tta aaa ggc aca aat acg gaa agt tgg tat aat tat cat      816
Leu Glu Asp Leu Lys Gly Thr Asn Thr Glu Ser Trp Tyr Asn Tyr His
            260                 265                 270

caa ttc cgt aga gag atg aca tta atg gca atg gat tta gta gcg tta      864
Gln Phe Arg Arg Glu Met Thr Leu Met Ala Met Asp Leu Val Ala Leu
        275                 280                 285

ttc cca tat tac aat gta cga caa tat cca aat ggg gca aat cct cag      912
Phe Pro Tyr Tyr Asn Val Arg Gln Tyr Pro Asn Gly Ala Asn Pro Gln
    290                 295                 300

ctt aca cgt gaa ata tat aca gat cca gtt gta ttt aat cca cca gcc      960
Leu Thr Arg Glu Ile Tyr Thr Asp Pro Val Val Phe Asn Pro Pro Ala
305                 310                 315                 320

aat cag gga ctt tgt aga cgt tgg gga aat aac cct tat atg aca ttt     1008
Asn Gln Gly Leu Cys Arg Arg Trp Gly Asn Asn Pro Tyr Met Thr Phe
                325                 330                 335

tcg gga ctt gag aat gct ttc att cgc cct ccg cat ctt ttt gat aga     1056
Ser Gly Leu Glu Asn Ala Phe Ile Arg Pro Pro His Leu Phe Asp Arg
            340                 345                 350

ttg aat agc tta aca att aac agc cat cga ttt ccc att tca tca aat     1104
Leu Asn Ser Leu Thr Ile Asn Ser His Arg Phe Pro Ile Ser Ser Asn
        355                 360                 365

ttt atg gat tat tgg gca gga cat acg tta cgc cgt agt tat atg aat     1152
Phe Met Asp Tyr Trp Ala Gly His Thr Leu Arg Arg Ser Tyr Met Asn
    370                 375                 380

aat tcg gca gta caa gaa gat agt tat ggc gcg atc act ccc aca aga     1200
Asn Ser Ala Val Gln Glu Asp Ser Tyr Gly Ala Ile Thr Pro Thr Arg
385                 390                 395                 400

gtc aca att aat ccc gga gtt aat gga aca aac cac ata gag tca acg     1248
Val Thr Ile Asn Pro Gly Val Asn Gly Thr Asn His Ile Glu Ser Thr
                405                 410                 415

gca gta gat ttt cgt tct ggt ctg gtg ggt ata tat ggc gtg cat aga     1296
Ala Val Asp Phe Arg Ser Gly Leu Val Gly Ile Tyr Gly Val His Arg
            420                 425                 430

gct tcg ttt gtc ccg ggc ggc tta ttt aat ggt acc att tct cct gct     1344
Ala Ser Phe Val Pro Gly Gly Leu Phe Asn Gly Thr Ile Ser Pro Ala
        435                 440                 445

aat gca ggg tgt aga aat ctg cat gat aca aga gac gta tta cca ttg     1392
Asn Ala Gly Cys Arg Asn Leu His Asp Thr Arg Asp Val Leu Pro Leu
    450                 455                 460

gaa gaa aat aac gga agc cct tcc cat aga tta tct cat gtt act ttt     1440
Glu Glu Asn Asn Gly Ser Pro Ser His Arg Leu Ser His Val Thr Phe
465                 470                 475                 480

tta agt ttt caa act aat cag gct ggg tct ctt gca aat ggt gga agc     1488
Leu Ser Phe Gln Thr Asn Gln Ala Gly Ser Leu Ala Asn Gly Gly Ser
                485                 490                 495

gta cct tta tat gtt tgg gca cgt caa gat ata gat ttt aat aac aca     1536
Val Pro Leu Tyr Val Trp Ala Arg Gln Asp Ile Asp Phe Asn Asn Thr
            500                 505                 510

att acc gca aat aga att aca caa cta cca ttg gta aag gca ttt gaa     1584
Ile Thr Ala Asn Arg Ile Thr Gln Leu Pro Leu Val Lys Ala Phe Glu
```

-continued

```
        515                 520                 525

ata gct gcg ggt act act atc gta aaa gga cca gga ttt aca gga ggg      1632
Ile Ala Ala Gly Thr Thr Ile Val Lys Gly Pro Gly Phe Thr Gly Gly
    530                 535                 540

gat ata ctt cga aga acg agc act ggt act tta gga aca ata aga gta      1680
Asp Ile Leu Arg Arg Thr Ser Thr Gly Thr Leu Gly Thr Ile Arg Val
545                 550                 555                 560

aat gtt aat tca ccg tta acg caa cga tat cgc gta aga ttc cgt tat      1728
Asn Val Asn Ser Pro Leu Thr Gln Arg Tyr Arg Val Arg Phe Arg Tyr
                565                 570                 575

gct tcg aca gta gat ttt gat ttc ttt gta tca cgt gga ggg act act      1776
Ala Ser Thr Val Asp Phe Asp Phe Phe Val Ser Arg Gly Gly Thr Thr
            580                 585                 590

gta aat aat ttt aga ttc cca cgt aca atg agc aga ggt cag gaa tca      1824
Val Asn Asn Phe Arg Phe Pro Arg Thr Met Ser Arg Gly Gln Glu Ser
        595                 600                 605

aga tac gaa tcc tat gtc aca agt gag ttt acg act cct ttt acc ttt      1872
Arg Tyr Glu Ser Tyr Val Thr Ser Glu Phe Thr Thr Pro Phe Thr Phe
    610                 615                 620

aca caa agt caa gat ttt att cga acg tct atc caa gga ctt agt ggg      1920
Thr Gln Ser Gln Asp Phe Ile Arg Thr Ser Ile Gln Gly Leu Ser Gly
625                 630                 635                 640

aat gga gaa gtg tat ctt gat aga att gaa atc atc cca gtt aac ccg      1968
Asn Gly Glu Val Tyr Leu Asp Arg Ile Glu Ile Ile Pro Val Asn Pro
                645                 650                 655

gca cga gaa gcg gag gag gat tta gaa gcg gcg aag aaa gcg gtg gcg      2016
Ala Arg Glu Ala Glu Glu Asp Leu Glu Ala Ala Lys Lys Ala Val Ala
            660                 665                 670

agc ttg ttt aca cgt act aga gac gga tta cag gta aat gtg aca gat      2064
Ser Leu Phe Thr Arg Thr Arg Asp Gly Leu Gln Val Asn Val Thr Asp
        675                 680                 685

tat caa gtc gat caa gcg gca aat tta gtg tcg tgc tta tca gat gaa      2112
Tyr Gln Val Asp Gln Ala Ala Asn Leu Val Ser Cys Leu Ser Asp Glu
    690                 695                 700

caa tat ggg cat gat aaa aag atg tta ttg gaa gcc gta cgc gca gca      2160
Gln Tyr Gly His Asp Lys Lys Met Leu Leu Glu Ala Val Arg Ala Ala
705                 710                 715                 720

aaa cgc ctc agc cga gaa cgc aac ttg ctt caa gat cca gat ttt aat      2208
Lys Arg Leu Ser Arg Glu Arg Asn Leu Leu Gln Asp Pro Asp Phe Asn
                725                 730                 735

gaa ata aat agt ata gaa gag aat ggc tgg aag gca agt aac ggt gtt      2256
Glu Ile Asn Ser Ile Glu Glu Asn Gly Trp Lys Ala Ser Asn Gly Val
            740                 745                 750

act att agc gag ggc ggg cca ttc ttt aaa ggt cgt gca ctt cag tta      2304
Thr Ile Ser Glu Gly Gly Pro Phe Phe Lys Gly Arg Ala Leu Gln Leu
        755                 760                 765

gca agc gca aga gaa aat tat cca aca tac att tat caa aaa gta gat      2352
Ala Ser Ala Arg Glu Asn Tyr Pro Thr Tyr Ile Tyr Gln Lys Val Asp
    770                 775                 780

gca tcg gtg tta aag ccg tat aca cgc tat aga cta gat gga ttt gtg      2400
Ala Ser Val Leu Lys Pro Tyr Thr Arg Tyr Arg Leu Asp Gly Phe Val
785                 790                 795                 800

aag agt agt caa gat tta gaa att gat ctc att cac cat cat aaa gtc      2448
Lys Ser Ser Gln Asp Leu Glu Ile Asp Leu Ile His His His Lys Val
                805                 810                 815

cat ctt gta aaa aat gta cca gat aat tta gta tct gat act tac tca      2496
His Leu Val Lys Asn Val Pro Asp Asn Leu Val Ser Asp Thr Tyr Ser
            820                 825                 830

gat ggt tct tgc agc gga atc aac cgt tgt gat gaa cag cat cag gta      2544
```

-continued

```
Asp Gly Ser Cys Ser Gly Ile Asn Arg Cys Asp Glu Gln His Gln Val
        835                 840                 845

gat atg cag cta gat gcg gag cat cat cca atg gat tgc tgt gaa gcg      2592
Asp Met Gln Leu Asp Ala Glu His His Pro Met Asp Cys Cys Glu Ala
    850                 855                 860

gct gaa aca cat gaa ttt tct tcc tat att gat aca ggt gat cta aac      2640
Ala Glu Thr His Glu Phe Ser Ser Tyr Ile Asp Thr Gly Asp Leu Asn
865                 870                 875                 880

cca agt gta gat caa ggc att tgg gtt gta ttg aaa gtt cga aca aca      2688
Pro Ser Val Asp Gln Gly Ile Trp Val Val Leu Lys Val Arg Thr Thr
            885                 890                 895

gat ggt tat gca acg cta gga aat ctt gaa ttg gta gaa gta gga tca      2736
Asp Gly Tyr Ala Thr Leu Gly Asn Leu Glu Leu Val Glu Val Gly Ser
            900                 905                 910

tta tcg ggt gaa tct ctg gaa cgt gaa aaa aga gaa aat gcg gaa tgg      2784
Leu Ser Gly Glu Ser Leu Glu Arg Glu Lys Arg Glu Asn Ala Glu Trp
        915                 920                 925

aat gca gag tta gga aga aag cgt gca gaa aca gag cgc gta tat caa      2832
Asn Ala Glu Leu Gly Arg Lys Arg Ala Glu Thr Glu Arg Val Tyr Gln
    930                 935                 940

gct gcg aaa cga gca att aat cat cta ttt gta gac tat caa gat caa      2880
Ala Ala Lys Arg Ala Ile Asn His Leu Phe Val Asp Tyr Gln Asp Gln
945                 950                 955                 960

caa tta aat tta gaa gta ggg cta gcg gag att aat gaa gtt tca aat      2928
Gln Leu Asn Leu Glu Val Gly Leu Ala Glu Ile Asn Glu Val Ser Asn
            965                 970                 975

ctt gtg gag tca att ccg agt gta tat agt gat aca gta ttg caa att      2976
Leu Val Glu Ser Ile Pro Ser Val Tyr Ser Asp Thr Val Leu Gln Ile
            980                 985                 990

cct ggg gtt aac tac gaa att tac aca gag cta tcc aat cgc tta caa      3024
Pro Gly Val Asn Tyr Glu Ile Tyr Thr Glu Leu Ser Asn Arg Leu Gln
        995                 1000                1005

caa gca tcg tat ttg tat atg tct cga aat gcc gtg caa aat gga gac      3072
Gln Ala Ser Tyr Leu Tyr Met Ser Arg Asn Ala Val Gln Asn Gly Asp
    1010                1015                1020

ttt aac aat gga tta gat agt tgg aat gcg aca act gat gcg acg gtc      3120
Phe Asn Asn Gly Leu Asp Ser Trp Asn Ala Thr Thr Asp Ala Thr Val
1025                1030                1035                1040

cag cag gat ggc act atg cat ttc tta gtt ctt tcc cat tgg gat gca      3168
Gln Gln Asp Gly Thr Met His Phe Leu Val Leu Ser His Trp Asp Ala
            1045                1050                1055

caa gtt tct cag ccg ttg aga gta cag cca aat tgt aag tat gta tta      3216
Gln Val Ser Gln Pro Leu Arg Val Gln Pro Asn Cys Lys Tyr Val Leu
            1060                1065                1070

cgt gtg aca gca aga aaa gta ggc agc gga gac ggg tac gtc aca att      3264
Arg Val Thr Ala Arg Lys Val Gly Ser Gly Asp Gly Tyr Val Thr Ile
        1075                1080                1085

cga aat ggt gct cat cac cac gaa acc ctt ata ttt aat gca tgt gac      3312
Arg Asn Gly Ala His His His Glu Thr Leu Ile Phe Asn Ala Cys Asp
    1090                1095                1100

tat gat ata aat ggt acg tat gta aat gaa aat acg tat att aca aaa      3360
Tyr Asp Ile Asn Gly Thr Tyr Val Asn Glu Asn Thr Tyr Ile Thr Lys
1105                1110                1115                1120

gaa gtg gta ttt tat cct cat aca gaa cat acg tgg gta gag gtg agt      3408
Glu Val Val Phe Tyr Pro His Thr Glu His Thr Trp Val Glu Val Ser
            1125                1130                1135

gaa tcc gaa ggt gca ttc tat ata gac agt att gag ttg att gaa aca      3456
Glu Ser Glu Gly Ala Phe Tyr Ile Asp Ser Ile Glu Leu Ile Glu Thr
            1140                1145                1150
```

-continued

```
caa gag tag                                                         3465
Gln Glu  *


<210> SEQ ID NO 27
<211> LENGTH: 1154
<212> TYPE: PRT
<213> ORGANISM: Bacillus thuringiensis

<400> SEQUENCE: 27

Met Asn Arg Asn Asn Gln Asn Glu Tyr Glu Ile Ile Asp Gly Thr Asn
 1               5                  10                  15

Cys Asp Cys Ser Ser Asp Glu Val Val Lys Tyr Pro Leu Ala Ser Glu
            20                  25                  30

Gln Asn Gly Val Leu Gln Asn Met Asn Tyr Lys Glu Tyr Leu Gln Thr
        35                  40                  45

Tyr Asp Gly Asp Tyr Thr Gly Ser Leu Ile Asn Pro Asn Leu Ser Ile
    50                  55                  60

Asn Thr Arg Asp Val Leu Gln Thr Gly Ile Thr Ile Val Gly Arg Val
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asn Asn Ala Val Trp
            100                 105                 110

Glu Ala Phe Met Ala Gln Val Glu Glu Leu Ile Asp Gln Arg Ile Ser
        115                 120                 125

Asp Gln Val Val Arg Asn Ala Leu Asp Asp Leu Thr Gly Leu His Asp
    130                 135                 140

Tyr Tyr Asn Glu Tyr Leu Ala Ala Leu Glu Glu Trp Leu Asp Arg Pro
145                 150                 155                 160

Asn Gly Ala Arg Ala Asn Leu Ala Phe Gln Arg Phe Glu Asn Leu His
                165                 170                 175

Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Gln Gln Ser Gln Ile Asn Leu Tyr Phe Asn Ala Gln Gln Asp
225                 230                 235                 240

Arg Thr Arg Ile Tyr Thr Asn His Cys Val Ala Thr Tyr Asn Arg Gly
                245                 250                 255

Leu Glu Asp Leu Lys Gly Thr Asn Thr Glu Ser Trp Tyr Asn Tyr His
            260                 265                 270

Gln Phe Arg Arg Glu Met Thr Leu Met Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Ile Tyr Thr Asp Pro Val Val Phe Asn Pro Pro Ala
305                 310                 315                 320

Asn Gln Gly Leu Cys Arg Arg Trp Gly Asn Asn Pro Tyr Met Thr Phe
                325                 330                 335

Ser Gly Leu Glu Asn Ala Phe Ile Arg Pro Pro His Leu Phe Asp Arg
            340                 345                 350

Leu Asn Ser Leu Thr Ile Asn Ser His Arg Phe Pro Ile Ser Ser Asn
        355                 360                 365
```

-continued

```
Phe Met Asp Tyr Trp Ala Gly His Thr Leu Arg Arg Ser Tyr Met Asn
    370                 375                 380

Asn Ser Ala Val Gln Glu Asp Ser Tyr Gly Ala Ile Thr Pro Thr Arg
385                 390                 395                 400

Val Thr Ile Asn Pro Gly Val Asn Gly Thr Asn His Ile Glu Ser Thr
                405                 410                 415

Ala Val Asp Phe Arg Ser Gly Leu Val Gly Ile Tyr Gly Val His Arg
            420                 425                 430

Ala Ser Phe Val Pro Gly Gly Leu Phe Asn Gly Thr Ile Ser Pro Ala
        435                 440                 445

Asn Ala Gly Cys Arg Asn Leu His Asp Thr Arg Asp Val Leu Pro Leu
    450                 455                 460

Glu Glu Asn Asn Gly Ser Pro Ser His Arg Leu Ser His Val Thr Phe
465                 470                 475                 480

Leu Ser Phe Gln Thr Asn Gln Ala Gly Ser Leu Ala Asn Gly Gly Ser
                485                 490                 495

Val Pro Leu Tyr Val Trp Ala Arg Gln Asp Ile Asp Phe Asn Asn Thr
            500                 505                 510

Ile Thr Ala Asn Arg Ile Thr Gln Leu Pro Leu Val Lys Ala Phe Glu
        515                 520                 525

Ile Ala Ala Gly Thr Thr Ile Val Lys Gly Pro Gly Phe Thr Gly Gly
    530                 535                 540

Asp Ile Leu Arg Arg Thr Ser Thr Gly Thr Leu Gly Thr Ile Arg Val
545                 550                 555                 560

Asn Val Asn Ser Pro Leu Thr Gln Arg Tyr Arg Val Arg Phe Arg Tyr
                565                 570                 575

Ala Ser Thr Val Asp Phe Asp Phe Phe Val Ser Arg Gly Gly Thr Thr
            580                 585                 590

Val Asn Asn Phe Arg Phe Pro Arg Thr Met Ser Arg Gly Gln Glu Ser
        595                 600                 605

Arg Tyr Glu Ser Tyr Val Thr Ser Glu Phe Thr Thr Pro Phe Thr Phe
    610                 615                 620

Thr Gln Ser Gln Asp Phe Ile Arg Thr Ser Ile Gln Gly Leu Ser Gly
625                 630                 635                 640

Asn Gly Glu Val Tyr Leu Asp Arg Ile Glu Ile Ile Pro Val Asn Pro
                645                 650                 655

Ala Arg Glu Ala Glu Glu Asp Leu Glu Ala Ala Lys Lys Ala Val Ala
            660                 665                 670

Ser Leu Phe Thr Arg Thr Arg Asp Gly Leu Gln Val Asn Val Thr Asp
        675                 680                 685

Tyr Gln Val Asp Gln Ala Ala Asn Leu Val Ser Cys Leu Ser Asp Glu
    690                 695                 700

Gln Tyr Gly His Asp Lys Lys Met Leu Leu Glu Ala Val Arg Ala Ala
705                 710                 715                 720

Lys Arg Leu Ser Arg Glu Arg Asn Leu Leu Gln Asp Pro Asp Phe Asn
                725                 730                 735

Glu Ile Asn Ser Ile Glu Glu Asn Gly Trp Lys Ala Ser Asn Gly Val
            740                 745                 750

Thr Ile Ser Glu Gly Gly Pro Phe Phe Lys Gly Arg Ala Leu Gln Leu
        755                 760                 765

Ala Ser Ala Arg Glu Asn Tyr Pro Thr Tyr Ile Tyr Gln Lys Val Asp
    770                 775                 780
```

-continued

Ala Ser Val Leu Lys Pro Tyr Thr Arg Tyr Arg Leu Asp Gly Phe Val
785 790 795 800

Lys Ser Ser Gln Asp Leu Glu Ile Asp Leu Ile His His His Lys Val
805 810 815

His Leu Val Lys Asn Val Pro Asp Asn Leu Val Ser Asp Thr Tyr Ser
820 825 830

Asp Gly Ser Cys Ser Gly Ile Asn Arg Cys Asp Glu Gln His Gln Val
835 840 845

Asp Met Gln Leu Asp Ala Glu His His Pro Met Asp Cys Cys Glu Ala
850 855 860

Ala Glu Thr His Glu Phe Ser Ser Tyr Ile Asp Thr Gly Asp Leu Asn
865 870 875 880

Pro Ser Val Asp Gln Gly Ile Trp Val Val Leu Lys Val Arg Thr Thr
885 890 895

Asp Gly Tyr Ala Thr Leu Gly Asn Leu Glu Leu Val Glu Val Gly Ser
900 905 910

Leu Ser Gly Glu Ser Leu Glu Arg Glu Lys Arg Glu Asn Ala Glu Trp
915 920 925

Asn Ala Glu Leu Gly Arg Lys Arg Ala Glu Thr Glu Arg Val Tyr Gln
930 935 940

Ala Ala Lys Arg Ala Ile Asn His Leu Phe Val Asp Tyr Gln Asp Gln
945 950 955 960

Gln Leu Asn Leu Glu Val Gly Leu Ala Glu Ile Asn Glu Val Ser Asn
965 970 975

Leu Val Glu Ser Ile Pro Ser Val Tyr Ser Asp Thr Val Leu Gln Ile
980 985 990

Pro Gly Val Asn Tyr Glu Ile Tyr Thr Glu Leu Ser Asn Arg Leu Gln
995 1000 1005

Gln Ala Ser Tyr Leu Tyr Met Ser Arg Asn Ala Val Gln Asn Gly Asp
1010 1015 1020

Phe Asn Asn Gly Leu Asp Ser Trp Asn Ala Thr Thr Asp Ala Thr Val
1025 1030 1035 1040

Gln Gln Asp Gly Thr Met His Phe Leu Val Leu Ser His Trp Asp Ala
1045 1050 1055

Gln Val Ser Gln Pro Leu Arg Val Gln Pro Asn Cys Lys Tyr Val Leu
1060 1065 1070

Arg Val Thr Ala Arg Lys Val Gly Ser Gly Asp Gly Tyr Val Thr Ile
1075 1080 1085

Arg Asn Gly Ala His His His Glu Thr Leu Ile Phe Asn Ala Cys Asp
1090 1095 1100

Tyr Asp Ile Asn Gly Thr Tyr Val Asn Glu Asn Thr Tyr Ile Thr Lys
1105 1110 1115 1120

Glu Val Val Phe Tyr Pro His Thr Glu His Thr Trp Val Glu Val Ser
1125 1130 1135

Glu Ser Glu Gly Ala Phe Tyr Ile Asp Ser Ile Glu Leu Ile Glu Thr
1140 1145 1150

Gln Glu

<210> SEQ ID NO 28
<211> LENGTH: 2358
<212> TYPE: DNA
<213> ORGANISM: Bacillus thuringiensis
<220> FEATURE:
<221> NAME/KEY: CDS
<222> LOCATION: (1)...(2343)

-continued

```
<400> SEQUENCE: 28

atg aat cga aat cat caa aat gaa tat gaa att att gat gcc cct cat        48
Met Asn Arg Asn His Gln Asn Glu Tyr Glu Ile Ile Asp Ala Pro His
 1               5                  10                  15

tgt gga tgt ccg tca gat gat gtt gtg aaa tat cct ttg aca gat gat        96
Cys Gly Cys Pro Ser Asp Asp Val Val Lys Tyr Pro Leu Thr Asp Asp
            20                  25                  30

ccg aat gct gga ttg caa aat atg aac tat aag gaa tat tta caa atg       144
Pro Asn Ala Gly Leu Gln Asn Met Asn Tyr Lys Glu Tyr Leu Gln Met
        35                  40                  45

tat ggt ggg gac tat aca gac cct ctt att aat cct aac tta tct gtt       192
Tyr Gly Gly Asp Tyr Thr Asp Pro Leu Ile Asn Pro Asn Leu Ser Val
    50                  55                  60

agt gga aaa gat gta ata caa gtt gga att aat att gta ggg aga tta       240
Ser Gly Lys Asp Val Ile Gln Val Gly Ile Asn Ile Val Gly Arg Leu
 65                 70                  75                  80

cta agc ttt ttt gga ttc ccc ttt tct agt caa tgg gtt aca gta tat       288
Leu Ser Phe Phe Gly Phe Pro Phe Ser Ser Gln Trp Val Thr Val Tyr
                85                  90                  95

acc tat ctt tta aac agc ttg tgg ccg gat gac gag aat tct gtt tgg       336
Thr Tyr Leu Leu Asn Ser Leu Trp Pro Asp Asp Glu Asn Ser Val Trp
            100                 105                 110

gat gct ttt atg aag aga ata gaa gaa ctt att gat caa aaa atc tca       384
Asp Ala Phe Met Lys Arg Ile Glu Glu Leu Ile Asp Gln Lys Ile Ser
        115                 120                 125

gaa gca gta aag ggt aga gca ttg gat gag cta act gga tta caa gat       432
Glu Ala Val Lys Gly Arg Ala Leu Asp Glu Leu Thr Gly Leu Gln Asp
    130                 135                 140

aat tat aat tta tat gta gaa gca tta gat gag tgg ctg aat aga cca       480
Asn Tyr Asn Leu Tyr Val Glu Ala Leu Asp Glu Trp Leu Asn Arg Pro
145                 150                 155                 160

aat ggc gca agg gca tcc tta gtt tct cag cga ttt aac att tta gat       528
Asn Gly Ala Arg Ala Ser Leu Val Ser Gln Arg Phe Asn Ile Leu Asp
                165                 170                 175

agc tta ttt aca caa ttt atg cca agc ttt ggc tct ggt cct gga agt       576
Ser Leu Phe Thr Gln Phe Met Pro Ser Phe Gly Ser Gly Pro Gly Ser
            180                 185                 190

caa aat tat tca act ata tta ctt cca gta tat gca caa gca gca aac       624
Gln Asn Tyr Ser Thr Ile Leu Leu Pro Val Tyr Ala Gln Ala Ala Asn
        195                 200                 205

ctt cat ttg tta tta tta aaa gat gca gac att tat gga gct aga tgg       672
Leu His Leu Leu Leu Leu Lys Asp Ala Asp Ile Tyr Gly Ala Arg Trp
    210                 215                 220

ggg ctg aat caa act caa att gat caa ttc cat tct cgt caa caa agc       720
Gly Leu Asn Gln Thr Gln Ile Asp Gln Phe His Ser Arg Gln Gln Ser
225                 230                 235                 240

ctt act cgg act tat aca aat cat tgt gtt act acg tat aat gat gga       768
Leu Thr Arg Thr Tyr Thr Asn His Cys Val Thr Thr Tyr Asn Asp Gly
                245                 250                 255

tta gcg gaa tta aga ggc aca agc gtt gag agt tgg ctc aaa tat cat       816
Leu Ala Glu Leu Arg Gly Thr Ser Val Glu Ser Trp Leu Lys Tyr His
            260                 265                 270

caa tat cgt agg gaa atg aca gta acg gct atg gat tta gtg gca tta       864
Gln Tyr Arg Arg Glu Met Thr Val Thr Ala Met Asp Leu Val Ala Leu
        275                 280                 285

ttc cca tac tat aat gtt cga caa tat cca aat gga gca aat cca caa       912
Phe Pro Tyr Tyr Asn Val Arg Gln Tyr Pro Asn Gly Ala Asn Pro Gln
    290                 295                 300
```

-continued

```
ctt aca cgt gag gta tat aca gat cca atc gta ttt aat cca ccg gag      960
Leu Thr Arg Glu Val Tyr Thr Asp Pro Ile Val Phe Asn Pro Pro Glu
305                 310                 315                 320

cct cca agt ggc gct ttc tgc gaa agt ttt tat aat atc cga gcg gct     1008
Pro Pro Ser Gly Ala Phe Cys Glu Ser Phe Tyr Asn Ile Arg Ala Ala
                325                 330                 335

cga gaa cgc tta act ttt tcg caa ctt gaa aat gca ata att cgt cca     1056
Arg Glu Arg Leu Thr Phe Ser Gln Leu Glu Asn Ala Ile Ile Arg Pro
            340                 345                 350

ccg cgc ttg ttt gaa agg ttt caa gct tta ggg att tat aca ggc gag     1104
Pro Arg Leu Phe Glu Arg Phe Gln Ala Leu Gly Ile Tyr Thr Gly Glu
        355                 360                 365

gcg cgg ctg aat caa aat agt gct cca acg aac tat tgg att gga cat     1152
Ala Arg Leu Asn Gln Asn Ser Ala Pro Thr Asn Tyr Trp Ile Gly His
    370                 375                 380

ttt ata aga aat aca cgt tta ggg gac tca aca aca att act aca aat     1200
Phe Ile Arg Asn Thr Arg Leu Gly Asp Ser Thr Thr Ile Thr Thr Asn
385                 390                 395                 400

tat gga aca acc aat aat cgt tta act aat ttt att cct cct act acc     1248
Tyr Gly Thr Thr Asn Asn Arg Leu Thr Asn Phe Ile Pro Pro Thr Thr
                405                 410                 415

agt gat gtt tat caa att aat tca atc tca agt aat tta gcc tct gct     1296
Ser Asp Val Tyr Gln Ile Asn Ser Ile Ser Ser Asn Leu Ala Ser Ala
            420                 425                 430

tta agc act tta ttt ggg gtt act aga gca caa ttc cat tat gga tca     1344
Leu Ser Thr Leu Phe Gly Val Thr Arg Ala Gln Phe His Tyr Gly Ser
        435                 440                 445

gga att att tgg tcg tat gtc gga caa aat aac gtt ctt cca caa tgt     1392
Gly Ile Ile Trp Ser Tyr Val Gly Gln Asn Asn Val Leu Pro Gln Cys
    450                 455                 460

cat caa aac tat aat tca ata gaa gaa tta cca aac caa agc gat gaa     1440
His Gln Asn Tyr Asn Ser Ile Glu Glu Leu Pro Asn Gln Ser Asp Glu
465                 470                 475                 480

cct aca gtt aga agt tat agc cat aga tta tct cat atc acc tct ttt     1488
Pro Thr Val Arg Ser Tyr Ser His Arg Leu Ser His Ile Thr Ser Phe
                485                 490                 495

aat ttc agt gta cag ctt aat aat cct gta att tct ctt ggc aat atg     1536
Asn Phe Ser Val Gln Leu Asn Asn Pro Val Ile Ser Leu Gly Asn Met
            500                 505                 510

cct gta tat gtg tgg aca cat cgc agt gtg gac ctt aat aac aca att     1584
Pro Val Tyr Val Trp Thr His Arg Ser Val Asp Leu Asn Asn Thr Ile
        515                 520                 525

act tca gat aga att act caa tta cca gcg gta aag gca tcg aca cta     1632
Thr Ser Asp Arg Ile Thr Gln Leu Pro Ala Val Lys Ala Ser Thr Leu
    530                 535                 540

ggt gcg gga gct att gtc gtg aaa ggt cca gga ttt aca gga gga gat     1680
Gly Ala Gly Ala Ile Val Val Lys Gly Pro Gly Phe Thr Gly Gly Asp
545                 550                 555                 560

gta atc cga aga aca tct gtt ggt gat ttc gga aca ata aga gtg tcg     1728
Val Ile Arg Arg Thr Ser Val Gly Asp Phe Gly Thr Ile Arg Val Ser
                565                 570                 575

gtt act ggc tcg cta act cag caa tat cgc ata agg ttc cgt tat gct     1776
Val Thr Gly Ser Leu Thr Gln Gln Tyr Arg Ile Arg Phe Arg Tyr Ala
            580                 585                 590

tcg aca ata gat ttt gat ttc ttt gta ata cgt gga gga act act ata     1824
Ser Thr Ile Asp Phe Asp Phe Phe Val Ile Arg Gly Gly Thr Thr Ile
        595                 600                 605

aat aat ttt aga ttc aca cat aca atg agc agt gga gag gaa tca aga     1872
Asn Asn Phe Arg Phe Thr His Thr Met Ser Ser Gly Glu Glu Ser Arg
    610                 615                 620
```

-continued tat gaa tcc tat cgt act gta gag ttt tcc act cct ttt aac ttt aca 1920
Tyr Glu Ser Tyr Arg Thr Val Glu Phe Ser Thr Pro Phe Asn Phe Thr
625 630 635 640 caa agt caa gat ata att cga aca tct atc cag gga ctt agt gga aat 1968
Gln Ser Gln Asp Ile Ile Arg Thr Ser Ile Gln Gly Leu Ser Gly Asn
645 650 655 ggg gaa gta tat ctt gat aga att gaa atc att cct gtg aat ccg aca 2016
Gly Glu Val Tyr Leu Asp Arg Ile Glu Ile Ile Pro Val Asn Pro Thr
660 665 670 cga gaa gca gaa gag gat cta gaa gat gca aag aaa gcg gtg gca ggc 2064
Arg Glu Ala Glu Glu Asp Leu Glu Asp Ala Lys Lys Ala Val Ala Gly
675 680 685 ttg ttt aca cgt aca aga gat gga tta cag gta aat gtg aca gat tac 2112
Leu Phe Thr Arg Thr Arg Asp Gly Leu Gln Val Asn Val Thr Asp Tyr
690 695 700 caa gtg gat cga gcg gca aat tta gtg tca tgc tta tca gat gaa caa 2160
Gln Val Asp Arg Ala Ala Asn Leu Val Ser Cys Leu Ser Asp Glu Gln
705 710 715 720 tat tcg cat gat aaa aaa atg cta atg gaa gct gta cgc gcg gca aaa 2208
Tyr Ser His Asp Lys Lys Met Leu Met Glu Ala Val Arg Ala Ala Lys
725 730 735 cgt ctc agc cga gaa cgc aat tta ctt cag gat ccg gat ttc aat gaa 2256
Arg Leu Ser Arg Glu Arg Asn Leu Leu Gln Asp Pro Asp Phe Asn Glu
740 745 750 ata aat agt acg gaa gag aat ggt tgg aaa gca agt aac ggt att atc 2304
Ile Asn Ser Thr Glu Glu Asn Gly Trp Lys Ala Ser Asn Gly Ile Ile
755 760 765 att agc gag ggc ggt cca ttc ttt aaa ggc cgt gtc taa taagtcgacc 2353
Ile Ser Glu Gly Gly Pro Phe Phe Lys Gly Arg Val *
770 775 780 tcgag 2358

<210> SEQ ID NO 29
<211> LENGTH: 780
<212> TYPE: PRT
<213> ORGANISM: Bacillus thuringiensis

<400> SEQUENCE: 29

Met Asn Arg Asn His Gln Asn Glu Tyr Glu Ile Ile Asp Ala Pro His
1 5 10 15

Cys Gly Cys Pro Ser Asp Asp Val Val Lys Tyr Pro Leu Thr Asp Asp
20 25 30

Pro Asn Ala Gly Leu Gln Asn Met Asn Tyr Lys Glu Tyr Leu Gln Met
35 40 45

Tyr Gly Gly Asp Tyr Thr Asp Pro Leu Ile Asn Pro Asn Leu Ser Val
50 55 60

Ser Gly Lys Asp Val Ile Gln Val Gly Ile Asn Ile Val Gly Arg Leu
65 70 75 80

Leu Ser Phe Phe Gly Phe Pro Phe Ser Ser Gln Trp Val Thr Val Tyr
85 90 95

Thr Tyr Leu Leu Asn Ser Leu Trp Pro Asp Asp Glu Asn Ser Val Trp
100 105 110

Asp Ala Phe Met Lys Arg Ile Glu Glu Leu Ile Asp Gln Lys Ile Ser
115 120 125

Glu Ala Val Lys Gly Arg Ala Leu Asp Glu Leu Thr Gly Leu Gln Asp
130 135 140

Asn Tyr Asn Leu Tyr Val Glu Ala Leu Asp Glu Trp Leu Asn Arg Pro

-continued

```
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
            180                 185                 190

Gln Asn Tyr Ser Thr Ile Leu Leu Pro Val Tyr Ala Gln Ala Ala Asn
        195                 200                 205

Leu His Leu Leu Leu Leu Lys Asp Ala Asp Ile Tyr Gly Ala Arg Trp
    210                 215                 220

Gly Leu Asn Gln Thr Gln Ile Asp Gln Phe His Ser Arg Gln Gln Ser
225                 230                 235                 240

Leu Thr Arg Thr Tyr Thr Asn His Cys Val Thr Thr Tyr Asn Asp Gly
                245                 250                 255

Leu Ala Glu Leu Arg Gly Thr Ser Val Glu Ser Trp Leu Lys Tyr His
            260                 265                 270

Gln Tyr Arg Arg Glu Met Thr Val Thr Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Val Tyr Thr Asp Pro Ile Val Phe Asn Pro Pro Glu
305                 310                 315                 320

Pro Pro Ser Gly Ala Phe Cys Glu Ser Phe Tyr Asn Ile Arg Ala Ala
                325                 330                 335

Arg Glu Arg Leu Thr Phe Ser Gln Leu Glu Asn Ala Ile Ile Arg Pro
            340                 345                 350

Pro Arg Leu Phe Glu Arg Phe Gln Ala Leu Gly Ile Tyr Thr Gly Glu
        355                 360                 365

Ala Arg Leu Asn Gln Asn Ser Ala Pro Thr Asn Tyr Trp Ile Gly His
    370                 375                 380

Phe Ile Arg Asn Thr Arg Leu Gly Asp Ser Thr Thr Ile Thr Thr Asn
385                 390                 395                 400

Tyr Gly Thr Thr Asn Asn Arg Leu Thr Asn Phe Ile Pro Pro Thr Thr
                405                 410                 415

Ser Asp Val Tyr Gln Ile Asn Ser Ile Ser Ser Asn Leu Ala Ser Ala
            420                 425                 430

Leu Ser Thr Leu Phe Gly Val Thr Arg Ala Gln Phe His Tyr Gly Ser
        435                 440                 445

Gly Ile Ile Trp Ser Tyr Val Gly Gln Asn Asn Val Leu Pro Gln Cys
    450                 455                 460

His Gln Asn Tyr Asn Ser Ile Glu Glu Leu Pro Asn Gln Ser Asp Glu
465                 470                 475                 480

Pro Thr Val Arg Ser Tyr Ser His Arg Leu Ser His Ile Thr Ser Phe
                485                 490                 495

Asn Phe Ser Val Gln Leu Asn Asn Pro Val Ile Ser Leu Gly Asn Met
            500                 505                 510

Pro Val Tyr Val Trp Thr His Arg Ser Val Asp Leu Asn Asn Thr Ile
        515                 520                 525

Thr Ser Asp Arg Ile Thr Gln Leu Pro Ala Val Lys Ala Ser Thr Leu
    530                 535                 540

Gly Ala Gly Ala Ile Val Val Lys Gly Pro Gly Phe Thr Gly Gly Asp
545                 550                 555                 560

Val Ile Arg Arg Thr Ser Val Gly Asp Phe Gly Thr Ile Arg Val Ser
                565                 570                 575
```

-continued

```
Val Thr Gly Ser Leu Thr Gln Gln Tyr Arg Ile Arg Phe Arg Tyr Ala
            580                 585                 590

Ser Thr Ile Asp Phe Asp Phe Phe Val Ile Arg Gly Gly Thr Thr Ile
        595                 600                 605

Asn Asn Phe Arg Phe Thr His Thr Met Ser Ser Gly Glu Glu Ser Arg
    610                 615                 620

Tyr Glu Ser Tyr Arg Thr Val Glu Phe Ser Thr Pro Phe Asn Phe Thr
625                 630                 635                 640

Gln Ser Gln Asp Ile Ile Arg Thr Ser Ile Gln Gly Leu Ser Gly Asn
                645                 650                 655

Gly Glu Val Tyr Leu Asp Arg Ile Glu Ile Ile Pro Val Asn Pro Thr
            660                 665                 670

Arg Glu Ala Glu Glu Asp Leu Glu Asp Ala Lys Lys Ala Val Ala Gly
        675                 680                 685

Leu Phe Thr Arg Thr Arg Asp Gly Leu Gln Val Asn Val Thr Asp Tyr
    690                 695                 700

Gln Val Asp Arg Ala Ala Asn Leu Val Ser Cys Leu Ser Asp Glu Gln
705                 710                 715                 720

Tyr Ser His Asp Lys Lys Met Leu Met Glu Ala Val Arg Ala Ala Lys
                725                 730                 735

Arg Leu Ser Arg Glu Arg Asn Leu Leu Gln Asp Pro Asp Phe Asn Glu
            740                 745                 750

Ile Asn Ser Thr Glu Glu Asn Gly Trp Lys Ala Ser Asn Gly Ile Ile
        755                 760                 765

Ile Ser Glu Gly Gly Pro Phe Phe Lys Gly Arg Val
    770                 775                 780


<210> SEQ ID NO 30
<211> LENGTH: 2295
<212> TYPE: DNA
<213> ORGANISM: Bacillus thuringiensis
<220> FEATURE:
<221> NAME/KEY: CDS
<222> LOCATION: (1)...(2295)

<400> SEQUENCE: 30

atg aat cga aat aat caa aat gaa tat gaa att att gac gga acc aat       48
Met Asn Arg Asn Asn Gln Asn Glu Tyr Glu Ile Ile Asp Gly Thr Asn
 1               5                  10                  15

tgt gat tgt tcg tca gat gag gtt gtg aaa tat cct tta gca agt gag       96
Cys Asp Cys Ser Ser Asp Glu Val Val Lys Tyr Pro Leu Ala Ser Glu
            20                  25                  30

caa aat ggt gtg tta caa aat atg aac tat aaa gaa tat tta caa acg      144
Gln Asn Gly Val Leu Gln Asn Met Asn Tyr Lys Glu Tyr Leu Gln Thr
        35                  40                  45

tat gat gga gac tat aca ggc tct ctt atc aat cct aac tta tct att      192
Tyr Asp Gly Asp Tyr Thr Gly Ser Leu Ile Asn Pro Asn Leu Ser Ile
     50                  55                  60

aat act aga gat gta cta caa act ggt att act att gta gga aga gta      240
Asn Thr Arg Asp Val Leu Gln Thr Gly Ile Thr Ile Val Gly Arg Val
 65                  70                  75                  80

cta ggg ttt tta ggt gtt cca ttt gct ggc caa tta gtt act ttc tat      288
Leu Gly Phe Leu Gly Val Pro Phe Ala Gly Gln Leu Val Thr Phe Tyr
                85                  90                  95

acg ttt ctc tta aat cag ttg tgg cca act aat aat aat gca gta tgg      336
Thr Phe Leu Leu Asn Gln Leu Trp Pro Thr Asn Asn Asn Ala Val Trp
            100                 105                 110
```

-continued

```
gaa gct ttt atg gca caa gta gaa gag ctt atc gac caa aga ata tcg      384
Glu Ala Phe Met Ala Gln Val Glu Glu Leu Ile Asp Gln Arg Ile Ser
        115                 120                 125

gat caa gta gta aga aat gca ctt gat gac cta act gga tta cac gat      432
Asp Gln Val Val Arg Asn Ala Leu Asp Asp Leu Thr Gly Leu His Asp
    130                 135                 140

tat tat aat gaa tat cta gcg gca tta gag gag tgg cta gat aga ccg      480
Tyr Tyr Asn Glu Tyr Leu Ala Ala Leu Glu Glu Trp Leu Asp Arg Pro
145                 150                 155                 160

aat ggc gcc aga gct aac tta gct ttt caa agg ttt gaa aac ctg cat      528
Asn Gly Ala Arg Ala Asn Leu Ala Phe Gln Arg Phe Glu Asn Leu His
                165                 170                 175

acc gca ttt gta act aga atg cca agt ttt gga act ggt cct ggt agt      576
Thr Ala Phe Val Thr Arg Met Pro Ser Phe Gly Thr Gly Pro Gly Ser
            180                 185                 190

caa aga gat gcg gta gca ttg ctg acg gta tat gca caa gca gcg aat      624
Gln Arg Asp Ala Val Ala Leu Leu Thr Val Tyr Ala Gln Ala Ala Asn
        195                 200                 205

ctc cat ttg tta tta tta aaa gat gca gaa att tat ggg gca aga tgg      672
Leu His Leu Leu Leu Leu Lys Asp Ala Glu Ile Tyr Gly Ala Arg Trp
    210                 215                 220

gga ctt caa caa agt cag att aac tta tat ttt aat gct caa caa gat      720
Gly Leu Gln Gln Ser Gln Ile Asn Leu Tyr Phe Asn Ala Gln Gln Asp
225                 230                 235                 240

cgt act cga att tat acc aat cat tgt gtg gca aca tat aat aga gga      768
Arg Thr Arg Ile Tyr Thr Asn His Cys Val Ala Thr Tyr Asn Arg Gly
                245                 250                 255

tta gaa gat tta aaa ggc aca aat acg gaa agt tgg tat aat tat cat      816
Leu Glu Asp Leu Lys Gly Thr Asn Thr Glu Ser Trp Tyr Asn Tyr His
            260                 265                 270

caa ttc cgt aga gag atg aca tta atg gca atg gat tta gta gcg tta      864
Gln Phe Arg Arg Glu Met Thr Leu Met Ala Met Asp Leu Val Ala Leu
        275                 280                 285

ttc cca tat tac aat gta cga caa tat cca aat ggg gca aat cct cag      912
Phe Pro Tyr Tyr Asn Val Arg Gln Tyr Pro Asn Gly Ala Asn Pro Gln
    290                 295                 300

ctt aca cgt gaa ata tat aca gat cca gtt gta ttt aat cca cca gcc      960
Leu Thr Arg Glu Ile Tyr Thr Asp Pro Val Val Phe Asn Pro Pro Ala
305                 310                 315                 320

aat cag gga ctt tgt aga cgt tgg gga aat aac cct tat atg aca ttt     1008
Asn Gln Gly Leu Cys Arg Arg Trp Gly Asn Asn Pro Tyr Met Thr Phe
                325                 330                 335

tcg gga ctt gag aat gct ttc att cgc cct ccg cat ctt ttt gat aga     1056
Ser Gly Leu Glu Asn Ala Phe Ile Arg Pro Pro His Leu Phe Asp Arg
            340                 345                 350

ttg aat agc tta aca att aac agc cat cga ttt ccc att tca tca aat     1104
Leu Asn Ser Leu Thr Ile Asn Ser His Arg Phe Pro Ile Ser Ser Asn
        355                 360                 365

ttt atg gat tat tgg gca gga cat acg tta cgc cgt agt tat atg aat     1152
Phe Met Asp Tyr Trp Ala Gly His Thr Leu Arg Arg Ser Tyr Met Asn
    370                 375                 380

aat tcg gca gta caa gaa gat agt tat ggc gcg atc act ccc aca aga     1200
Asn Ser Ala Val Gln Glu Asp Ser Tyr Gly Ala Ile Thr Pro Thr Arg
385                 390                 395                 400

gtc aca att aat ccc gga gtt aat gga aca aac cac ata gag tca acg     1248
Val Thr Ile Asn Pro Gly Val Asn Gly Thr Asn His Ile Glu Ser Thr
                405                 410                 415

gca gta gat ttt cgt tct ggt ctg gtg ggt ata tat ggc gtg cat aga     1296
Ala Val Asp Phe Arg Ser Gly Leu Val Gly Ile Tyr Gly Val His Arg
            420                 425                 430
```

-continued

```
gct tcg ttt gtc ccg ggc ggc tta ttt aat ggt acc att tct cct gct     1344
Ala Ser Phe Val Pro Gly Gly Leu Phe Asn Gly Thr Ile Ser Pro Ala
        435                 440                 445

aat gca ggg tgt aga aat ctg cat gat aca aga gac gta tta cca ttg     1392
Asn Ala Gly Cys Arg Asn Leu His Asp Thr Arg Asp Val Leu Pro Leu
    450                 455                 460

gaa gaa aat aac gga agc cct tcc cat aga tta tct cat gtt act ttt     1440
Glu Glu Asn Asn Gly Ser Pro Ser His Arg Leu Ser His Val Thr Phe
465                 470                 475                 480

tta agt ttt caa act aat cag gct ggg tct ctt gca aat ggt gga agc     1488
Leu Ser Phe Gln Thr Asn Gln Ala Gly Ser Leu Ala Asn Gly Gly Ser
                485                 490                 495

gta cct tta tat gtt tgg gca cgt caa gat ata gat ttt aat aac aca     1536
Val Pro Leu Tyr Val Trp Ala Arg Gln Asp Ile Asp Phe Asn Asn Thr
            500                 505                 510

att acc gca aat aga att aca caa cta cca ttg gta aag gca ttt gaa     1584
Ile Thr Ala Asn Arg Ile Thr Gln Leu Pro Leu Val Lys Ala Phe Glu
        515                 520                 525

ata gct gcg ggt act act atc gta aaa gga cca gga ttt aca gga ggg     1632
Ile Ala Ala Gly Thr Thr Ile Val Lys Gly Pro Gly Phe Thr Gly Gly
    530                 535                 540

gat ata ctt cga aga acg agc act ggt act tta gga aca ata aga gta     1680
Asp Ile Leu Arg Arg Thr Ser Thr Gly Thr Leu Gly Thr Ile Arg Val
545                 550                 555                 560

aat gtt aat tca ccg tta acg caa cga tat cgc gta aga ttc cgt tat     1728
Asn Val Asn Ser Pro Leu Thr Gln Arg Tyr Arg Val Arg Phe Arg Tyr
                565                 570                 575

gct tcg aca gta gat ttt gat ttc ttt gta tca cgt gga ggg act act     1776
Ala Ser Thr Val Asp Phe Asp Phe Phe Val Ser Arg Gly Gly Thr Thr
            580                 585                 590

gta aat aat ttt aga ttc cca cgt aca atg agc aga ggt cag gaa tca     1824
Val Asn Asn Phe Arg Phe Pro Arg Thr Met Ser Arg Gly Gln Glu Ser
        595                 600                 605

aga tac gaa tcc tat gtc aca agt gag ttt acg act cct ttt acc ttt     1872
Arg Tyr Glu Ser Tyr Val Thr Ser Glu Phe Thr Thr Pro Phe Thr Phe
    610                 615                 620

aca caa agt caa gat ttt att cga acg tct atc caa gga ctt agt ggg     1920
Thr Gln Ser Gln Asp Phe Ile Arg Thr Ser Ile Gln Gly Leu Ser Gly
625                 630                 635                 640

aat gga gaa gtg tat ctt gat aga att gaa atc atc cca gtt aac ccg     1968
Asn Gly Glu Val Tyr Leu Asp Arg Ile Glu Ile Ile Pro Val Asn Pro
                645                 650                 655

gca cga gaa gcg gag gag gat tta gaa gcg gcg aag aaa gcg gtg gcg     2016
Ala Arg Glu Ala Glu Glu Asp Leu Glu Ala Ala Lys Lys Ala Val Ala
            660                 665                 670

agc ttg ttt aca cgt act aga gac gga tta cag gta aat gtg aca gat     2064
Ser Leu Phe Thr Arg Thr Arg Asp Gly Leu Gln Val Asn Val Thr Asp
        675                 680                 685

tat caa gtc gat caa gcg gca aat tta gtg tcg tgc tta tca gat gaa     2112
Tyr Gln Val Asp Gln Ala Ala Asn Leu Val Ser Cys Leu Ser Asp Glu
    690                 695                 700

caa tat ggg cat gat aaa aag atg tta ttg gaa gcc gta cgc gca gca     2160
Gln Tyr Gly His Asp Lys Lys Met Leu Leu Glu Ala Val Arg Ala Ala
705                 710                 715                 720

aaa cgc ctc agc cga gaa cgc aac ttg ctt caa gat cca gat ttt aat     2208
Lys Arg Leu Ser Arg Glu Arg Asn Leu Leu Gln Asp Pro Asp Phe Asn
                725                 730                 735

gaa ata aat agt ata gaa gag aat ggc tgg aag gca agt aac ggt gtt     2256
Glu Ile Asn Ser Ile Glu Glu Asn Gly Trp Lys Ala Ser Asn Gly Val
```

-continued 740 745 750 act att agc gag ggc ggg cca ttc ttt aaa ggt cgt gca 2295
Thr Ile Ser Glu Gly Gly Pro Phe Phe Lys Gly Arg Ala
755 760 765

<210> SEQ ID NO 31
<211> LENGTH: 765
<212> TYPE: PRT
<213> ORGANISM: Bacillus thuringiensis

<400> SEQUENCE: 31

Met Asn Arg Asn Asn Gln Asn Glu Tyr Glu Ile Ile Asp Gly Thr Asn
1 5 10 15

Cys Asp Cys Ser Ser Asp Glu Val Val Lys Tyr Pro Leu Ala Ser Glu
20 25 30

Gln Asn Gly Val Leu Gln Asn Met Asn Tyr Lys Glu Tyr Leu Gln Thr
35 40 45

Tyr Asp Gly Asp Tyr Thr Gly Ser Leu Ile Asn Pro Asn Leu Ser Ile
50 55 60

Asn Thr Arg Asp Val Leu Gln Thr Gly Ile Thr Ile Val Gly Arg Val
65 70 75 80

Leu Gly Phe Leu Gly Val Pro Phe Ala Gly Gln Leu Val Thr Phe Tyr
85 90 95

Thr Phe Leu Leu Asn Gln Leu Trp Pro Thr Asn Asn Asn Ala Val Trp
100 105 110

Glu Ala Phe Met Ala Gln Val Glu Glu Leu Ile Asp Gln Arg Ile Ser
115 120 125

Asp Gln Val Val Arg Asn Ala Leu Asp Asp Leu Thr Gly Leu His Asp
130 135 140

Tyr Tyr Asn Glu Tyr Leu Ala Ala Leu Glu Glu Trp Leu Asp Arg Pro
145 150 155 160

Asn Gly Ala Arg Ala Asn Leu Ala Phe Gln Arg Phe Glu Asn Leu His
165 170 175

Thr Ala Phe Val Thr Arg Met Pro Ser Phe Gly Thr Gly Pro Gly Ser
180 185 190

Gln Arg Asp Ala Val Ala Leu Leu Thr Val Tyr Ala Gln Ala Ala Asn
195 200 205

Leu His Leu Leu Leu Leu Lys Asp Ala Glu Ile Tyr Gly Ala Arg Trp
210 215 220

Gly Leu Gln Gln Ser Gln Ile Asn Leu Tyr Phe Asn Ala Gln Gln Asp
225 230 235 240

Arg Thr Arg Ile Tyr Thr Asn His Cys Val Ala Thr Tyr Asn Arg Gly
245 250 255

Leu Glu Asp Leu Lys Gly Thr Asn Thr Glu Ser Trp Tyr Asn Tyr His
260 265 270

Gln Phe Arg Arg Glu Met Thr Leu Met Ala Met Asp Leu Val Ala Leu
275 280 285

Phe Pro Tyr Tyr Asn Val Arg Gln Tyr Pro Asn Gly Ala Asn Pro Gln
290 295 300

Leu Thr Arg Glu Ile Tyr Thr Asp Pro Val Val Phe Asn Pro Pro Ala
305 310 315 320

Asn Gln Gly Leu Cys Arg Arg Trp Gly Asn Asn Pro Tyr Met Thr Phe
325 330 335

Ser Gly Leu Glu Asn Ala Phe Ile Arg Pro Pro His Leu Phe Asp Arg
340 345 350

-continued

```
Leu Asn Ser Leu Thr Ile Asn Ser His Arg Phe Pro Ile Ser Ser Asn
        355                 360                 365

Phe Met Asp Tyr Trp Ala Gly His Thr Leu Arg Arg Ser Tyr Met Asn
    370                 375                 380

Asn Ser Ala Val Gln Glu Asp Ser Tyr Gly Ala Ile Thr Pro Thr Arg
385                 390                 395                 400

Val Thr Ile Asn Pro Gly Val Asn Gly Thr Asn His Ile Glu Ser Thr
                405                 410                 415

Ala Val Asp Phe Arg Ser Gly Leu Val Gly Ile Tyr Gly Val His Arg
            420                 425                 430

Ala Ser Phe Val Pro Gly Gly Leu Phe Asn Gly Thr Ile Ser Pro Ala
        435                 440                 445

Asn Ala Gly Cys Arg Asn Leu His Asp Thr Arg Asp Val Leu Pro Leu
    450                 455                 460

Glu Glu Asn Asn Gly Ser Pro Ser His Arg Leu Ser His Val Thr Phe
465                 470                 475                 480

Leu Ser Phe Gln Thr Asn Gln Ala Gly Ser Leu Ala Asn Gly Gly Ser
                485                 490                 495

Val Pro Leu Tyr Val Trp Ala Arg Gln Asp Ile Asp Phe Asn Asn Thr
            500                 505                 510

Ile Thr Ala Asn Arg Ile Thr Gln Leu Pro Leu Val Lys Ala Phe Glu
        515                 520                 525

Ile Ala Ala Gly Thr Thr Ile Val Lys Gly Pro Gly Phe Thr Gly Gly
    530                 535                 540

Asp Ile Leu Arg Arg Thr Ser Thr Gly Thr Leu Gly Thr Ile Arg Val
545                 550                 555                 560

Asn Val Asn Ser Pro Leu Thr Gln Arg Tyr Arg Val Arg Phe Arg Tyr
                565                 570                 575

Ala Ser Thr Val Asp Phe Asp Phe Phe Val Ser Arg Gly Gly Thr Thr
            580                 585                 590

Val Asn Asn Phe Arg Phe Pro Arg Thr Met Ser Arg Gly Gln Glu Ser
        595                 600                 605

Arg Tyr Glu Ser Tyr Val Thr Ser Glu Phe Thr Thr Pro Phe Thr Phe
    610                 615                 620

Thr Gln Ser Gln Asp Phe Ile Arg Thr Ser Ile Gln Gly Leu Ser Gly
625                 630                 635                 640

Asn Gly Glu Val Tyr Leu Asp Arg Ile Glu Ile Ile Pro Val Asn Pro
                645                 650                 655

Ala Arg Glu Ala Glu Glu Asp Leu Glu Ala Ala Lys Lys Ala Val Ala
            660                 665                 670

Ser Leu Phe Thr Arg Thr Arg Asp Gly Leu Gln Val Asn Val Thr Asp
        675                 680                 685

Tyr Gln Val Asp Gln Ala Ala Asn Leu Val Ser Cys Leu Ser Asp Glu
    690                 695                 700

Gln Tyr Gly His Asp Lys Lys Met Leu Leu Glu Ala Val Arg Ala Ala
705                 710                 715                 720

Lys Arg Leu Ser Arg Glu Arg Asn Leu Leu Gln Asp Pro Asp Phe Asn
                725                 730                 735

Glu Ile Asn Ser Ile Glu Glu Asn Gly Trp Lys Ala Ser Asn Gly Val
            740                 745                 750

Thr Ile Ser Glu Gly Gly Pro Phe Phe Lys Gly Arg Ala
        755                 760                 765
```

-continued

<210> SEQ ID NO 32
<211> LENGTH: 244
<212> TYPE: PRT
<213> ORGANISM: Artificial Sequence
<220> FEATURE:
<223> OTHER INFORMATION: Pfam consensus sequence

<400> SEQUENCE: 32

```
Val Gln Ile Gly Leu Ser Ile Val Gly Thr Leu Leu Gly Ala Leu Gly
 1               5                  10                  15

Val Phe Pro Gly Gly Gly Phe Leu Val Gly Phe Tyr Ser Thr Leu Leu
            20                  25                  30

Asp Leu Leu Trp Pro Ser Asn Gly Pro Ser Asn Glu Asn Val Trp Glu
        35                  40                  45

Ala Phe Leu Glu Gln Val Glu Gln Leu Ile Asp Gln Arg Ile Ser Glu
    50                  55                  60

Tyr Val Arg Asn Arg Ala Ile Ala Arg Leu Glu Gly Leu Gly Asn Ser
65                  70                  75                  80

Tyr Asp Thr Glu Val Ile Tyr Leu Glu Ala Leu Glu Glu Trp Glu Lys
                85                  90                  95

Asn Pro Asn Asn Ala Arg Ser Arg Glu Ala Val Arg Thr Arg Phe Asn
            100                 105                 110

Ile Leu Asp Ser Leu Phe Val Asn Ala Ile Pro Ser Phe Ala Val Ser
        115                 120                 125

Ala Gly Tyr Ser Glu Asn Tyr Glu Val Leu Leu Leu Pro Val Tyr Ala
    130                 135                 140

Gln Ala Ala Asn Leu His Leu Leu Leu Leu Arg Asp Ala Val Ile Phe
145                 150                 155                 160

Gly Glu Arg Trp Gly Leu Thr Gln Ala Asp Ile Asn Ser Thr Leu Asp
                165                 170                 175

Glu Asp Asn Tyr Tyr Asn Arg Leu Leu Glu Arg Ile Lys Glu Tyr Thr
            180                 185                 190

Asp His Cys Val Asn Trp Tyr Asn Thr Gly Leu Asn Asn Leu Arg Gly
        195                 200                 205

Thr Asn Leu Asp Ala Glu Ser Trp Val Arg Tyr Asn Arg Tyr Arg Arg
    210                 215                 220

Glu Met Thr Leu Thr Val Leu Asp Leu Val Ala Leu Phe Pro Asn Tyr
225                 230                 235                 240

Asp Pro Arg Leu
```

<210> SEQ ID NO 33
<211> LENGTH: 242
<212> TYPE: PRT
<213> ORGANISM: Artificial Sequence
<220> FEATURE:
<223> OTHER INFORMATION: Pfam consensus sequence

<400> SEQUENCE: 33

```
Thr Lys Ser Gln Leu Thr Arg Glu Ile Tyr Thr Asp Pro Val Gly Glu
 1               5                  10                  15

Val Ser Pro Gly Ser Gly Leu Ser Glu Gly Leu Cys Arg Arg Trp Gly
            20                  25                  30

Ile Asn Asn Tyr Pro Arg Leu Thr Phe Ser Ala Leu Glu Asn Ala Leu
        35                  40                  45

Ile Arg Ser Pro His Leu Phe Asp Phe Leu Asn Ser Leu Thr Ile Tyr
    50                  55                  60
```

-continued

```
Thr Asn Ser Ser Arg Gly Pro Leu Asn Thr Thr Leu Asp Ile Asn Tyr
65                  70                  75                  80

Trp Ser Gly His Arg Val Thr Ser Ser Tyr Thr Gly Gly Ser Thr Leu
                85                  90                  95

Asn Asn Ile Ile Ser Ser Pro Leu Tyr Gly Asn Thr Thr Asn Thr Ala
            100                 105                 110

Glu Pro Pro Val Thr Ile Ser Pro Cys Phe Thr Asn Asn Asp Ile Tyr
        115                 120                 125

Arg Thr Leu Ser Ala Thr Ser Asn Arg Leu Ser Gly Asn Asn Ile Ile
    130                 135                 140

Gly Leu Asn Asn Pro Ile Asn Gly Val Thr Arg Val Asp Phe Tyr Gly
145                 150                 155                 160

Ala Asn Gly Thr Asn Ser Glu Ile Ser Ser Asn Thr Tyr Arg Ser Ser
                165                 170                 175

Lys Arg Gly Asn Gly Gly Gln Arg Thr Ile Asp Ser Ile Asp Glu Leu
            180                 185                 190

Pro Pro Glu Thr Thr Asn Glu Pro Ile Tyr Glu Ser Tyr Ser His Arg
        195                 200                 205

Leu Ser His Val Thr Phe Leu Arg Ser Asn Thr Thr Gln Gly Gly Ser
    210                 215                 220

Asp Ala Thr Arg Ala His Val Pro Val Phe Ser Trp Thr His Arg Ser
225                 230                 235                 240

Ala Asp


<210> SEQ ID NO 34
<211> LENGTH: 155
<212> TYPE: PRT
<213> ORGANISM: Artificial Sequence
<220> FEATURE:
<223> OTHER INFORMATION: Pfam consensus sequence

<400> SEQUENCE: 34

Ile Thr Gln Ile Pro Leu Val Lys Ala Tyr Asn Leu Ser Ser Gly Ala
 1               5                  10                  15

Ser Val Val Lys Gly Pro Gly Phe Thr Gly Gly Asp Ile Leu Arg Arg
            20                  25                  30

Thr Ser Ser Asn Gly Ser Phe Gly Thr Leu Arg Val Thr Thr Lys Leu
        35                  40                  45

Ile Asn Asn Pro Leu Ser Gln Arg Tyr Arg Ile Arg Ile Arg Tyr Ala
    50                  55                  60

Ser Thr Thr Asn Leu Arg Phe Ile Val Ser Leu Ile Gly Gly Thr Thr
65                  70                  75                  80

Ser Asn Gln Phe Asn Phe Pro Lys Thr Met Asn Arg Gly Asp Asn Tyr
                85                  90                  95

Glu Asp Leu Thr Tyr Glu Ser Phe Arg Tyr Ala Glu Phe Ser Thr Pro
            100                 105                 110

Val Phe Ser Pro Tyr Phe Ser Gly Ser Gln Asp Ile Leu Thr Asn Ile
        115                 120                 125

Ser Thr Leu Gly Ile Gln Gly Phe Ser Ser Gly Gly Asn Gln Glu Val
    130                 135                 140

Tyr Ile Asp Arg Ile Glu Phe Ile Pro Val Asn
145                 150                 155


<210> SEQ ID NO 35
<211> LENGTH: 227
<212> TYPE: PRT
```

-continued

<213> ORGANISM: Bacillus thuringiensis
<220> FEATURE:
<221> NAME/KEY: PEPTIDE
<222> LOCATION: (1)...(227)
<223> OTHER INFORMATION: Peptide corresponding to amino acids 70 to 296
      of SEQ ID NO:6

<400> SEQUENCE: 35

```
Ile Gln Val Gly Ile Asn Ile Val Gly Arg Leu Leu Ser Phe Phe Gly
 1               5                  10                  15

Phe Pro Phe Ser Ser Gln Trp Val Thr Val Tyr Thr Tyr Leu Leu Asn
            20                  25                  30

Ser Leu Trp Pro Asp Asp Glu Asn Ser Val Trp Asp Ala Phe Met Lys
        35                  40                  45

Arg Ile Glu Glu Leu Ile Asp Gln Lys Ile Ser Glu Ala Val Lys Gly
    50                  55                  60

Arg Ala Leu Asp Glu Leu Thr Gly Leu Gln Asp Asn Tyr Asn Leu Tyr
65                  70                  75                  80

Val Glu Ala Leu Asp Glu Trp Leu Asn Arg Pro Asn Gly Ala Arg Ala
                85                  90                  95

Ser Leu Val Ser Gln Arg Phe Asn Ile Leu Asp Ser Leu Phe Thr Gln
            100                 105                 110

Phe Met Pro Ser Phe Gly Ser Gly Pro Gly Ser Gln Asn Tyr Ser Thr
        115                 120                 125

Ile Leu Leu Pro Val Tyr Ala Gln Ala Ala Asn Leu His Leu Leu Leu
    130                 135                 140

Leu Lys Asp Ala Asp Ile Tyr Gly Ala Arg Trp Gly Leu Asn Gln Thr
145                 150                 155                 160

Gln Ile Asp Gln Phe His Ser Arg Gln Gln Ser Leu Thr Arg Thr Tyr
                165                 170                 175

Thr Asn His Cys Val Thr Thr Tyr Asn Asp Gly Leu Ala Glu Leu Arg
            180                 185                 190

Gly Thr Ser Val Glu Ser Trp Leu Lys Tyr His Gln Tyr Arg Arg Glu
        195                 200                 205

Met Thr Val Thr Ala Met Asp Leu Val Ala Leu Phe Pro Tyr Tyr Asn
    210                 215                 220

Val Arg Gln
225
```

<210> SEQ ID NO 36
<211> LENGTH: 223
<212> TYPE: PRT
<213> ORGANISM: Bacillus thuringiensis
<220> FEATURE:
<221> NAME/KEY: PEPTIDE
<222> LOCATION: (1)...(223)
<223> OTHER INFORMATION: Peptide corresponding to amino acids 301 to 523
      of SEQ ID NO:6

<400> SEQUENCE: 36

```
Ala Asn Pro Gln Leu Thr Arg Glu Val Tyr Thr Asp Pro Ile Val Phe
 1               5                  10                  15

Asn Pro Pro Glu Pro Pro Ser Gly Ala Phe Cys Glu Ser Phe Tyr Asn
            20                  25                  30

Ile Arg Ala Ala Arg Glu Arg Leu Thr Phe Ser Gln Leu Glu Asn Ala
        35                  40                  45

Ile Ile Arg Pro Pro Arg Leu Phe Glu Arg Phe Gln Ala Leu Gly Ile
    50                  55                  60
```

-continued

Tyr Thr Gly Glu Ala Arg Leu Asn Gln Asn Ser Ala Pro Thr Asn Tyr
65 70 75 80

Trp Ile Gly His Phe Ile Arg Asn Thr Arg Leu Gly Asp Ser Thr Thr
85 90 95

Ile Thr Thr Asn Tyr Gly Thr Thr Asn Asn Arg Leu Thr Asn Phe Ile
100 105 110

Pro Pro Thr Thr Ser Asp Val Tyr Gln Ile Asn Ser Ile Ser Ser Asn
115 120 125

Leu Ala Ser Ala Leu Ser Thr Leu Phe Gly Val Thr Arg Ala Gln Phe
130 135 140

His Tyr Gly Ser Gly Ile Ile Trp Ser Tyr Val Gly Gln Asn Asn Val
145 150 155 160

Leu Pro Gln Cys His Gln Asn Tyr Asn Ser Ile Glu Glu Leu Pro Asn
165 170 175

Gln Ser Asp Glu Pro Thr Val Arg Ser Tyr Ser His Arg Leu Ser His
180 185 190

Ile Thr Ser Phe Asn Phe Ser Val Gln Leu Asn Asn Pro Val Ile Ser
195 200 205

Leu Gly Asn Met Pro Val Tyr Val Trp Thr His Arg Ser Val Asp
210 215 220

<210> SEQ ID NO 37
<211> LENGTH: 138
<212> TYPE: PRT
<213> ORGANISM: Bacillus thuringiensis
<220> FEATURE:
<221> NAME/KEY: PEPTIDE
<222> LOCATION: (1)...(138)
<223> OTHER INFORMATION: Peptide corresponding to amino acids 533 to 670 of SEQ ID NO:6

<400> SEQUENCE: 37

Ile Thr Gln Leu Pro Ala Val Lys Ala Ser Thr Leu Gly Ala Gly Ala
1 5 10 15

Ile Val Val Lys Gly Pro Gly Phe Thr Gly Gly Asp Val Ile Arg Arg
20 25 30

Thr Ser Val Gly Asp Phe Gly Thr Ile Arg Val Ser Val Thr Gly Ser
35 40 45

Leu Thr Gln Gln Tyr Arg Ile Arg Phe Arg Tyr Ala Ser Thr Ile Asp
50 55 60

Phe Asp Phe Phe Val Ile Arg Gly Gly Thr Thr Ile Asn Asn Phe Arg
65 70 75 80

Phe Thr His Thr Met Ser Ser Gly Glu Glu Ser Arg Tyr Glu Ser Tyr
85 90 95

Arg Thr Val Glu Phe Ser Thr Pro Phe Asn Phe Thr Gln Ser Gln Asp
100 105 110

Ile Ile Arg Thr Ser Ile Gln Gly Leu Ser Gly Asn Gly Glu Val Tyr
115 120 125

Leu Asp Arg Ile Glu Ile Ile Pro Val Asn
130 135

<210> SEQ ID NO 38
<211> LENGTH: 4
<212> TYPE: PRT
<213> ORGANISM: Artificial Sequence -continued

```
<220> FEATURE:
<223> OTHER INFORMATION: Proteolytic site

<400> SEQUENCE: 38

Asn Gly Ser Arg
 1
```

*BACILLUS THURINGIENSIS CRY9* NUCLEIC ACIDS

CROSS-REFERENCE TO RELATED APPLICATIONS

This application is a divisional application of U.S. Utility application Ser. No. 11/018,615, filed Dec. 21, 2004, which claims the benefit of U.S. Provisional Application Ser. No. 60/531,807, filed Dec. 22, 2003, both of which are herein incorporated by reference in their entirety.

REFERENCE TO SEQUENCE LISTING SUBMITTED ON COMPACT DISC

The official copy of the sequence listing is submitted on compact disc (CD). Two CDs, labeled Copy 1 and Copy 2, containing an ASCII formatted sequence listing with a file named 312495 SEQLIST.TXT, created on Jun. 6, 2006, and having a size of 231 kilobytes are filed concurrently with the specification. The sequence listing contained on these compact discs is part of the specification and is herein incorporated by reference in its entirety.

FIELD OF THE INVENTION

The present invention relates to naturally-occurring and recombinant nucleic acids obtained from novel *Bacillus thuringiensis* Cry9-family genes that encode δ-endotoxins characterized by pesticidal activity against insect pests. Compositions and methods of the invention utilize the disclosed nucleic acids, and their encoded pesticidal polypeptides, to control plant pests.

BACKGROUND OF THE INVENTION

Insect pests are a major factor in the loss of the world's agricultural crops. For example, armyworm feeding, black cutworm damage, or European corn borer damage can be economically devastating to agricultural producers. Insect pest-related crop loss from European corn borer attacks on field and sweet corn alone has reached about one billion dollars a year in damage and control expenses.

Traditionally, the primary method for impacting insect pest populations such as black cutworm populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* and *Bacillus*

*papilliae* are among the most successful biocontrol agents discovered to date. Insect pathogenicity has also been attributed to strains of *B. larvae, B. lentimorbus, B. sphaericus* (Harwook, ed., ((1989) *Bacillus* (Plenum Press), 306) and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants have been genetically engineered to produce pesticidal proteins isolated from strains of *B. thuringiensis* and known as δ-endotoxins or Cry toxins (see, e.g., Aronson (2002) *Cell Mol. Life Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. In addition, potatoes genetically engineered to contain pesticidal Cry toxins have been sold to the American farmer. While they have proven to be very successful commercially, these genetically engineered, insect-resistant crop plants provide resistance to only a narrow range of the economically important insect pests.

Accordingly, there remains a need for new Bt toxins with a broader range of insecticidal activity against insect pests, e.g., toxins which are active against a greater variety of insects from the order Lepidoptera. In addition, there remains a need for biopesticides having activity against a variety of insect pests and for biopesticides which have improved insecticidal activity.

SUMMARY OF THE INVENTION

Compositions and methods are provided for impacting insect pests. More specifically, the invention relates to methods of impacting insects utilizing nucleic acids encoding δ-endotoxin genes to produce transformed microorganisms and plants that express a pesticidal polypeptide of the invention. The compositions and methods of the invention find use in agriculture for controlling pests of many crop plants. Such pests include agriculturally significant pests, such as, for example: European corn borer, e.g., *Ostrinia nubilalis*; corn earworm, e.g., *Helicoverpa zeae*; common stalk borer, e.g., *Papiapema nebris*; armyworm, e.g., *Pseudaletia unipuncta*; Southwestern corn borer, e.g., *Diatraea grandiosella*; black cutworm, e.g., *Agrotis ipsilon*; fall armyworm, e.g., *Spodoptera frugiperda*; beet armyworm, e.g., *Spodoptera exigua*; and diamond-back moth, e.g., *Plutella xylostella.*

The invention provides nucleic acids and fragments and variants thereof which encode polypeptides that possess pesticidal activity against insect pests. The wild-type (e.g., naturally occurring) nucleotide sequences of the invention, which were obtained from strains of *Bacillus thuringiensis*, encode novel members of the Cry9 family of α-endotoxins. The invention further provides fragments and variants of Cry 9 family nucleotide sequences that encode biologically active (e.g., pesticidal) polypeptides. In some embodiments, the nucleotide sequences encode polypeptides that are pesticidal for at least one insect belonging to the order Lepidoptera.

Other embodiments of the invention provide nucleic acids encoding truncated versions of a Cry9 family endotoxin that are characterized by pesticidal activity that is either equivalent to or improved relative to the activity of the corresponding full-length endotoxin. Some of the truncated nucleic acids of the invention can be referred to as either fragments or variants. In some embodiments, some of the nucleic acids of the invention are truncated at the 3' end or 5' end of a wild-type coding sequence. In other embodiments, nucleic acids of the invention comprise a contiguous sequence of nucleic acid residues derived from another coding sequence of the invention that have been truncated at both the 5' and 3' ends.

The invention also provides mutant nucleotide sequences and their encoded amino acid sequences that confer additional properties on a polypeptide encoded by or comprising them. For example, a mutant nucleotide sequence may encode a novel protease recognition site which renders a polypeptide containing it susceptible to digestion by the protease. See, e.g., copending U.S. application Ser. Nos. 10/606,320, filed Jun. 25, 2003, and Ser. No. 10/746,914, filed Dec. 24, 2003. These mutations may be placed in the context of a background sequence, such as a Cry9 family nucleic acid, to provide toxins that have been engineered to have improved and/or altered pesticidal activities. In this manner, the invention provides an array of mutations that may be used individually or in combination to provide improved properties to an engineered Bt toxin. The nucleic acids of the invention can be used to produce expression cassettes that can be used to produce transformed microorganisms. The resulting transformants can be used in the preparation of pesticidal compositions comprising a transformed microorganism, or for the production and isolation of pesticidal proteins. Thus, the invention further provides pesticidal compositions comprising pesticidal polypeptides and/or transformed microorganisms as well as methods for producing such compositions. The pesticidal compositions of the invention find use in agricultural methods for impacting pests.

The invention further provides isolated pesticidal (e.g., insecticidal) polypeptides encoded by either a naturally occurring, or a modified (e.g., mutagenized or manipulated) nucleic acid of the invention. In particular examples, pesticidal proteins of the invention include fragments of full-length δ-endotoxins and polypeptides that are produced from mutagenized nucleic acids designed to introduce particular amino acid sequences into the polypeptides of the invention. In particular embodiments, the polypeptides of the invention have enhanced pesticidal activity relative to the activity of the naturally occurring δ-endotoxin from which they are derived.

The nucleic acids of the invention can also be used to produce transgenic (e.g., transformed) plants that are characterized by genomes that comprise at least one stably incorporated nucleotide construct comprising a coding sequence of the invention operably linked to a promoter that drives expression of the encoded pesticidal polypeptide. Accordingly, transformed plant cells, plant tissues, plants, and seeds thereof are also provided.

In a particular embodiment, a transformed plant of the invention can be produced using a nucleic acid that has been optimized for increased expression in a host plant. For example, one of the pesticidal polypeptides of the invention can be back-translated to produce a nucleic acid comprising codons optimized for expression in a particular host, for example a crop plant such as a *Zea mays* plant. Expression of a coding sequence by such a transformed plant (e.g., dicot or monocot) will result in the production of a pesticidal polypeptide and confer increased insect resistance to the plant. In some embodiments, the invention provides transgenic plants expressing pesticidal polypeptides that find use in methods for impacting various insect pests.

BRIEF DESCRIPTION OF THE DRAWINGS

FIG. 1: Pileup of Cry9 family members, including Cry9 family sequences of the invention, with consensus sequence (SEQ ID NO: 22) indicated. The sequences shown in the figure are also set forth in the sequence listing: cry9aa1 (SEQ ID NO: 12); cry9aa2 (SEQ ID NO: 13); cry 9da1 (SEQ ID NO: 14); cry9da2 (SEQ ID NO: 15); cry9d_rv1 (SEQ ID NO: 6); cry 9_like (SEQ ID NO: 16); cry9_rv1 (SEQ ID NO: 2); cry9eb1 (SEQ ID NO: 17); cry9fa (SEQ ID NO: 23); cry9ea1 (SEQ ID NO: 18); cry9ea2 (SEQ ID NO: 19); cry9cal (SEQ ID NO: 20); cry9ba1 (SEQ ID NO: 21); and the consensus sequence (SEQ ID NO: 22).

FIG. 3: A comparison of exemplary endotoxins of the invention to Pfam consensus sequences for Endotoxin N (Pfam Accession No. PF03945; SEQ ID NO: 32, Endotoxin M (Pfam Accession No. PF00555; SEQ ID NO: 33), and Endotoxin C (Pfam Accession No. PF03944; SEQ ID NO: 34). The exemplary endotoxins presented in the figure comprise amino acid residues 70 to 296 (SEQ ID NO:35), residues 301 to 523 (SEQ ID NO:36), and residues 533 to 670 (SEQ ID NO:37) of the amino acid sequence set forth in SEQ ID NO:6. These Pfam consensus sequences were generated from an analysis of delta endotoxins, which are described in the Pfam annotations as a family of insecticidal toxins produced by *Bacillus* bacteria. Briefly, when an insect ingests these proteins, they are activated by proteolytic cleavage; the N terminus is cleaved in all of the proteins and a C-terminal extension is cleaved in some members. Once activated, the endotoxin binds to the gut epithelium and causes cell lysis, leading to death. The activated region of the delta endotoxin is composed of three structural domains. The N-terminal helical domain is involved in membrane insertion and pore formation. The second and third domains are involved in receptor binding.

DETAILED DESCRIPTION OF THE INVENTION

Figure 2:
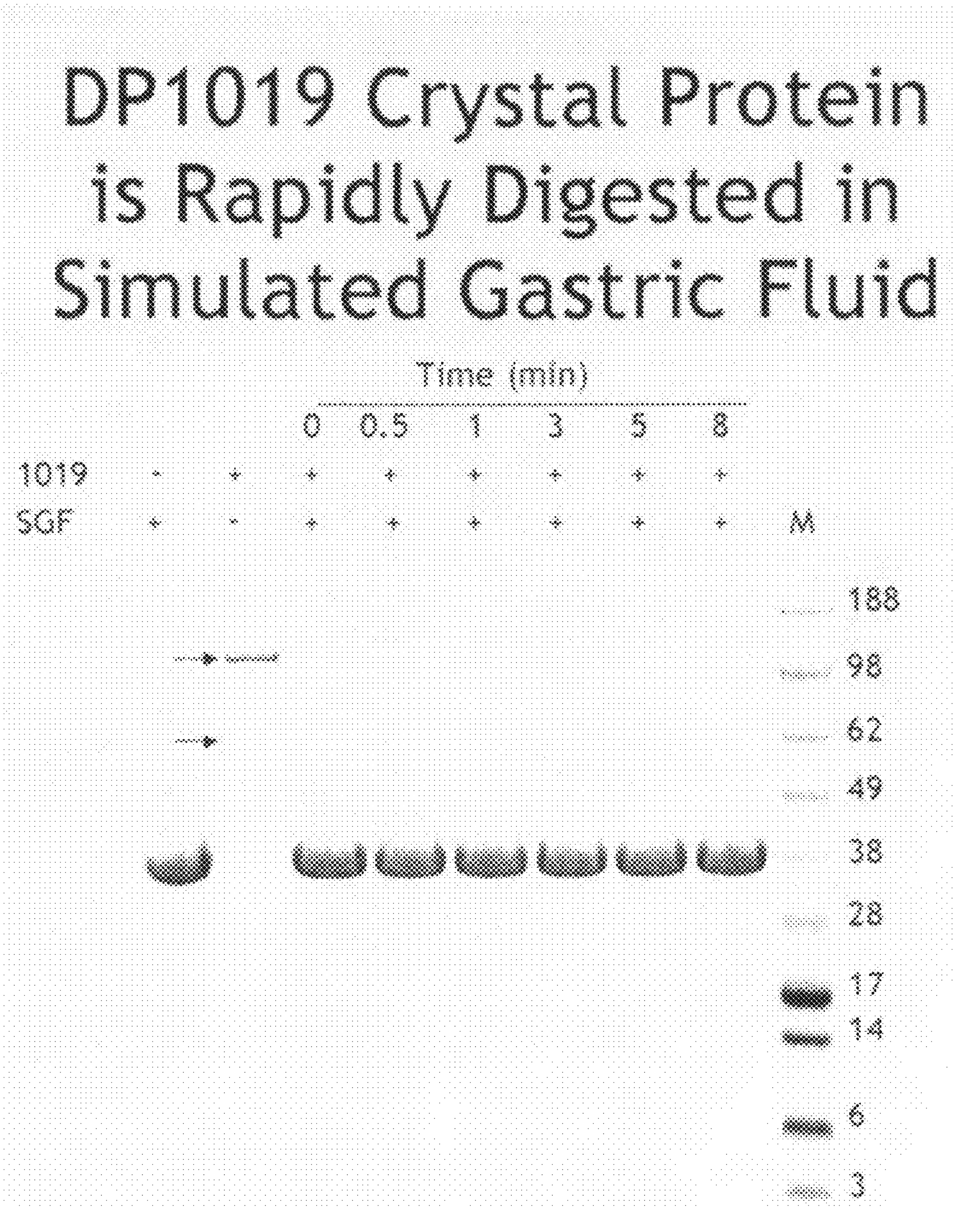
FIG. 2: Simulated Gastric Fluid (SGF) digestibility of DP1019 crystal protein. The results presented in FIG. 2 show that crystal protein from bacterial strain 1019 is rapidly digested in simulated gastric fluid (Astwood and Fuchs (1996) *Food Tech.* 50: 83-88; and Fu and Abbot (2002) *Agric. Food Chem.* 50: 7154-7160; see also Example 1). The incubation period of the digestion reaction is shown at the top of the gel, and molecular weight markers are shown on the right-hand side of the gel. Arrows indicate the full-length 1019 protein (110 kDa) and a 62 kDa fragment produced by digestion.

The invention is drawn to compositions and methods for impacting insect pests, particularly plant pests. More specifically, the isolated nucleic acids of the invention, and fragments and variants thereof, comprise nucleotide sequences that encode pesticidal polypeptides (e.g., proteins). The disclosed pesticidal proteins are biologically active (e.g., pesticidal) against insect pests such as, but not limited to, insect pests of the order Lepidoptera. Insect pests of interest include, but are not limited to: European corn borer, e.g., *Ostrinia nubilalis*; corn earworm, e.g., *Helicoverpa zeae*; common stalk borer, e.g., *Papiapema nebris*; armyworm, e.g., *Pseudaletia unipuncta*; Southwestern corn borer, e.g., *Diatraea grandiosella*; black cutworm, e.g., *Agrotis ipsilon*; fall armyworm, e.g., *Spodoptera frugiperda*; beet armyworm, e.g., *Spodoptera exigua*; and diamond-back moth, e.g., *Plutella xylostella.*

The compositions of the invention comprise isolated nucleic acids, and fragments and variants thereof, that encode pesticidal polypeptides, expression cassettes comprising nucleotide sequences of the invention, isolated pesticidal proteins, and pesticidal compositions. In some embodiments, the invention provides modified Cry9 family δ-endotoxin proteins characterized by improved insecticidal activity against Lepidopterans relative to the pesticidal activity of the corresponding wild-type protein. The invention further provides plants and microorganisms transformed with these novel nucleic acids, and methods involving the use of such nucleic acids, pesticidal compositions, transformed organisms, and products thereof in impacting insect pests.

The nucleic acids and nucleotide sequences of the invention may be used to transform any organism to produce the encoded pesticidal proteins. Methods are provided that involve the use of such transformed organisms to impact or control plant pests. The nucleic acids and nucleotide sequences of the invention may also be used to transform organelles such as chloroplasts (McBride et al. (1995) *Biotechnology* 13: 362-365; and Kota et al. (1999) *Proc. Natl. Acad. Sci. USA* 96: 1840-1845).

The invention further relates to the identification of fragments and variants of the naturally-occurring coding sequence that encode biologically active pesticidal proteins. The nucleotide sequences of the invention find direct use in methods for impacting pests, particularly insect pests such as pests of the order Lepidoptera. Accordingly, the present invention provides new approaches for impacting insect pests that do not depend on the use of traditional, synthetic chemical insecticides. The invention involves the discovery of naturally-occurring, biodegradable pesticides and the genes that encode them.

The invention further provides fragments and variants of the naturally occurring coding sequences that also encode biologically active (e.g., pesticidal) polypeptides. The nucleic acids of the invention encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The invention further provides mutations which confer improved or altered properties on the polypeptides of the invention. See, e.g., copending U.S. application Ser. Nos. 10/606,320, filed Jun. 25, 2003, and Ser. No. 10/746,914, filed Dec. 24, 2003.

In the description that follows, a number of terms are used extensively. The following definitions are provided to facilitate understanding of the invention.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is generally free of sequences (such as, for example, protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the invention means that the isolated protein is substantially free of cellular material and includes preparations of protein having less than about 30%, 20%, 10%, or 5% (by dry weight) of contaminating protein. When the protein of the invention or biologically active portion thereof is recombinantly produced, culture medium represents less than about 30%, 20%, 10%, or 5% (by dry weight) of chemical precursors or non-protein-of-interest chemicals.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

As used herein, the term "impacting insect pests" refers to effecting changes in insect feeding, growth, and/or behavior at any stage of development, including but not limited to: killing the insect; retarding growth; preventing reproductive capability; antifeedant activity; and the like.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins. Endotoxins are pesticidal proteins.

As used herein, the term "pesticidally effective amount" connotes a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

As used herein, the term "recombinantly engineered" or "engineered" connotes the utilization of recombinant DNA technology to introduce (e.g., engineer) a change in the protein structure based on an understanding of the protein's mechanism of action and a consideration of the amino acids being introduced, deleted, or substituted.

As used herein, the term "mutant nucleotide sequence" or "mutation" or "mutagenized nucleotide sequence" connotes a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a mutant δ-endotoxin showing improved or decreased insecticidal activity, or an amino acid sequence which confers improved or decreased insecticidal activity on a polypeptide containing it.

As used herein, the term "mutant" or "mutation" in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A mutant polypeptide shows improved or decreased insecticidal activity, or represents an amino acid sequence which confers improved insecticidal activity on a polypeptide containing it. Thus, the term "mutant" or "mutation" refers to either or both of the mutant nucleotide sequence and the encoded amino acids. Mutants may be used alone or in any compatible combination with other mutants of the invention or with other mutants. A "mutant polypeptide" may conversely show a decrease in insecticidal activity. Where more than one mutation is added to a particular nucleic acid or protein, the mutations may be added at the same time or sequentially; if sequentially, mutations may be added in any suitable order.

As used herein, the term "improved insecticidal activity" or "improved pesticidal activity" refers to a polypeptide or encoded polypeptide endotoxin of the invention that has enhanced Lepidopteran pesticidal activity relative to the activity of its corresponding wild-type protein, and/or an endotoxin that is effective against a broader range of insects, and/or an endotoxin having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type endotoxin determined against the same insect.

For example, an improved pesticidal or insecticidal activity is provided where a wider or narrower range of insects is impacted by the polypeptide relative to the range of insects that is affected by a wild-type Bt toxin such as, for example, Cry9 and the like. A wider range of impact may be desirable where versatility is desired, while a narrower range of impact may be desirable where, for example, beneficial insects might otherwise be impacted by use or presence of the toxin. While the invention is not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

The term "toxin" or "endotoxin" as used herein refers to a polypeptide showing pesticidal activity or insecticidal activity or improved pesticidal activity or improved insecticidal activity. In some instances, polypeptide endotoxins of the invention and the nucleotide sequences encoding them will share a high degree of sequence identity or similarity to wild-type Cry9 sequences. The term "Cry9 family" is used herein to refer to the nucleotide or amino acid sequences of the present invention, which share a high degree of sequence identity or similarity to previously described sequences categorized as Cry9 and/or Cry9D. "Bt" or "*Bacillus thuringiensis*" toxin or endotoxin is intended to include the broader class of Cry toxins found in various strains of *Bacillus thuringiensis*, which includes such toxins as, for example, Cry1s, Cry2s, or Cry3s.

The terms "proteolytic site" or "cleavage site" refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

Research has shown that the insect gut proteases of Lepidopterans include trypsins, chymotrypsins, and elastases. See, e.g., Lenz et al. (1991) *Arch. Insect Biochem. Physiol.* 16: 201-212; and Hedegus et al. (2003) *Arch. Insect Biochem. Physiol.* 53: 30-47. For example, about 18 different trypsins have been found in the midgut of *Helicoverpa armigera* larvae (see Gatehouse et al. (1997) *Insect Biochem. Mol. Biol.* 27: 929-944). The preferred proteolytic substrate sites of these proteases have been investigated. See, e.g., Peterson et al. (1995) *Insect Biochem. Mol. Biol.* 25: 765-774.

Efforts have been made to understand the mechanism of action of Bt toxins and to engineer toxins with improved properties. It has been shown that insect gut proteases can affect the impact of *Bacillus thuringiensis* Cry proteins on the insect. Some proteases activate the Cry proteins by processing them from a "protoxin" form into a toxic form, or "toxin." See, Oppert (1999) *Arch. Insect Biochem. Phys.* 42: 1-12; and Carroll et al. (1997) *J. Invertebrate Pathology* 70: 41-49. This activation of the toxin can include the removal of the N- and C-terminal peptides from the protein and can also include internal cleavage of the protein. Other proteases can degrade the Cry proteins. See Oppert, ibid.

It is well known that naturally-occurring δ-endotoxins are synthesized by *B. thuringiensis* sporulating cells as a proteinaceous crystalline inclusion protoxin. Upon being ingested by susceptible insect larvae, the microcrystals dissolve in the midgut, and the protoxin is transformed into a biologically active moiety by proteases characteristic of digestive enzymes located in the insect gut. The activated δ-endotoxin binds with high affinity to protein receptors on brush-border membrane vesicles. The epithelial cells lining the midgut are the primary target of the endotoxin and are rapidly destroyed as a consequence of membrane perforation resulting from the formation of gated, cation-selective channels by the toxin.

A comparison of the amino acid sequences of Cry toxins of different specificities reveals five highly-conserved sequence blocks. Structurally, the δ-endotoxins comprise three distinct domains which are, from the N- to C-terminus: a cluster of seven alpha-helices implicated in pore formation (referred to as "domain 1"), three anti-parallel beta sheets implicated in cell binding (referred to as "domain 2"), and a beta sandwich (referred to as "domain 3"). The location and properties of these domains are known to those of skill in the art. See, for example, Li et al. (1991) *Nature,* 305:815-821 and Morse et al. (2001) *Structure,* 9:409-417. When reference is made to a particular domain, such as domain 1, it is understood that the exact endpoints of the domain with regard to a particular sequence are not critical so long as the sequence or portion thereof includes sequence that provides at least some function attributed to the particular domain. Thus, for example, when referring to "domain 1," it is intended that a particular sequence includes a cluster of seven alpha-helices, but the exact endpoints of the sequence used or referred to with regard to that cluster are not critical. One of skill in the art is familiar with the determination of such endpoints and the evaluation of such functions.

In an effort to better characterize and improve Bt toxins, strains of the bacterium *Bacillus thuringiensis* were studied. Crystal preparations prepared from cultures of the *Bacillus thuringiensis* strains were discovered to have pesticidal activity against European corn borer (see, e.g., Experimental Examples 1, 2, and 3). An effort was undertaken to identify the nucleotide sequences encoding the crystal proteins from the selected strains, and the wild-type (i.e., naturally occurring) nucleic acids of the invention were isolated from these bacterial strains, cloned into an expression vector, and transformed into *Escherichia coli*. Depending upon the characteristics of a given preparation, it was recognized that the demonstration of pesticidal activity sometimes required trypsin pretreatment to activate the pesticidal proteins. Thus, it is understood that some pesticidal proteins require protease digestion (e.g., by trypsin, chymotrypsin, and the like) for activation, while other proteins are biologically active (e.g., pesticidal) in the absence of activation.

Such molecules may be altered by means described, for example, in U.S. application Ser. Nos. 10/606,320, filed Jun. 25, 2003, and Ser. No. 10/746,914, filed Dec. 24, 2003. In addition, nucleic acid sequences may be engineered to encode Cry9 family polypeptides that contain additional mutations that confer improved or altered pesticidal activity relative to the pesticidal activity of the naturally occurring polypeptide. The nucleotide sequences of such engineered nucleic acids comprise mutations not found in the wild type sequences.

The mutant Cry9 family polypeptides of the present invention are generally prepared by a process that involves the steps of: obtaining a nucleic acid sequence encoding a Cry9 family polypeptide; analyzing the structure of the polypeptide to identify particular "target" sites for mutagenesis of the underlying gene sequence based on a consideration of the proposed function of the target domain in the mode of action of the endotoxin; introducing one or more mutations into the nucleic acid sequence to produce a desired change in one or more amino acid residues of the encoded polypeptide sequence; and assaying the polypeptide produced for pesticidal activity.

Many of the δ-endotoxins are related to various degrees by similarities in their amino acid sequences and tertiary structure and means for obtaining the crystal structures of *B. thuringiensis* endotoxins are well known. Exemplary high-resolution crystal structure solution of both the Cry3A and Cry3B polypeptides are available in the literature. The solved structure of the Cry3A gene (Li et al. (1991) *Nature* 353:815-821) provides insight into the relationship between structure and function of the endotoxin. A combined consideration of the published structural analyses of *B. thuringiensis* endotoxins and the reported function associated with particular structures, motifs, and the like indicates that specific regions of the endotoxin are correlated with particular functions and discrete steps of the mode of action of the protein. For example, δ-endotoxins isolated from *B. thuringiensis* are generally described as comprising three domains: a seven-helix bundle that is involved in pore formation, a three-sheet domain that has been implicated in receptor binding, and a beta-sandwich motif (Li et al. (1991) *Nature* 305: 815-821).

As reported in copending U.S. application Ser. Nos. 10/606,320, filed Jun. 25, 2003, and Ser. No. 10/746,914, filed Dec. 24, 2003, the toxicity of Cry proteins can be improved by targeting the region located between alpha helices 3 and 4 of domain 1 of the endotoxin. This theory was premised on a body of knowledge concerning endotoxins, including: 1) that alpha helices 4 and 5 of domain 1 of Cry3A δ-endotoxins had been reported to insert into the lipid bilayer of cells lining the midgut of susceptible insects (Gazit et al. (1998) *Proc. Natl. Acad. Sci. USA* 95: 12289-12294); 2) the inventors' knowledge of the location of trypsin and chymotrypsin cleavage sites within the amino acid sequence of the wild-type protein; 3) the observation that the wild-type protein was more active against certain insects following in vitro activation by trypsin or chymotrypsin treatment; and 4) reports that digestion of toxins from the 3' end resulted in decreased toxicity to insects.

A series of mutations may be created and placed in a variety of background sequences to create novel polypeptides having enhanced or altered pesticidal activity. See, e.g., U.S. application Ser. Nos. 10/606,320, filed Jun. 25, 2003, and Ser. No. 10/746,914, filed Dec. 24, 2003. These mutants include, but are not limited to: the addition of at least one more protease-sensitive site (e.g., trypsin cleavage site) in the region located between helices 3 and 4 of domain 1; the replacement of an original protease-sensitive site in the wild-type sequence with a different protease-sensitive site; the addition of multiple protease-sensitive sites in a particular location; the addition of amino acid residues near protease-sensitive site(s) to alter folding of the polypeptide and thus enhance digestion of the polypeptide at the protease-sensitive site(s); and adding mutations to protect the polypeptide from degradative digestion that reduces toxicity (e.g., making a series of mutations wherein the wild-type amino acid is replaced by valine to protect the polypeptide from digestion). Mutations may be used singly or in any combination to provide polypeptides of the invention.

In this manner, the invention provides sequences comprising a variety of mutations, such as, for example, a mutation that comprises an additional, or an alternative, protease-sensitive site located between alpha-helices 3 and 4 of domain 1 of the encoded polypeptide. A mutation which is an additional or alternative protease-sensitive site may be sensitive to several classes of proteases such as serine proteases, which include trypsin and chymotrypsin, or enzymes such as elastase. Thus, a mutation which is an additional or alternative protease-sensitive site may be designed so that the site is readily recognized and/or cleaved by a category of proteases, such as mammalian proteases or insect proteases. A protease-sensitive site may also be designed to be cleaved by a particular class of enzymes or a particular enzyme known to be produced in an organism, such as, for example, a chymotrypsin produced by the corn earworm *Heliothis zea* (Lenz et al. (1991) *Arch. Insect Biochem. Physiol.* 16: 201-212). Mutations may also confer resistance to proteolytic digestion, for example, to digestion by chymotrypsin at the C-terminus of the peptide.

The presence of an additional and/or alternative protease-sensitive site in the amino acid sequence of the encoded polypeptide can improve the pesticidal activity and/or specificity of the polypeptide encoded by the nucleic acids of the invention. Accordingly, the Cry9 family nucleotide sequences of the invention can be recombinantly engineered or manipulated to produce polypeptides having improved or altered insecticidal activity and/or specificity compared to that of an unmodified wild-type δ-endotoxin. In addition, the mutations disclosed herein may be placed in or used in conjunction with other nucleotide sequences to provide improved properties. For example, a protease-sensitive site that is readily cleaved by insect chymotrypsin, e.g., a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be placed in a Cry9 family background sequence to provide improved toxicity to that sequence. In this manner, the invention provides toxic polypeptides with improved properties.

For example, a mutagenized Cry9 family nucleotide sequence can comprise additional mutants that comprise additional codons that introduce a second trypsin-sensitive amino acid sequence (in addition to the naturally occurring trypsin site) into the encoded polypeptide. An alternative addition mutant of the invention comprises additional codons designed to introduce at least one additional different protease-sensitive site into the polypeptide, for example, a chymotrypsin-sensitive site located immediately 5' or 3' of the naturally occurring trypsin site. Alternatively, substitution mutants may be created in which at least one codon of the nucleic acid that encodes the naturally occurring protease-sensitive site is destroyed and alternative codons are introduced into the nucleic acid sequence in order to provide a different (e.g., substitute) protease-sensitive site. A replacement mutant may also be added to a Cry9 family sequence in which the naturally-occurring trypsin cleavage site present in the encoded polypeptide is destroyed and a chymotrypsin or elastase cleavage site is introduced in its place.

It is recognized that any nucleotide sequence encoding the amino acid sequences that are proteolytic sites or putative proteolytic sites (for example, sequences such as NGSR (SEQ ID NO:38), RR, or LKM) can be used and that the exact identity of the codons used to introduce any of these cleavage sites into a variant polypeptide may vary depending on the use, i.e., expression in a particular plant species. It is also recognized that any of the disclosed mutations can be introduced into any polynucleotide sequence of the invention that comprises the codons for amino acid residues that provide the native trypsin cleavage site that is targeted for modification. Accordingly, variants of either full-length endotoxins or fragments thereof can be modified to contain additional or alternative cleavage sites, and these embodiments are intended to be encompassed by the scope of the invention disclosed herein.

It will be appreciated by those of skill in the art that any useful mutation may be added to the Cry9 family sequences of the invention so long as the encoded polypeptides retain pesticidal activity. Thus, Cry9 family sequences may also be mutated so that the encoded polypeptides are resistant to proteolytic digestion by chymotrypsin. More than one recognition site can be added in a particular location in any combination, and multiple recognition sites can be added to or removed from the endotoxin. Thus, additional mutations can comprise three, four, or more recognition sites. It is to be recognized that multiple mutations can be engineered in any suitable polynucleotide sequence; accordingly, either full-length Cry9 family sequences or fragments thereof can be modified to contain additional or alternative cleavage sites as well as to be resistant to proteolytic digestion. In this manner, the invention provides Cry9 family endotoxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with the wild-type endotoxins or by comparing mutant endotoxins which differ in their amino acid sequence. Putative proteolytic sites and proteolytic sites include, but are not limited to, the following sequences: RR, a trypsin cleavage site; LKM, a chymotrypsin site; and NGSR (SEQ ID NO:38), a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Compositions of the invention include nucleic acids, and fragments and variants thereof, that encode pesticidal polypeptides. In particular, the present invention provides for isolated nucleic acid molecules comprising nucleotide sequences encoding the amino acid sequences shown in SEQ ID NOs: 2, 4, 6, 25, 27, 29, and 31, or the nucleotide sequences comprised by the DNA deposited in a bacterial host as Patent Deposit Nos. PTA-5550 and PTA-5551. Further provided are polypeptides having an amino acid sequence encoded by a nucleic acid molecule described herein, for example those set forth in SEQ ID NOs: 1, 3, 5, 24, 26, 28, and 30, those deposited in a bacterial host as Patent Deposit Nos. PTA-5550 and PTA-5551, and fragments and variants thereof.

Plasmids containing the nucleotide sequences of the invention were deposited with the Patent Depository of the American Type Culture Collection (ATCC), 10801 University Blvd., Manassas, Va., 20110-2209 on Sep. 25, 2003 and assigned Patent Deposit Nos. PTA-5550 and PTA-5551. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Also of interest are optimized nucleotide sequences encoding the pesticidal proteins of the invention. As used herein, the phrase "optimized nucleotide sequences" refers to nucleic acids that are optimized for expression in a particular organism, for example a plant. Optimized nucleotide sequences may be prepared for any organism of interest using methods known in the art. See, for example, U.S. application Ser. Nos. 10/606,320, filed Jun. 25, 2003, and Ser. No. 10/746,914, filed Dec. 24, 2003, which describe an optimized nucleotide sequence encoding a disclosed pesticidal protein. In this example, the nucleotide sequence was prepared by reverse-translating the amino acid sequence of the protein and changing the nucleotide sequence so as to comprise maize-preferred codons while still encoding the same amino acid sequence. This procedure is described in more detail by Murray et al. (1989) *Nucleic Acids Res.* 17:477-498. Optimized nucleotide sequences find use in increasing expression of a pesticidal protein in a plant, for example monocot plants of the Gramineae (Poaceae) family such as, for example, a maize or corn plant.

The invention further provides isolated pesticidal (e.g., insecticidal) polypeptides encoded by either a naturally-occurring or modified (e.g., mutagenized or truncated) nucleic acid of the invention. More specifically, the invention provides polypeptides comprising an amino acid sequence set forth in SEQ ID NOs: 2, 4, 6, 25, 27, 29, and 31, and the polypeptides encoded by nucleic acids described herein, for example those set forth in SEQ ID NOs: 1, 3, 5, 24, 26, 28, and 30, and fragments and variants thereof.

In particular embodiments, pesticidal proteins of the invention provide full-length δ-endotoxin proteins, fragments of full-length δ-endotoxins, and variant polypeptides that are produced from mutagenized nucleic acids designed to introduce particular amino acid sequences into polypeptides of the invention. In particular embodiments, the amino acid sequences that are introduced into the polypeptides comprise a sequence that provides a cleavage site for an enzyme such as a protease.

It is known in the art that the pesticidal activity of *Bacillus thuringiensis* endotoxins is typically activated by cleavage of the peptide in the insect gut by various proteases. Because peptides may not always be cleaved with complete efficiency in the insect gut, fragments of a full-length endotoxin may have enhanced pesticidal activity in comparison to the full-length endotoxin itself. Thus, some of the polypeptides of the invention embody fragments of a full-length δ-endotoxin, and some of the polypeptide fragments, variants, and mutations will have enhanced pesticidal activity relative to the activity of the naturally occurring δ-endotoxin from which they are derived, particularly if the naturally occurring endotoxin is not activated in vitro with a protease prior to screening for activity. Thus, provided are truncated versions or fragments of the Cry9 family sequences. For example, SEQ ID NO: 2 provides a polypeptide that embodies a truncated version, or fragment, of the polypeptide set forth in SEQ ID NO: 4. Other examples of such truncated versions or fragments are set forth in SEQ ID NOs:2, 4, 6, 29, and 31, and in SEQ ID NOs: 1, 3, 5, 28, and 30.

Mutations may be placed into any background sequence, including such truncated polypeptides, so long as the polypeptide retains pesticidal activity. One of skill in the art can readily compare two or more proteins with regard to pesticidal activity using assays known in the art or described elsewhere herein. It is to be understood that the polypeptides of the invention can be produced either by expression of a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as purification of a purified wild-type protein and protease digestion.

It is recognized that the pesticidal proteins may be oligomeric and will vary in molecular weight, number of residues, component peptides, activity against particular pests, and other characteristics. However, by the methods set forth herein, proteins active against a variety of pests may be isolated and characterized. The pesticidal proteins of the invention can be used in combination with Bt endotoxins or other insecticidal proteins to increase insect target range. Furthermore, the use of the pesticidal proteins of the present invention in combination with Bt δ-endotoxins or other insecticidal principles of a distinct nature has particular utility for the prevention and/or management of insect resistance. Other insecticidal agents include protease inhibitors (both serine and cysteine types), α-amylase, and peroxidase.

Fragments and variants of the nucleotide and amino acid sequences and the polypeptides encoded thereby are also encompassed by the present invention. As used herein the term "fragment" refers to a portion of a nucleotide sequence of a polynucleotide or a portion of an amino acid sequence of a polypeptide of the invention. Fragments of a nucleotide sequence may encode protein fragments that retain the biological activity of the native or corresponding full-length protein and hence possess pesticidal activity. Thus, it is acknowledged that some of the polynucleotide and amino acid sequences of the invention can correctly be referred to as both fragments and mutants.

It is to be understood that the term "fragment," as it is used to refer to nucleic acid sequences of the invention, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a Cry9 family nucleotide sequence that encodes a biologically active portion of a pesticidal protein of the invention will encode at least 15, 25, 30, 50, 100, 200, 300, 400, 500, 600, 700, 800, 900, 1,000, 1,100, or 1,200 contiguous amino acids, or up to the total number of amino acids present in a pesticidal polypeptide of the invention (for example, 613, 681, and 696 amino acids for SEQ ID NOs: 2, 4, and 6, respectively). Thus, it is understood that the invention also encompasses polypeptides that are fragments of the exemplary pesticidal proteins of the invention and having lengths of at least 15, 25, 30, 50, 100, 200, 300, 400, 500, 600, 700, 800, 900, 1,000, 1,100, or 1,200 contiguous amino acids, or up to the total number of amino acids present in a pesticidal polypeptide of the invention (for example, 1,206, 1,210, and 669 amino acids for SEQ ID NOs: 2, 4, and 6, respectively). Fragments of a Cry9 family nucleotide sequence that are useful as hybridization probes or PCR primers generally need not encode a biologically active portion of a pesticidal protein.

Thus, a fragment of a Cry9 family nucleic acid may encode a biologically active portion of a pesticidal protein, or it may be a fragment that can be used as a hybridization probe or PCR primer using methods disclosed herein. A biologically active portion of a pesticidal protein can be prepared by isolating a portion of one of the Cry9-family nucleotide sequences of the invention, expressing the encoded portion of the pesticidal protein (e.g., by recombinant expression in vitro), and assessing the activity of the encoded portion of the pesticidal protein.

Nucleic acids that are fragments of a Cry9 family nucleotide sequence comprise at least 16, 20, 50, 75, 100, 150, 200, 250, 300, 350, 400, 450, 500, 600, 700, 800, 1,000, 1,200, 1,400, 1,600, 1,800, or 2,000 nucleotides, or up to the number of nucleotides present in a Cry9 family nucleotide sequence disclosed herein (for example, 1,841, 2,043, and 2,088 nucleotides for SEQ ID NOs: 1, 3, and 5, respectively). For example, SEQ ID NO: 1 represents a fragment of SEQ ID NO: 3. More specifically, particular embodiments of the nucleic acids of the invention disclose fragments derived from (e.g., produced from) a first nucleic acid of the invention, wherein the fragment encodes a truncated Cry9 family endotoxin characterized by pesticidal activity. The truncated polypeptide encoded by the polynucleotide fragments of the invention are characterized by pesticidal activity that is either equivalent to, or improved, relative to the activity of the corresponding full-length polypeptide encoded by the first nucleic acid from which the fragment is derived. In some embodiments, nucleic acid fragments of the invention are truncated at the 3' end of the native or corresponding full-length coding sequence. Nucleic acid fragments may also be truncated at both the 5' and 3' end of the native or corresponding full-length coding sequence.

The term "variants" is used herein to refer to substantially similar sequences. For nucleotide sequences, conservative variants include those sequences that, because of the degeneracy of the genetic code, encode the amino acid sequence of one of the pesticidal polypeptides of the invention. Naturally occurring allelic variants such as these can be identified with the use of well-known molecular biology techniques, such as, for example, polymerase chain reaction (PCR) and hybridization techniques as outlined herein.

Variant nucleotide sequences also include synthetically derived nucleotide sequences, such as those generated, for example, by using site-directed mutagenesis but which still encode a pesticidal protein of the invention, such as a mutant endotoxin. Generally, variants of a particular nucleotide sequence of the invention will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the invention may differ from that sequence by as few as 1-15 nucleotides, as few as 1-10, such as 6-10, as few as 5, as few as 4, 3, 2, or even 1 nucleotide.

Variants of a particular nucleotide sequence of the invention (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO: 6 are disclosed. Percent sequence identity between any two polypeptides can be calculated using sequence alignment programs described elsewhere herein using default parameters. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

As used herein, the term "variant protein" encompasses polypeptides that are derived from a native protein by: deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term "variant protein" encompasses biologically active fragments of a native protein that comprise a sufficient number of contiguous amino acid residues to retain the biological activity of the native protein, i.e., to have pesticidal activity. Such pesticidal activity may be different or improved relative to the native protein or it may be unchanged, so long as pesticidal activity is retained.

Variant proteins encompassed by the present invention are biologically active, that is they continue to possess the desired biological activity of the native protein, that is, pesticidal activity as described herein. Such variants may result from, for example, genetic polymorphism or from human manipulation. Biologically active variants of a native pesticidal protein of the invention will have at least about 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The invention further encompasses a microorganism that is transformed with at least one nucleic acid of the invention, with an expression cassette comprising the nucleic acid, or with a vector comprising the expression cassette. In some embodiments, the microorganism is one that multiplies on plants. An embodiment of the invention relates to an encapsulated pesticidal protein which comprises a transformed microorganism capable of expressing at least one pesticidal protein of the invention.

The invention provides pesticidal compositions comprising a transformed microorganism of the invention. In such embodiments, the transformed microorganism is generally present in the pesticidal composition in a pesticidally effective amount, together with a suitable carrier. The invention also encompasses pesticidal compositions comprising an isolated protein of the invention, alone or in combination with a transformed organism of the invention and/or an encapsulated pesticidal protein of the invention, in an insecticidally effective amount, together with a suitable carrier.

The invention further provides a method of increasing insect target range by using a pesticidal protein of the invention in combination with at least one other or "second" pesticidal protein. Any pesticidal protein known in the art can be employed in the methods of the present invention. Such pesticidal proteins include, but are not limited to, Bt δ -endotoxins, protease inhibitors, α-amylases, and peroxidases.

The invention also encompasses transformed or transgenic plants comprising at least one nucleotide sequence of the invention. In some embodiments, the plant is stably transformed with a nucleotide construct comprising at least one nucleotide sequence of the invention operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes whole plants, plant organs (e.g., leaves, stems, roots, etc.), seeds, plant cells, and progeny of same. Parts of transgenic plants are within the scope of the invention and comprise, for example, plant cells, protoplasts, tissues, callus, embryos as well as flowers, stems, fruits, leaves, and roots originating in transgenic plants or their progeny previously transformed with a DNA molecule of the invention and therefore consisting at least in part of transgenic cells.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The class of plants that can be used in the methods of the invention is generally as broad as the class of higher plants amenable to transformation techniques, including both monocotyledonous and dicotyledonous plants. Such plants include, for example, *Solanum tuberosum* and *Zea mays*.

While the invention does not depend on a particular biological mechanism for increasing the resistance of a plant to a plant pest, expression of the nucleotide sequences of the invention in a plant can result in the production of the pesticidal proteins of the invention and in an increase in the resistance of the plant to a plant pest. The plants of the invention find use in agriculture in methods for impacting insect pests. Certain embodiments of the invention provide transformed crop plants, such as, for example, maize plants, which find use in methods for impacting insect pests of the plant, such as, for example, European corn borer.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences of proteins of agricultural interest.

Thus, the Cry9 family proteins of the invention may be altered in various ways including amino acid substitutions, deletions, truncations, and insertions. Methods for such manipulations are generally known in the art. For example, amino acid sequence variants of the pesticidal proteins can be prepared by introducing mutations into a synthetic nucleic acid (e.g., DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York), and the references cited therein.

The mutagenized Cry9 family nucleotide sequences of the invention may be modified so as to change about 1, 2, 3, 4, 5, 6, 8, 10, 12 or more of the amino acids present in the primary sequence of the encoded polypeptide. Alternatively, even more changes from the native sequence may be introduced such that the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more of the codons altered, or otherwise modified compared to the corresponding wild-type protein. In the same manner, the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more additional codons compared to the corresponding wild-type protein. It should be understood that the mutagenized Cry9 family nucleotide sequences of the present invention are intended to encompass biologically functional, equivalent peptides which have pesticidal activity, such as an improved pesticidal activity as determined by antifeedant properties against fall armyworm larvae. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary amino acid substitution groups that take various of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the invention include both the naturally occurring sequences and mutant forms. Likewise, the proteins of the invention encompass both naturally occurring proteins and variations (e.g., truncated polypeptides) and modified (e.g., mutant) forms thereof. Such variants will continue to possess the desired pesticidal activity. Obviously, the mutations that will be made in the nucleotide sequence encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al. (1985) *J. Econ. Entomol.* 78: 290-293 and Czapla and Lang (1990) *J. Econ. Entomol.* 83: 2480-2485, herein incorporated by reference.

Variant nucleotide sequences and proteins also encompass sequences and proteins derived from a mutagenic and recombinogenic procedure such as DNA shuffling. With such a procedure, one or more different Cry9 family coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence of the invention may be shuffled between the Cry9 family nucleotide sequences of the invention and corresponding portions of other known Cry nucleotide sequences to obtain a new gene coding for a protein with an improved property of interest.

Properties of interest include, but are not limited to, pesticidal activity per unit of pesticidal protein, protein stability, and toxicity to non-target species particularly humans, livestock, and plants and microbes that express the pesticidal polypeptides of the invention. The invention is not bound by a particular shuffling strategy, only that at least one nucleotide sequence of the invention, or part thereof, is involved in such a shuffling strategy. Shuffling may involve only nucleotide sequences disclosed herein or may additionally involve shuffling of other nucleotide sequences known in the art. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire Cry9 family sequences set forth herein or to fragments thereof are encompassed by the present invention. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook". See also Innis et al., eds. (1990) *PCR Protocols. A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Thus, for example, probes for hybridization can be made by labeling synthetic oligonucleotides based on the Cry9 family sequences of the invention. Methods for preparation of probes for hybridization and for construction of cDNA and genomic libraries are generally known in the art and are disclosed in Sambrook.

For example, an entire Cry9 family sequence disclosed herein, or one or more portions thereof, may be used as a probe capable of specifically hybridizing to corresponding Cry9 family sequences and messenger RNAs. To achieve specific hybridization under a variety of conditions, such probes include sequences that are unique among Cry9 family sequences and are generally at least about 10 or 20 nucleotides in length. Such probes may be used to amplify corresponding Cry9 family sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138: 267-284: $T_m$=81.5° C.+16.6 (log M)+0.41 (% GC)-0.61 (% form)-500/L; where M is the molarity of monovalent cations, % GC is the percentage of guanosine and cytosine nucleotides in the DNA, "% form" is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Washes are typically performed at least until equilibrium is reached and a low background level of hybridization is achieved, such as for 2 hours, 1 hour, or 30 minutes.

$T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See also Sambrook. Thus, isolated sequences that encode a Cry9 family protein of the invention and hybridize under stringent conditions to the Cry9-family sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Center for Biotechnology Information website on the world wide web at www.ncbi.hlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. The term "equivalent program" as used herein refers to any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%. 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the invention additionally encompass all complementary forms of such constructs, molecules, and sequences. Further, the nucleotide constructs, nucleotide molecules, and nucleotide sequences of the present invention encompass all nucleotide constructs, molecules, and sequences which can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the invention also encompass all forms of nucleotide constructs including, but not limited to, single-stranded forms, double-stranded forms, hairpins, stem-and-loop structures, and the like.

A further embodiment of the invention relates to a transformed organism such as an organism selected from the group consisting of plant and insect cells, bacteria, yeast, baculoviruses, protozoa, nematodes, and algae. The transformed organism comprises: a DNA molecule of the invention, an expression cassette comprising the said DNA molecule, or a vector comprising the said expression cassette, which may be stably incorporated into the genome of the transformed organism.

The Cry9 family sequences of the invention are provided in expression cassettes for expression in the organism of interest. The cassette will include 5' and 3' regulatory sequences operably linked to a Cry9 family sequence of the invention. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the Cry9 family sequence to be under the transcriptional regulation of the regulatory regions. The expression cassette may additionally contain selectable marker genes.

The expression cassette will include in the 5' to 3' direction of transcription: a transcriptional and translational initiation region (i.e., a promoter), a Cry9 family DNA sequence of the invention, and a transcriptional and translational termination region (i.e., termination region) functional in the organism serving as a host. The transcriptional initiation region (i.e., the promoter) may be native, analogous, foreign or heterologous to the host organism and/or to the Cry9 family sequence of the invention. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the Cry9 family sequence of the invention, it is intended that the promoter is not the native or naturally occurring promoter for the operably linked Cry9 family sequence of the invention. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the Cry9 family sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) Nucleic Acids Res. 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV $^{35}$S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the present invention in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIPI (Rohmeier et al. (1993) *Plant Mol. Biol.* 22: 783-792; Eckelkamp et al. (1993) *FEBS Letters* 323: 73-76); MPI gene (Corderok et al. (1994) *Plant J* 6(2): 141-150); and the like, herein incorporated by reference.

Additionally, pathogen-inducible promoters may be employed in the methods and nucleotide constructs of the present invention. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) Molecular Plant-Microbe Interactions 2:325-331; Somsisch et al. (1986) Proc. Natl. Acad. Sci. USA 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean α-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core $^{35}$S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481; and U.S. application Ser. Nos. 10/004,357; and 10/427,692); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in The Operon, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; *Labow et al.* (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology, Vol.* 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the present invention.

The methods of the invention involve introducing a polypeptide or polynucleotide into a plant. “Introducing” is intended to mean presenting to the plant the polynucleotide or polypeptide in such a manner that the sequence gains access to the interior of a cell of the plant. The methods of the invention do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

“Stable transformation” is intended to mean that the nucleotide construct introduced into a plant integrates into the genome of the plant and is capable of being inherited by the progeny thereof. “Transient transformation” is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6: 923-926); and Lecl transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D’Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the Cry9 family sequences of the invention can be provided to a plant using a variety of transient transformation methods. Such transient transformation methods include, but are not limited to, the introduction of the Cry9 family protein or variants and fragments thereof directly into the plant or the introduction of the Cry9 family transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cry9 family polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the invention may be provided to the plant by contacting the plant with a virus or viral nucleic acids. Generally, such methods involve incorporating the nucleotide construct of interest within a viral DNA or RNA molecule. It is recognized that the recombinant proteins of the invention may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the invention, may have the desired pesticidal activity. Such viral polyproteins and the nucleotide sequences that encode for them are encompassed by the present invention. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The invention further relates to plant-propagating material of a transformed plant of the invention including, but not limited to, seeds, tubers, corms, bulbs, leaves, and cuttings of roots and shoots.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the present invention include crop plants (for example, corn, alfalfa, sunflower, *Brassica*, soybean, cotton, safflower, peanut, sorghum, wheat, millet, tobacco, etc.), such as corn and soybean plants.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (Agrostispalustris); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore *paspalum* (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,736,514; 5,723,756; 5,593,881; and Geiser et al. (1986) *Gene* 48:109), pentin (described in U.S. Pat. No. 5,981,722) and the like. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,049); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262: 1432; and Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene as disclosed in U.S. application Ser. Nos. 10/004,357; and 10/427,692); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170: 5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Compositions of the invention find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a nucleotide sequence encoding a pesticidal protein of the invention may be treated with a seed protectant coating comprising a seed treatment compound, such as, for example, captan, carboxin, thiram, methalaxyl, pirimiphos-methyl, and others that are commonly used in seed treatment. In one embodiment within the scope of the invention, a seed protectant coating comprising a pesticidal composition of the invention is used alone or in combination with one of the seed protectant coatings customarily used in seed treatment.

It is recognized that the genes encoding the pesticidal proteins can be used to transform insect pathogenic organisms. Such organisms include baculoviruses, fungi, protozoa, bacteria, and nematodes.

A gene encoding a pesticidal protein of the invention may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected.

These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) *Molecular Cloning: A Laboratory Manual*, ed. Maniatis et al. (Cold Spring Harbor Laboratory Press, Cold Spring Harbor, N.Y.), hereinafter "Sambrook II"; Davis et al., eds. (1980) *Advanced Bacterial Genetics* (Cold Spring Harbor Laboratory Press), Cold Spring Harbor, N.Y.; and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Genes encoding the pesticidal proteins of the invention can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the invention can be introduced into a root-colonizing *Bacillus cereus* by standard methods known in the art.

Genes encoding pesticidal proteins can be introduced, for example, into the root-colonizing *Bacillus* by means of electrotransformation. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria, such as *E. coli*, for example. Advantages of having pesticidal proteins secreted are: (1) avoidance of potential cytotoxic effects of the pesticidal protein expressed; and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli* for example the OmpA protein (Ghrayeb et al. (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Pesticidal proteins of the invention can be fermented in a bacterial host and the resulting bacteria processed and used as a microbial spray in the same manner that *Bacillus thuringiensis* strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express *Bacillus thuringiensis* endotoxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EPA 0192319, and the references cited therein.

In the present invention, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal composition(s) that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins produced by the bacterial strains of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluant before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins, of the invention can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In other embodiments of the invention, it may be advantageous to treat the Cry9 family polypeptides with a protease, for example trypsin, to activate the protein prior to application of a pesticidal protein composition of the invention to the environment of the target pest. Methods for the activation of protoxin by a serine protease are well known in the art. See, for example, Cooksey (1968) *Biochem. J.* 6:445-454 and Carroll and Ellar (1989) *Biochem. J.* 261:99-105, the teachings of which are herein incorporated by reference. For example, a suitable activation protocol includes, but is not limited to, combining a polypeptide to be activated, for example a purified cry9_rv1 polypeptide (e.g., having the amino acid sequence set forth in SEQ ID NO:2), and trypsin at a 1/100 weight ratio of cry9_rv1 protein/trypsin in 20 nM $NaHCO_3$, pH 8 and digesting the sample at 36° C. for 3 hours.

The compositions (including the transformed microorganisms and pesticidal proteins of the invention) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the pesticidal protein and/or transformed microorganisms of the invention may be mixed with grain to protect the grain during storage. It is generally important to obtain good control of pests in the early stages of plant growth, as this is the time when the plant can be most severely damaged. The compositions of the invention can conveniently contain another insecticide if this is thought necessary. In an embodiment of the invention, the composition is applied directly to the soil, at a time of planting, in granular form of a composition of a carrier and dead cells of a *Bacillus* strain or transformed microorganism of the invention. Another embodiment is a granular form of a composition comprising an agrochemical such as, for example, an herbicide, an insecticide, a fertilizer, an inert carrier, and dead cells of a *Bacillus* strain or transformed microorganism of the invention.

The embodiments of the present invention may be effective against a variety of pests. For purposes of the present invention, pests include, but are not limited to, insects, fungi, bacteria, nematodes, acarids, protozoan pathogens, animal-parasitic liver flukes, and the like. Pests of particular interest are insect pests, particularly insect pests that cause significant damage to agricultural plants. The term "insect pests" as used herein refers to insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails*, and *Yponomeuta padella.*

Also, the embodiments of the present invention may be effective against insect pests, including but not limited to insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, Coleoptera, etc., particularly Lepidoptera. Insect pests of the invention for the major crops include, but are not limited to: Maize: *Ostrinia nubilalis*, European corn borer; *Agrotis ipsilon*, black cutworm; *Helicoverpa zeae*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; western corn rootworm, e.g., *Diabrotica virgifera virgifera*; northern corn rootworm, e.g., *Diabrotica longicornis barberi*; southern corn rootworm, e.g., *Diabrotica undecimpunctata howardi; Melanotus* spp., wireworms; *Cyclocephala borealis*, northern masked chafer (white grub); *Cyclocephala immaculata*, southern masked chafer (white grub); Popilliajaponica, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blotch leafminer; *Anaphothrips obscrurus*, grass thrips; *Solenopsis milesta*, thief ant; *Tetranychus urticae*, two spotted spider mite; *Sorghum: Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; chinch bug, e.g., *Blissus leucopterus leucopterus; Contarinia sorghicola*, sorghum midge; *Tetranychus cinnabarinus*, carmine spider mite; *Tetranychus urticae*, two-spotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Elasmopalpus*

*lignosellus*, lesser cornstalk borer; *Oulema melanopus*, cereal leaf beetle; *Hypera punctata*, clover leaf weevil; southern corn rootworm, e.g., *Diabrotica undecimpunctata howardi*; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murteldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; boll weevil, e.g., *Anthonomus grandis; Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhoper; chinch bug, e.g., *Blissus leucopterus leucopterus; Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus; Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufimanus, Meligethes nigrescens, Meligethes canadianus*, and *Meligethes viridescens*; Potato: *Leptinotarsa decemlineata*, Colorado potato beetle.

Furthermore, embodiments of the present invention may be effective against Hemiptera such as *Lygus hesperus, Lygus lineolaris, Lygus pratensis, Lygus rugulipennis* Popp, *Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster*, Coreidae, Pyrrhocoridae, Timidae, Blostomatidae, Reduviidae, and Cimicidae. Pests of interest also include *Araecerus fasciculatus*, coffee bean weevil; *Acanthoscelides obtectus*, bean weevil; *Bruchus rufimanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple curculio; *Sternechus paludatus*, bean stalk weevil; *Hypera brunnipennis*, Egyptian alfalfa weevil; *Sitophilus granaries*, granary weevil; *Craponius inaequalis*, grape curculio; *Sitophilus zeamais*, maize weevil; *Conotrachelus nenuphar*, plum curculio; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; *Tribolium castaneum*, red flour beetle; *Tenebrio molitor*, yellow mealworm.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests may be tested for pesticidal activity of compositions of the invention in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83(6): 2480-2485. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXPERIMENTAL

Example 1

Bioassay for Testing the Pesticidal Activity of *B. thuringiensis* Strains Against European Corn Borer Insect diets for European corn borer ("ECB," e.g., *Ostrinia nubilalis*) were employed; many are known in the art. See, for example, Singh and Moore, eds. (1985) *Handbook of Insect Rearing*, vol. 1 (Elsevier, New York, N.Y.), herein incorporated by reference.

*Bacillus* colonies were selected from a fresh plate and used to inoculate 25 mL of either C2 or T3 media, further described in detail below. These cultures were grown at 28° C. for 6 days and checked for sporulation. Sporulated cultures were spun at 10,000×g for 15 minutes and the supernatant was removed. The pellet was resuspended in 2.5 mL of 50 mM sodium carbonate, 10 mM DTT, and stored at 4° C. overnight. Insect bioassays were conducted to determine the presence of compounds having pesticidal activity. Bioassays were carried out in 96 well microtiter plates where each well contained 200 μL insect diet. 25 μL samples were topically applied to the diet surface per well. Once the samples dried, individual wells were infested with eggs (approximately 10 eggs/well). Assay trays were sealed to prevent larval escape and placed in a growth chamber (27° C.) for 5 days. Each 96-well plate contained assay samples plus appropriate controls. Each sample was replicated four times on individual plates. Samples were evaluated for their ability to kill or stunt insect larvae.

TABLE 1

| | T3 | |
|---|---|---|
| Insect | Dissolved crystal | Activated crystal |
| Corn earworm | − | − |
| European corn borer | + | + |
| Fall armyworm | − | N/D |
| Western corn rootworm | − | − |

+ = all larvae dead
− = all larvae apparently normal

Secondary assays were then performed to confirm the activity and determine whether it was heat labile. Heated samples were placed in a boiling water bath for 40 minutes, allowed to cool, and bioassayed as previously described. Results were as follows:

TABLE 2

| | T3 | | | |
|---|---|---|---|---|
| | Dissolved crystal | | Activated crystal | |
| Insect | No Δ | Δ | No Δ | Δ |
| CEW | − | − | − | − |
| ECB | + | − | + | − |

+ = all larvae dead
− = all larvae apparently normal

The digestibility of the crystal protein produced by bacterial strain DP 1019 was assessed. Crystal protein from strain DP 1019 was incubated in simulated gastric fluid for various amounts of time at 37° C. Simulated gastric fluid (SGF) consists of 0.016% (weight/volume) pepsin, 2 mg/ml NaCl, and 63 mM HCl (pH 1.2)). See Astwood and Fuchs (1996) *Food Tech.* 50: 83-88; and Fu and Abbot (2002) *Agric. Food Chem.* 50: 7154-7160. SGF was prepared on the day of the experiment, and the ratio of DP 1019 crystal protein to pepsin was 1:32 (weight:weight). The incubation was stopped by adding LDS sample buffer (see Sambrook II) with reducing agent β-mercaptoethanol and heating for 5 minutes at 100° C. Samples were then analyzed using SDS-PAGE (results shown in FIG. 2). The gel analysis showed that full-length 1019 crystal protein (110 kDa) was degraded to a 62 kDa fragment, which was degraded within one minute. Thus, DP 1019 crystal protein is highly susceptible to degradation by simulated gastric fluid.

Media: T3 media contains the following, per liter: 3 g tryptone (which is the pancreatic digest of casein); 2 g tryptose (which is the mixture of enzymatically digested proteins); 1.5 g yeast extract; and 0.005 g of $MgCl_2$. To prepare T3 media, these powders are diluted with 0.05 M sodium phosphate buffer (pH 6.8) and autoclaved on liquid cycle for 15 minutes to sterilize. C2 media contains the following, per liter: 10.0 g glucose; 2.0 g peptone; 5.0 g casamino acids; 0.247 g $MgCl_2$; 2.0 g yeast extract; 0.058 g $MnCl_2.4H_2O$; 0.1 g $CaCl_2$; 0.005 g $ZnSO_4.7H_2O$; 0.005 g $CaSO_4.7H_2O$; 1.619 g $NH_4Cl$; 0.005 g $FeSO_4.7H_2O$; 4.66 g $K_2HPO_4$; and 3.11 g $KH_2PO_4$. To prepare C2 media, these powders are diluted with distilled water, filtered through a 0.221 μm filter to sterilize (not autoclaved) and stored at 4° C.

Example 2

Isolation and Assay of Pesticidal Proteins

Based on the results of the experiments described in Example 1, large-scale cultures of *bacillus* DP 1019 were grown for protein purification. The crystal proteins were purified (see Kronstad et al. (1983) *J. Bact.* 154: 419-428) and evaluated on an SDS-PAGE gel, which revealed that only two major bands were present in the crystal fraction. Standard chromatographic procedures, including ion exchange chromatography and gel filtration, both well known in the art, were used to further purify the proteins and determine which fraction contained the pesticidal protein. The active fractions were separated on an SDS-PAGE gel and transferred to PVDF. The bands were then excised for N-terminal sequencing.

The purified proteins were sequenced, and both fractions contained the amino acid sequence XINPNLSINTXDVLQTGITIVGXVL (SEQ ID NO: 7). This amino acid sequence was used to search sequence databases, and these searches revealed that the protein was related to the Cry9 protein family. Sequences of Cry9 family members were aligned and primers were designed to amplify the nucleotide sequence encoding this protein. Primer set 1 included a forward primer having the sequence GAGATGTACTACAAACAGG (SEQ ID NO: 8) and a reverse primer having the sequence CCATCCCTTGTACGTGTAAAC (SEQ ID NO: 9). These primers were used to amplify a PCR product of approximately 2 kb from the DP 1019 plasmid DNA. The PCR product was cloned into a pCR-blunt vector and sequenced, yielding the nucleotide sequence designated "cry9_rv1" and set forth in SEQ ID NO: 1.

A second PCR reaction was performed using a second set of primers, including a forward primer having the sequence GGATCCATGAATCGAAATAATCAAAATG (SEQ ID NO: 10) and a reverse primer having the sequence CTCGAGCTGTAATCCGTCCCTTGTACGTGTAAAC (SEQ ID NO: 11). This reaction produced a PCR product approximately 2 kb in length, which was also cloned into the pCR-blunt vector and sequenced. At least two species of molecule were produced by this PCR reaction, which yielded the nucleotide sequence designated "cry9_rv2," set forth in SEQ ID NO: 3, and the nucleotide sequence designated "cry9d_rv1," set forth in SEQ ID NO: 5. The cry9_rv2 sequence contains the entire sequence of cry9_rv1 and also includes an N-terminal region with an ATG codon.

The toxin domain of both genes was cloned into a pET28 vector for protein expression. The pET28 vector includes an ATG codon in frame with sequences encoding His and T7 tags so that these tags are produced as part of a fusion protein with the protein encoded by the inserted nucleotide sequences. Thus, the cry9_rv2 protein was expressed as a fusion protein from the pET28 vector as follows.

Bacterial colonies from strain 1019 were spotted on replica plates and inoculated in 5 ml of 2×YT broth with 500 μl/1000 ml kanamycin. The cultures were allowed to overnight. If no growth was present, the tubes were incubated for an additional 24 hours. Following incubation, the tubes were centrifuged at 3500 rpm for 5-8 minutes. The supernatant was discarded and the pellet resuspended in 1000 μl PBS. The sample was then transferred to 1.5 ml Eppendorf tubes and incubated on ice until the temperature was 3 to 4° C., followed by sonication for 12-15 seconds.

The fusion protein was then purified as follows. The expressed, N-terminal-His-tagged, truncated Cry9 family proteins were isolated from *E. coli* lysates by affinity chromatography using a nickel affinity column. The column fractions with the protein of interest were dialyzed extensively against 10 mM Tris-HCl (pH 8.5) and then concentrated using Centriprep® (Millipore Corp.) centrifugal filter units with a MW cutoff of 10,000 according to the manufacturer's directions. The concentrated Cry9 family protein samples were tested for the presence of pesticidal activity against European corn borer as described in Example 1.

The bioassays were then scored for mortality and the results were as follows:

TABLE 3

| Toxin concentration (μg/cm$^2$) | Dead | Moribund | Stunted | Healthy | Total | Mortality (%) |
|---|---|---|---|---|---|---|
| 9 | 32 | 4 | 1 | | 37 | 86 |
| 4.5 | 34 | | 7 | | 41 | 83 |
| 2.25 | 23 | 1 | 6 | | 30 | 77 |
| 1.125 | 7 | | 18 | 1 | 26 | 27 |
| 0.5625 | 4 | 1 | 15 | 1 | 21 | 19 |
| 0.2813 | 1 | | 15 | 15 | 31 | 3 |
| 0.1406 | | | 20 | 5 | 25 | 0 |
| 0.0703 | | | 17 | 14 | 31 | 0 |
| 0.0352 | 4 | | 11 | 10 | 25 | 16 |

Thus, these results demonstrate the pesticidal activity of cry9_rv2 protein against European corn borer larvae.

Example 3

Determination of $LC_{50}$ using ECB Incorporated Assays

Insect diets for European corn borer ("ECB," e.g., *Ostrinia nubilalis*) were employed; many are known in the art. See, for example, Singh and Moore, eds. (1985) *Handbook of Insect Rearing*, vol. 1 (Elsevier, New York, N.Y.), herein incorporated by reference. For use in the ECB Incorporated Assays, diet was prepared with a reduced amount of water to allow for the addition of protein compounds to make up the final volume of diet. For example, if a 500 μl sample was to be added to 3500 μl of artificial diet, the amount of water added to the diet was reduced to allow for the addition of the sample so that the final volume remained the same (e.g., see calculations in Table 4 below).

TABLE 4

Formulation of Diet
Protein Concentration (mg/ml): 1.00

| Rate (ppm) | Total protein (ug) | Stock (ul) | Buffer (ul) | Final vol sample (ul) | Diet (ul) | Sample + Diet vol (ul) |
|---|---|---|---|---|---|---|
| 150.00 | 600.00 | 600.00 | −100.00 | 500 | 3500 | 4000 |
| 100.00 | 400.00 | 400.00 | 100.00 | 500 | 3500 | 4000 |
| 75.00 | 300.00 | 300.00 | 200.00 | 500 | 3500 | 4000 |
| 50.00 | 200.00 | 200.00 | 300.00 | 500 | 3500 | 4000 |
| 37.50 | 150.00 | 150.00 | 350.00 | 500 | 3500 | 4000 |
| 25.00 | 100.00 | 100.00 | 400.00 | 500 | 3500 | 4000 |
| 18.75 | 75.00 | 75.00 | 425.00 | 500 | 3500 | 4000 |
| 12.50 | 50.00 | 50.00 | 450.00 | 500 | 3500 | 4000 |
| 6.25 | 25.00 | 25.00 | 475.00 | 500 | 3500 | 4000 |
| 3.13 | 12.50 | 12.50 | 487.50 | 500 | 3500 | 4000 |
| 1.56 | 6.24 | 6.24 | 493.76 | 500 | 3500 | 4000 |
| 0.00 | 0.00 | 0.00 | 500.00 | 500 | 3500 | 4000 |
| Totals | 1918.74 | 1918.74 | 4081.26 | | | |

The artificial diet was placed in a beaker on a heating plate while stirring. Artificial diet was then placed in a 50-ml conical tube and cooled to 40° C. prior to addition of the protein sample. After addition of the sample, the diet was mixed well and 240 μl of diet was placed into individual wells of a 96-well plate. The artificial diet was allowed to cool and harden. If necessary, the diet was dried under a ventilation hood for 10-15 minutes. The surface of the diet was monitored carefully to prevent overdrying.

Each well was infested with 1-3 larvae per well, depending on the particular assay. The plates were heat-sealed with Mylar film to prevent insect escape and yet allow for adequate ventilation. The plates were incubated for the desired duration (usually about 6 days) and then the insects were evaluated for survival and weight.

These assays were used to determine the $LC_{50}$ of Cry9 family toxins. For each toxin, samples were tested at the following concentrations:

TABLE 5

Concentrations Tested

| sample | toxin concentration (ppm) |
|---|---|
| 1 | 100 |
| 2 | 75 |
| 3 | 50 |
| 4 | 37.5 |
| 5 | 25 |
| 6 | 18.75 |
| 7 | 12.5 |
| 8 | 6.25 |
| 9 | 3.13 |
| 10 | 1.56 |
| 11 | 0 |

For the $LC_{50}$ determination for the Cry9 family endotoxin having the amino acid sequence set forth in SEQ ID NO: 4, each well was infested with one ECB neonate, for a total of 14 insects tested per treatment. The covered plates were placed in a small box to help reduce moisture loss and were incubated at 27° C. for 6 days. Each assay was scored for mortality, and $LC_{50}$ was calculated using PROBIT analysis (SAS Institute) for each test as well as for the combination of 3 repetitions of the test. These results were as follows:

TABLE 6

| LC$_{50}$ determination using ECB incorporated assays for the Cry9 Family Endotoxin of SEQ ID NO: 4 | | | |
|---|---|---|---|
| | | 95% fiducial limits | |
| Reps | LC$_{50}$ | (lower) | (upper) |
| 1 | 11.62 | 8.2 | 15.6 |
| 2 | 23.1 | 18.8 | 27.9 |
| 3 | 19.7 | 15.6 | 24.4 |
| Combined | 17.3 | 14.9 | 19.9 |

For the LC$_{50}$ determination for the Cry9 family endotoxin having the amino acid sequence set forth in SEQ ID NO: 6, each well was infested with one ECB neonate, for a total of 7 insects tested per treatment. The covered plates were placed in a small box to help reduce moisture loss and were incubated at 27° C. for 6 days. Each assay was scored for mortality, and LC$_{50}$ was calculated using PROBIT analysis (SAS Institute) for each test as well as for the combination of 3 repetitions of the test. These results were as follows:

TABLE 7

| LC$_{50}$ determination using ECB incorporated assays for Cry9 Family Endotoxin of SEQ ID NO: 6 | | | |
|---|---|---|---|
| | | 95% fiducial limits | |
| Reps | LC$_{50}$ | (lower) | (upper) |
| 1 | 5.55 | 3.42 | 7.93 |
| 2 | 6.21 | 4.18 | 8.52 |
| 3 | 7.60 | 5.57 | 9.92 |
| Combined | 6.45 | 5.25 | 7.73 |

Example 4

Transformation of Maize by Particle Bombardment and Regeneration of Transgenic Plants Immature maize embryos from greenhouse donor plants are bombarded with a DNA molecule containing the Cry9 family nucleotide sequence (e.g., SEQ ID NO: 5) operably linked to a ubiquitin promoter and the selectable marker gene PAT (Wohlleben et al. (1988) *Gene* 70: 25-37), which confers resistance to the herbicide Bialaphos. Alternatively, the selectable marker gene is provided on a separate DNA molecule. Transformation is performed as follows. Media recipes follow below.

Preparation of Target Tissue

The ears are husked and surface sterilized in 30% Clorox™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a Cry9 family nucleotide sequence (e.g., SEQ ID NO: 5) operably linked to a ubiquitin promoter is made. For example, a suitable transformation vector comprises a UBI1 promoter from *Zea mays*, a 5' UTR from UBI1 and a UBI1 intron, in combination with a PinII terminator. The vector additionally contains a PAT selectable marker gene driven by a CAMV35S promoter and includes a CAMV35S terminator. Optionally, the selectable marker can reside on a separate plasmid. A DNA molecule comprising a Cry9-family nucleotide sequence as well as a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to a tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the Cry9 family protein by assays known in the art or as described above.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with dI $H_2O$ following adjustment to pH 5.8 with KOH); 2.0 g/l Gelrite™ (added after bringing to volume with dI $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with dI $H_2O$ following adjustment to pH 5.8 with KOH); 3.0 g/l Gelrite™ (added after bringing to volume with dI $H_2O$); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l Glycine brought to volume with polished D-1 $H_2O$) (Murashige and Skoog (1962) *Physiol. Plant.* 15: 473), 100 mg/l myo-inositol, 0.5 mg/l zeatin, 60 g/l sucrose, and 1.0 ml/l of 0.1 mM abscisic acid (brought to volume with polished dI $H_2O$ after adjusting to pH 5.6); 3.0 g/l Gelrite™ (added after bringing to volume with dI $H_2O$); and 1.0 mg/l indoleacetic acid and 3.0 mg/l Bialaphos (added after sterilizing the medium and cooling to 60° C.).

Hormone-free medium (272V) comprises 4.3 g/l MS salts (GIBCO 11117-074), 5.0 ml/I MS vitamins stock solution (0.100 g/l nicotinic acid, 0.02 g/l thiamine HCl, 0.10 g/l pyridoxine HCl, and 0.40 g/l Glycine brought to volume with polished dI $H_2O$), 0.1 g/l myo-inositol, and 40.0 g/l sucrose (brought to volume with polished dI $H_2O$ after adjusting pH to 5.6); and 6 g/l Bacto-agar (added after bringing to volume with polished dI $H_2O$), sterilized and cooled to 60° C.

Example 5

*Agrobacterium*-Mediated Transformation of Maize and Regeneration of Transgenic Plants For *Agrobacterium*-mediated transformation of maize with a Cry9 family nucleotide sequence (e.g., SEQ ID NO: 3), the method of Zhao can be used (U.S. Pat. No. 5,981,840, and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the Cry9 family nucleotide sequence (SEQ ID NO: 3) to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 6

Transformation of Soybean Embryos

Soybean embryos are bombarded with a plasmid containing the Cry9 family nucleotide sequence of SEQ ID NO: 30 operably linked to a pinII promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327: 70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the $^{35}$S promoter from Cauliflower Mosaic Virus (Odell et al. (1985) *Nature* 313: 810-812), the hygromycin phosphotransferase gene from plasmid pJR225 (from *E. coli*; Gritz et al. (1983) *Gene* 25: 179-188), and the 3' region of the nopaline synthase gene from the T-DNA of the Ti plasmid of *Agrobacterium tumefaciens*. The expression cassette comprising a Cry9 family nucleotide sequence (e.g., SEQ ID NO: 3) operably linked to the pinII promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Transformation of Sunflower Meristem Tissue

Sunflower meristem tissues are transformed with an expression cassette containing a Cry9 family nucleotide sequence (e.g., SEQ ID NO: 30) operably linked to a wun1 promoter as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox™ bleach solution with the addition of two drops of Tween™ 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.* 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the a Cry9 family nucleotide sequence (e.g., SEQ ID NO: 3 operably linked to the wun1 promoter is introduced into *Agrobacterium* strain EHA 105 via freeze-thawing as described by Holsters et al. (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for pesticidal activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite™, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by pesticidal activity analysis of leaf extracts while transgenic seeds harvested from NPTII-positive To plants are identified by analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox™ bleach solution with the addition of two to three drops of Tween™ 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar™ at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar™), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino)ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for pesticidal activity using assays known in the art. After positive (i.e., for Cry9 family expression) explants are identified, those shoots that fail to exhibit pesticidal activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for expression of a toxin from the Cry9-family are grafted to Pioneer® hybrid 6440 in vitro-grown sunflower seedling rootstock. The rootstocks are prepared in the following manner. Seeds are dehulled and surface-sterilized for 20 minutes in a 20% Clorox™ bleach solution with the addition of two to three drops of Tween™ 20 per 100 ml of solution, and are rinsed three times with distilled water. The sterilized seeds are germinated on the filter moistened with water for three days, then they are transferred into 48 medium (half-strength MS salt, 0.5% sucrose, 0.3% Gelrite™ pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 8

Breeding

A. Pedigree Breeding

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., the expression of protein having pesticidal activity), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

B. Recurrent Selection and Mass Selection

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the embodiments.

That which is claimed:

1. An isolated nucleic acid comprising a nucleotide sequence that encodes a polypeptide having pesticidal activity against at least one pest, wherein said nucleotide sequence is selected from the group consisting of:

(a) the nucleotide sequence set forth in SEQ ID NO:3, 26, or 30;

(b) a nucleotide sequence encoding the amino acid sequence set forth in SEQ ID NO:4, 27, or 31; and (c) a nucleotide sequence having at least 95% sequence identity across the full length of a nucleotide sequence of (a).

2. The nucleic acid of claim 1, wherein said nucleic acid is optimized for expression in a plant.

3. An expression cassette comprising a nucleic acid according to claim 1, wherein said nucleic acid is operably linked to a promoter that drives expression in a microorganism or in a plant cell.

4. A transformed plant comprising in its genome at least one stably incorporated nucleotide construct comprising a nucleotide sequence that encodes a polypeptide that is pesticidal for at least one pest belonging to the order Lepidoptera, wherein said coding sequence is operably linked to a promoter that drives expression in a plant cell and wherein said coding sequence is selected from the group consisting of:

(a) the nucleotide sequence set forth in SEQ ID NO:3, 26, or 30;

(b) a nucleotide sequence encoding the amino acid sequence set forth in SEQ ID NO:4, 27, or 31;

(c) a nucleotide sequence characterized by at least 95% sequence identity across the full length of a nucleotide sequence of (a); and (e) a nucleotide sequence according to any one of (a) to (c) that has been mutated to comprise codons optimized for expression in a plant.

5. The plant of claim 4, wherein said plant is a monocot.

6. The plant of claim 4, wherein said plant is a dicot.

7. Transformed seed of the plant of claim 4, wherein the seed comprises the nucleotide construct.

* * * * *

UNITED STATES PATENT AND TRADEMARK OFFICE

CERTIFICATE OF CORRECTION

PATENT NO. : 7,541,517 B2
APPLICATION NO. : 11/471879
DATED : June 2, 2009
INVENTOR(S) : Flannagan et al.

It is certified that error appears in the above-identified patent and that said Letters Patent is hereby corrected as shown below:

Column 30,
Line 33, "α" should read --β--.

Column 34,
Line 1, "cassaya" should read --cassava--.

Column 43,
Line 18, "murteldtiana" should read --murtfeldtiana--.

Column 44,
Line 3, "Nysius raphanus" should read --Nysiusraphanus--;
Line 4, "Timidae" should read --Tinidae--.

Column 46,
Line 16, "0.221μm" should read --0.22μm--.

Signed and Sealed this

Tenth Day of November, 2009

David J. Kappos
*Director of the United States Patent and Trademark Office*